United States Patent

Caimi et al.

US007615365B2

(10) Patent No.: US 7,615,365 B2
(45) Date of Patent: Nov. 10, 2009

(54) α(1,6)-LINKED GLUCOSE OLIGOSACCHARIDE HYDROLYZING ENZYME POLYNUCLEOTIDES AND POLYPEPTIDES AND METHODS OF USE THEREOF

(75) Inventors: Perry G. Caimi, Kennett Square, PA (US); Mario W. Chen, Chadds Ford, PA (US); Vasantha Nagarajan, Wilmington, DE (US); Jean-Francois Tomb, Wilmington, DE (US); Siqun Wang, Wilmington, DE (US); Yuying Zhang, New Hope, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/852,834

(22) Filed: Sep. 10, 2007

(65) Prior Publication Data

US 2009/0068704 A1    Mar. 12, 2009

Related U.S. Application Data

(62) Division of application No. 10/648,152, filed on Aug. 25, 2003, now Pat. No. 7,268,221.

(60) Provisional application No. 60/405,896, filed on Aug. 23, 2002.

(51) Int. Cl.
 C12N 9/00 (2006.01)
 C12N 9/24 (2006.01)
 C12N 1/20 (2006.01)
 C12N 15/00 (2006.01)
 C07H 21/04 (2006.01)

(52) U.S. Cl. .................... 435/200; 435/183; 435/252.3; 435/320.1; 536/23.2

(58) Field of Classification Search ........................ None
 See application file for complete search history.

(56) References Cited

U.S. PATENT DOCUMENTS 5,686,276 A    11/1997 Laffend et al.

FOREIGN PATENT DOCUMENTS

EP    0 511 393 A1    11/1992

EP    1 227 152 A1    7/2002
WO    WO 2004/018645  *  3/2004

OTHER PUBLICATIONS

Chica et al. Curr Opin Biotechnol. Aug. 2005;16(4):378-84.*
Keija Kainuma, Starch, 2nd ed., Starch Oligosaccharides: Linear, Branched, and Cyclic, Whistler, Bemiller, and Pashcall eds., Academic Press, Orlando, FL, pp. 125-150, 1984.
Crueger and Crueger, Organic feedstocks produced by fermentation, Biotechnology: A Textbook of Industrial Microbiology, Sinauer Associates: Sunderland, MA, pp. 124-174, 1990.
Blanchard, Processing with Enzymes, Technology of Corn Wet Milling, Chapter 6, Elsevier, Amsterdam, The Netherlands, pp. 177-215, 1992.
Atkinson & Mavituna, Product Formation, Chapter 6, Biochemical Engineering and Biotechnology Handbook, 2nd Ed.; Stockton Press: New York, pp. 243-364, 1991.
T. Norman Palmer et al., The Pathway of Exogenous and Endogenous Carbohydrate Utilization in *Escherichia coli*: A Dual Function for the Enzymes of the Maltose Operon, Eur. J. Biochem., vol. 39:601-612, 1973.
Lin, Oligosaccharides and Disaccharides, Sugars, Polyols, and Carboxylates, *Escherichia coli* and *Salmonella typhimuium*, Neidhart, ed.; American Society for Microbiology, Washington, D.C., pp. 245-265, 1987.
V. V. Krasikov et. al., Glucosidases, Biochemistry, 2001, pp. 267-281, vol. 66.
Mikio Yamamoto et. al., Purification and Properties of an Oligo-1,6-D-Glucosidase From an Alkalophilic *bacillus* Species.
International Search Report Dated Jun. 22, 2005, International Application No. PCT/US03/26760, International Filing Date: Aug. 25, 2003.

* cited by examiner

*Primary Examiner*—Christian L Fronda

(57) ABSTRACT

This invention relates to a method for utilizing less purified starch in fermentation processes. One example is a recombinant *E. coli* containing a exogenous extracellular isoamylase activity that is capable of utilizing small oligomers containing (1,6) linkages (including but not limited to isomaltose and panose) in fermentations to produce useful products. The invention is useful in large-scale industrial biofermentations by reducing the cost of the substrate carbohydrate.

25 Claims, 4 Drawing Sheets

Figure 1A:
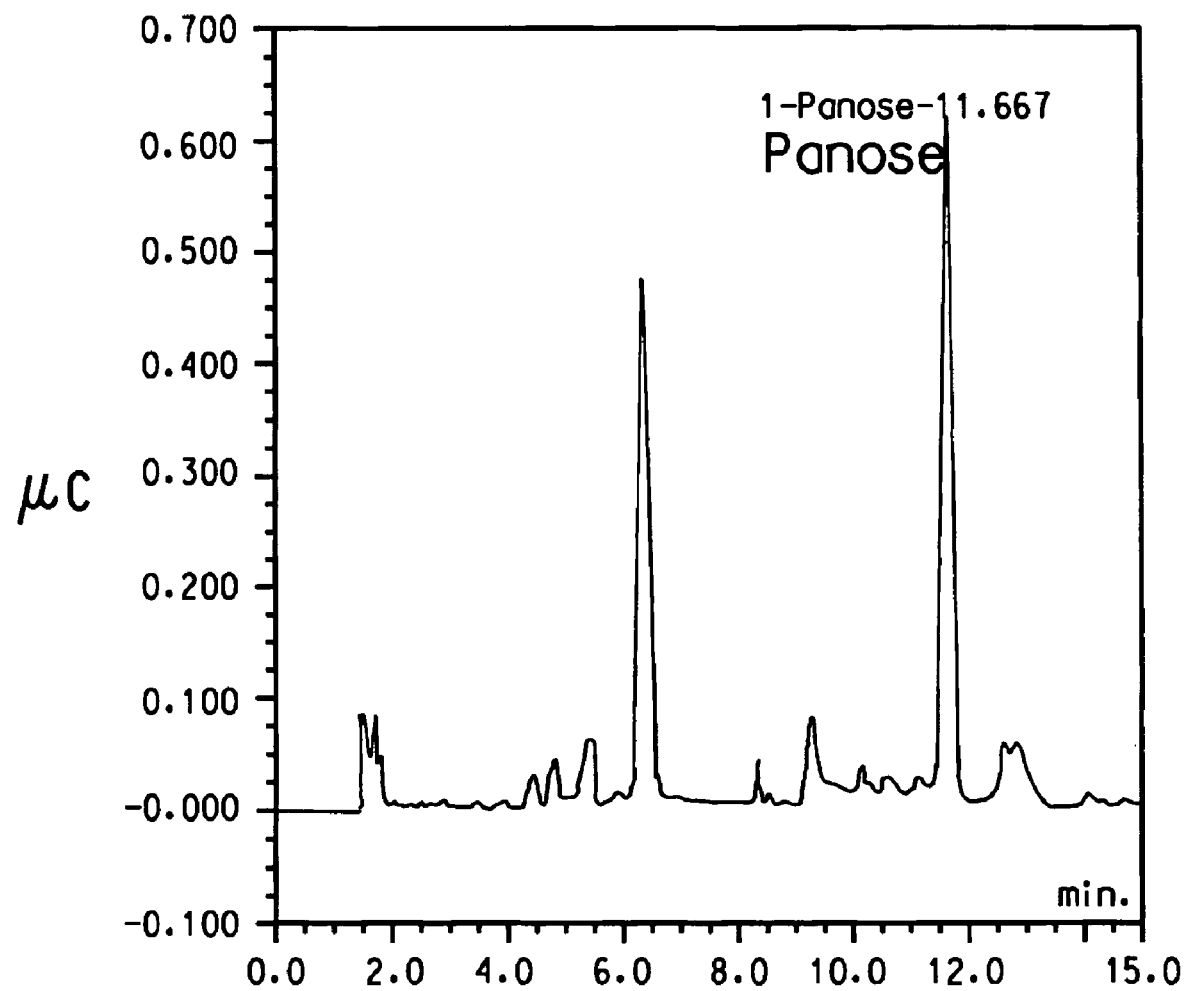
Figure 1B:
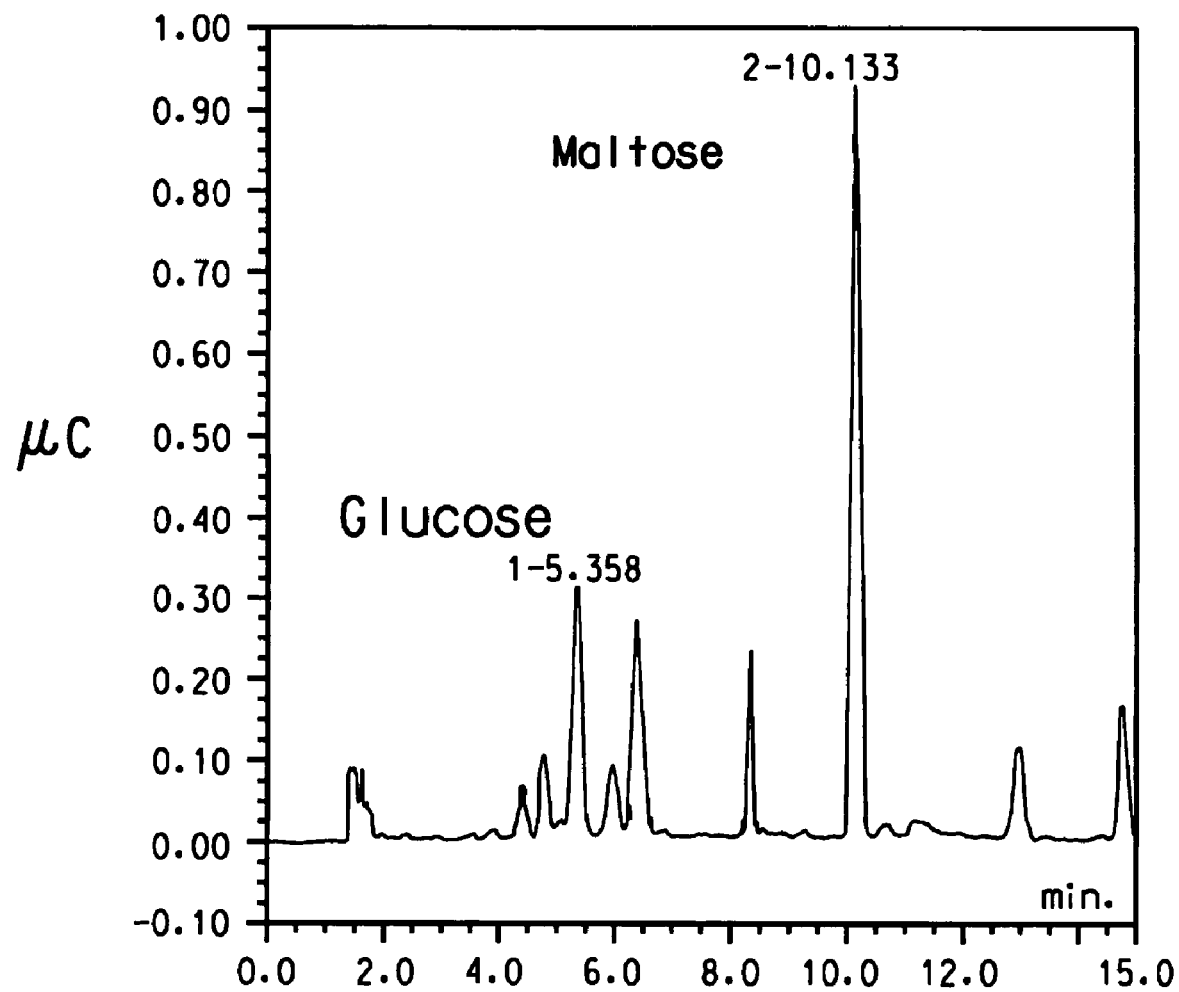
Figure 1C:
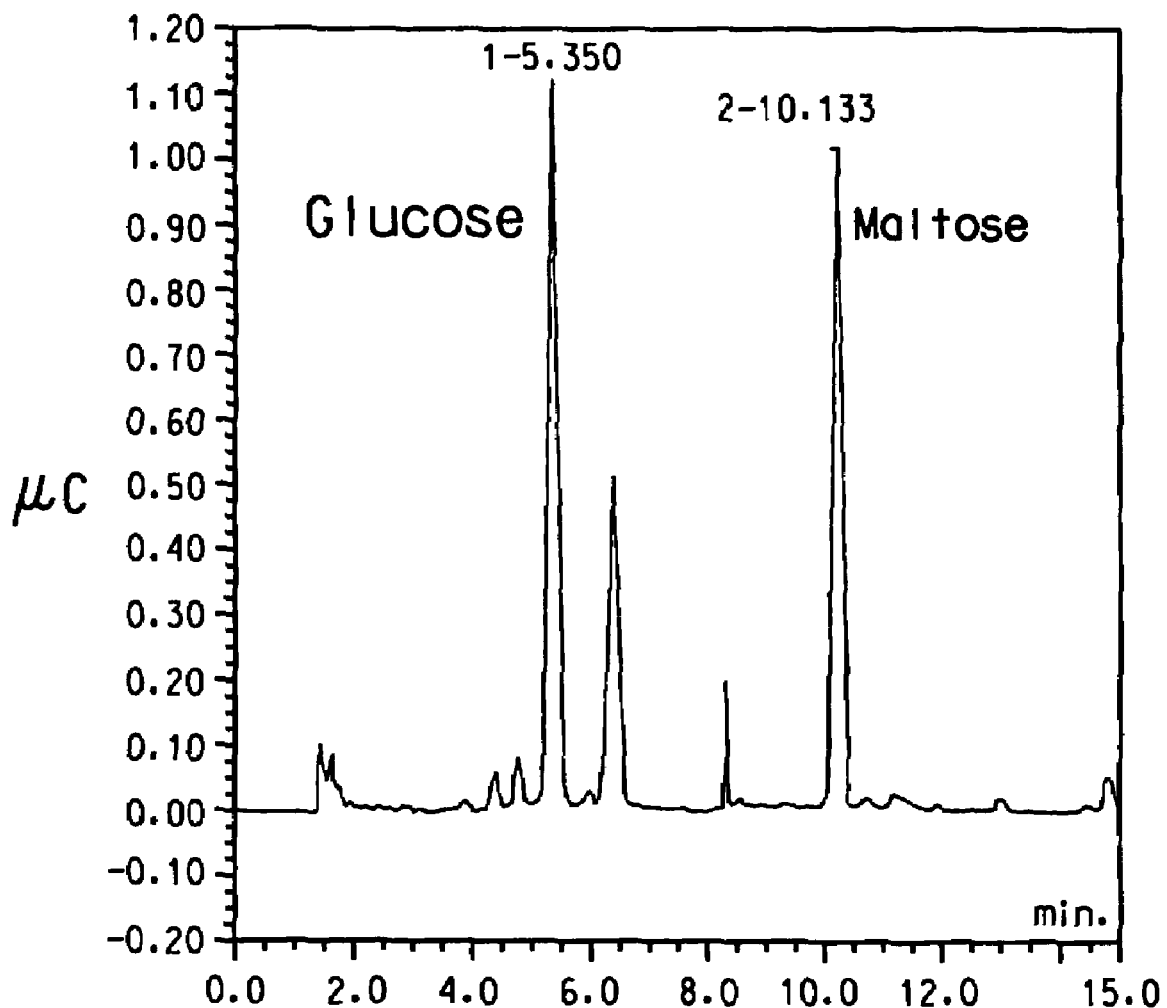

ދ# α(1,6)-LINKED GLUCOSE OLIGOSACCHARIDE HYDROLYZING ENZYME POLYNUCLEOTIDES AND POLYPEPTIDES AND METHODS OF USE THEREOF

CROSS-REFERENCE TO RELATED APPLICATION

This patent application is a divisional of the U.S. patent application Ser. No. 10/648,152, filed Aug. 25, 2003, now granted as U.S. Pat. No. 7,268,221, both of which claims the benefit of U.S. Provisional Application No. 60/405,896, filed Aug. 23, 2002.

FIELD OF THE INVENTION

The present invention relates to the field of molecular biology. More specifically it describes microbial hosts containing genes that express enzymes that effectively convert starch products into a fermentation product.

BACKGROUND OF THE INVENTION

Fermentation is an important technology for the biocatalytic conversion of renewable feedstocks into desirable products. Carbohydrates are traditional feedstocks in the fermentation industry. It is often the case that carbohydrates used as a substrate contribute more to the cost of manufacture than any other single component. Depending on the particular process, from 25 to 70% of the total cost of fermentation may be due to the carbohydrate source. (Crueger and Crueger, *Biotechnology: A Textbook of Industrial Microbiology*, Sinauer Associates: Sunderland, Mass., pp 124-174 (1990); Atkinson and Mavituna, *Biochemical Engineering and Biotechnology Handbook*, $2^{nd}$ ed.; Stockton Press: New York, pp 243-364 (1991)). For such economic reasons, highly purified glucose or sucrose can seldom be used as a substrate.

Starch, a carbohydrate, is a mixture of two different polysaccharides each consisting of chains of linked, repeating monosaccharide (glucose) units. The mixture consists of two separate polysaccharides, amylose and amylopectin. Amylose is a linear polysaccharide with glucose units connected exclusively through α(1,4) glycosidic linkages. Glucose units in amylopectin are also linked through α(1,4) glycosidic linkages, and additionally are linked through α(1,6) glycosidic linkages, about one every 30 glucose residues. The ratio of amylopectin to amylose in starch varies from one plant species to another, but is generally in the range of 3-4 to 1 (Kainuma, pp 125-150 in Starch; Whistler, Bemiller, and Pashcall eds., Academic Press, Orlando, Fla. (1984)).

Commercial starch is produced primarily through the wet milling process. The final products from a wet mill, however, include very little unprocessed starch. By far, the majority of products made are in the form of fully processed starch (monosaccharides, including glucose) or smaller degradation products derived from starch. Typically, an amylase enzyme is used to break starch into smaller chains (Blanchard, Technology of Corn Wet Milling (1992), Elseiver, Amsterdam, The Netherlands, pp. 174-215). Various commercial sources of α-amylase exist, but, regardless of enzyme source, reaction products are generally the same with respect to size and linkage-type. Amylase digestion of starch results in a product known as a limit dextrin that includes small starch chains containing 2-10 glucose units (oligosaccharides). Because amylase cannot hydrolyze the α(1,6) glycosidic linkages in amylopectin, limit dextrins contain both α(1,4)- and α(1,6)-linked glucose oligosaccharides. Alternatively, raw starch may be treated by non-enzymatic means (for example, by acid hydrolysis) to produce starch products substantially similar to limit dextrin.

In the wet milling industry, limit dextrins are further processed into glucose for use as a carbon source for fermentations to produce various chemicals, commercial enzymes, or antibiotics. Relatively pure glucose is preferred as a carbohydrate source when the popular biocatalyst, *Escherichia Coli*, is used in the fermentation process. This is because *E. coli* does not utilize components of limit dextrins (i.e., panose, isomaltose, and high molecular weight oligosaccharides with chains larger than about ten α(1,4)-linked glucose units) that are commonly contained in alternate low-cost fermentation media (Lin, *Escherichia coli* and *Salmonella typhimuium*, pp. 245-265, Neidhardt, ed.; American Society for Microbiology, Washington, D. C. (1987)). Glucose oligomers containing α(1,6)-linkages are not transported into the cell and *E. coli* does not produce an enzyme that degrades this material when supplied extracellularly (Palmer et al., *Eur. J. Biochem.* 39:601-612 (1973)).

Making relatively pure glucose from starch that is suitable for use by *E. coli* requires many process steps and additional enzymes, adding significantly to the cost of product manufacture.

Thus, the problem to be solved is the lack of a process to utilize low-cost starch products in large-scale fermentative production processes. An ability to more completely ferment low cost, partially degraded starch would lower the cost of manufacture for products made through fermentation.

SUMMARY OF THE INVENTION

Applicants have provided an isolated nucleic acid molecule encoding an α(1,6)-linked glucose oligosaccharide hydrolyzing enzyme selected from the group consisting of: (a) an isolated nucleic acid molecule encoding the amino acid sequence selected from the group consisting of SEQ ID NOs: 2, 4, and 6; (b) a nucleic acid molecule that hybridizes with (a) under the following hybridization conditions: 0.1×SSC, 0.1% SES, 65° C. and washed with 2×SSC, 0.1% SDS followed by 0.1×SSC, 0.1% SDS; and (c) a nucleic acid molecule that is complementary to (a) or (b).

Applicants have provided nucleic acid compositions comprising coding regions for a signal peptide and an α(1,6)-linked glucose oligosaccharide hydrolyzing enzyme such that a chimeric protein is expressed that directs the hydrolyzing activity external to the cytoplasm (extracellularly). The isolated nucleic acid molecule may encode a signal peptide as set forth in SEQ ID NO:24 or SEQ ID NO:25. The nucleic acid sequence of the signal sequence is SEQ ID NO:26 or SEQ ID NO:27. The isolated nucleic acid molecule may encode an α(1,6)-linked glucose oligosaccharide hydrolyzing polypeptide as set forth in SEQ ID NOs:2, 4, 6, 17, or 31.

Applicants have provided recombinant organisms comprising an α(1,6)-linked glucose oligosaccharide hydrolyzing enzyme that enables the utilization of exogenously added α(1,6)-linked glucose oligosaccharides (e.g., isomaltose and panose) for the fermentative production of useful products. The α(1,6)-linked glucose oligosaccharide hydrolyzing polypeptide may be selected from SEQ ID NO:2, SEQ ID NO:6, SEQ ID NO:17, or SEQ ID NO:31. The invention also encompasses an α(1,6)-linked glucose oligosaccharide hydrolyzing polypeptide encoded by the nucleic acid molecule set forth in SEQ ID NOs:1, 3, 5, 16, or 30. The invention also includes isolated nucleic acid molecules selected from the group consisting of SEQ ID NO:3, SEQ ID NO:28, SEQ ID NO:32, SEQ ID NO:34, SEQ ID NO:36, SEQ ID NO:38, SEQ ID NO:40, or SEQ ID NO:42. The invention also includes the polypeptide SEQ ID NO:4, SEQ ID NO:29, SEQ ID NO:33, SEQ ID NO:35, SEQ ID NO:37, SEQ ID NO:39, SEQ ID NO:41, and SEQ ID NO:43.

The invention also encompasses a chimeric gene comprising the isolated nucleic acid molecules set forth herein operably linked to suitable regulatory sequences. The suitable regulatory sequence is selected from the group comprising CYC1, HIS3, GAL1, GAL10, ADH1, PGK, PHO5, GAPDH, ADC1, TRP1, URA3, LEU2, ENO, TPI, AOX1, lac, ara, tet, trp, $IP_L$, $IP_R$, T7, tac, trc, apr, npr, nos, and GI. The invention encompasses transformed host cells wherein the chimeric gene is integrated into the chromosome or is plasmid-borne.

Applicants have also provided a method for degrading limit dextrin comprising:
(a) contacting a transformed host cell comprising:
  (i) a nucleic acid molecule encoding the enzymes selected from the group consisting of SEQ ID NOs:2, 6, 17 and 31;
  (ii) a nucleic acid molecule that hybridizes with (i) under the following hybridization conditions: 0.1×SSC, 0.1% SDS, 65° C. and washed with 2×SSC, 0.1% SDS followed by 0.1×SSC, 0.1% SDS; or
  (iii) a nucleic acid molecule that is complementary to (i) or (ii),
  with an effective amount of limit dextrin substrate under suitable growth conditions; and
(b) optionally recovering the product of step (a).

The invention also encompasses a method for producing a target molecule in a recombinant host cell comprising: contacting a transformed host cell comprising: (i) an isolated nucleic acid molecule encoding a chimeric protein comprised of a signal peptide linked to an α(1,6)-linked glucose oligosaccharide hydrolyzing polypeptide; (ii) a nucleic acid molecule that hybridizes with (i) under the following hybridization conditions: 0.1×SSC, 0.1% SDS, 65° C. and washed with 2×SSC, 0.1% SDS followed by 0.1×SSC, 0.1% SDS; or (iii) a nucleic acid molecule that is complementary to (i) or (ii); and a chimeric gene for converting monosaccharides to the target molecule, in the presence of limit dextrin under suitable conditions whereby the target molecule is produced; and optionally recovering the target molecule produced. The signal peptide may be selected from SEQ ID NO:24 or SEQ ID NO:25. The α(1,6)-linked glucose oligosaccharide hydrolyzing polypeptide may be selected from SEQ ID NO:2, SEQ ID NO:6, SEQ ID NO:17 or SEQ ID NO:31. The transformed host cell may be selected from bacteria, yeast or filamentous fungi. This invention includes producing 1,3 propanediol, glycerol, and cell mass from limit dextrin.

The invention also encompasses a polypeptide having an amino acid sequence that has at least 69% identity based on the BLASTP method of alignment when compared to a polypeptide having the sequence as set forth in SEQ ID NO:17, the polypeptide having an α(1,6)-linked glucose oligosaccharide hydrolyzing activity.

BRIEF DESCRIPTION OF THE DRAWINGS, BIOLOGICAL DEPOSITS, AND SEQUENCE DESCRIPTIONS

Figure 1D:
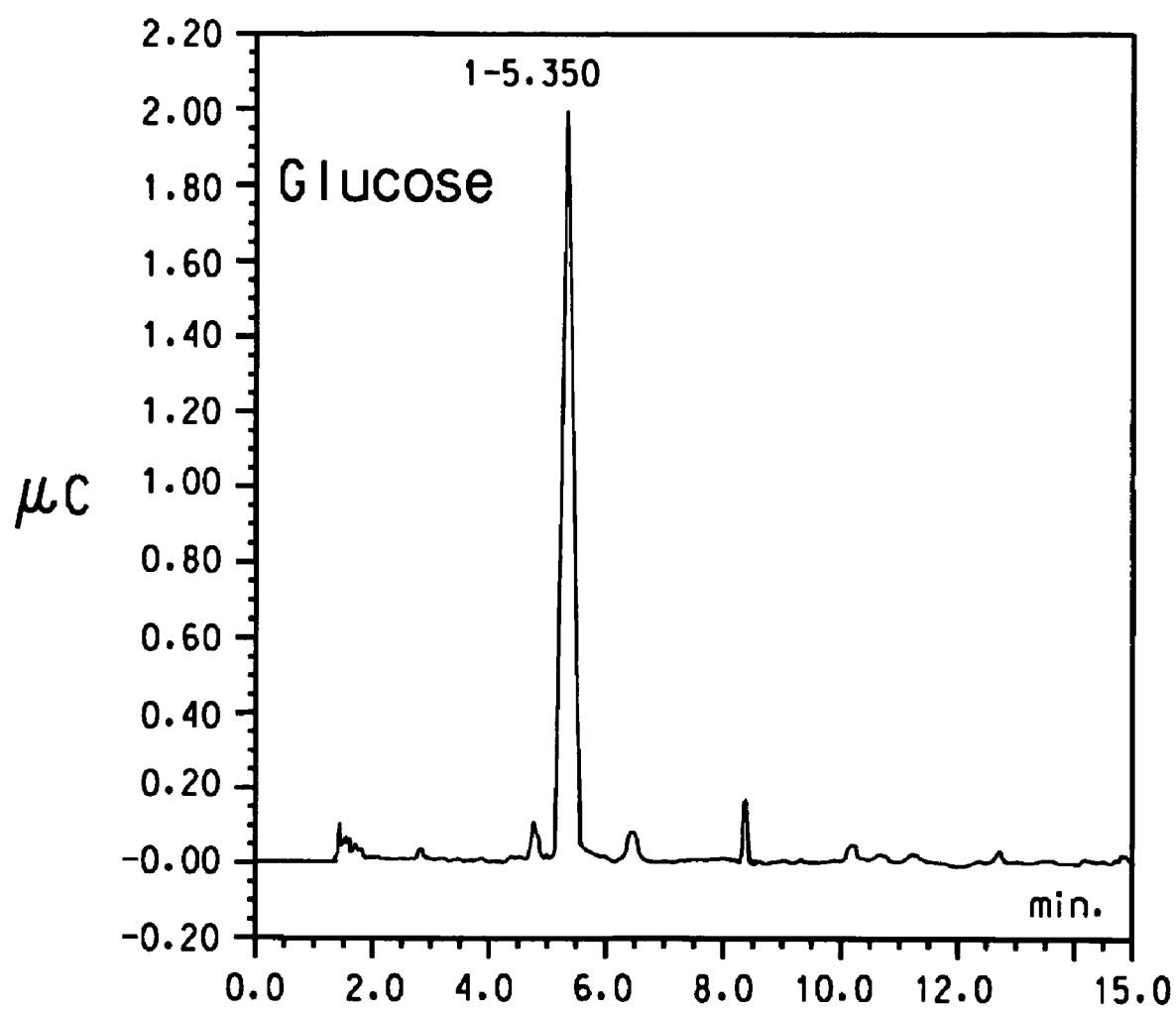

FIGS. 1a through 1d show the results of the *E. coli* strain DH5a containing the plasmids pUC18 (FIG. 1a) (negative control) and pUC18 containing the mature coding sequence from the clones j20 (FIG. 1b), k1 (FIG. 1c), or h12 (FIG. 1d). Total protein extracts were isolated from sonicated cells and incubated with panose (250 µg/ml) at 37° C. for two hours. A high performance anion exchange chromatogram of the products after digestion is shown.

Applicants made the following biological deposits under the terms of the Budapest Treaty on the International Recognition of the Deposit of Micro-organisms for the Purposes of Patent Procedure at the American Type Culture Collection (ATCC) 10801 University Boulevard, Manassas, Va. 20110-2209:

| Depositor Identification Reference | Int'l. Depository Designation | Date of Deposit |
|---|---|---|
| *Escherichia coli* RJ8n | ATCC PTA-4216 | 9 Apr. 2002 |

The listed deposit(s) will be maintained in the indicated international depository for at least thirty (30) years and will be made available to the public upon the grant of a patent disclosing it. The availability of a deposit does not constitute a license to practice the subject invention in derogation of patent rights granted by government action.

Applicants provide a sequence listing containing 43 sequences. The sequences are in conformity with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions) and with the corresponding United Stats Patent and Trademark Office Rules set forth in 37 C.F.R. §1.822.

| ORF Name | Gene Name | SEQ ID Base | SEQ ID Peptide | Strain of Origin |
|---|---|---|---|---|
| mbc1g.pk007.h12 | algB | 1 | 2 | *Bifidobacterium breve* |
| mbc2g.pk018.j20 | algA | 3 | 4 | *Bifidobacterium breve* |
| mbc1g.pk026.k1 | algA | 5 | 6 | *Bifidobacterium breve* |
| dexB | dexB | 16 | 17 | *Streptococcus mutans* |

SEQ ID NOs:1-6 are nucleic and amino acid sequences of three genes/gene products obtained from *Bifidobacterium breve* ATCC 15700.

SEQ ID NOs:7-15 and 18-23 are primers for PCR.

SEQ ID NOs:16-17 are nucleic and amino acid sequences disclosed in public databases for *Streptococcus mutans* (ATCC 25175D).

SEQ ID NO:24 is the amino acid sequence for the native signal peptide from the *Bifidobacterium breve* gene, mbc2g.pk018.j20 (also contained within SEQ ID NO:3).

SEQ ID NO:25 is the amino acid sequence for the non-native signal peptide used to target enzymes coded for by the *Bifidobacterium breve* mbc1g.pk026.k1 and *Streptococcus mutans* dexB genes.

SEQ ID NO:26 is the nucleic acid sequence for the *Bifidobacterium breve* gene mbc2g.pk018.j20 signal peptide SEQ ID NO:27 is the nucleic acid sequence for the *Bacillus subtilis* neutral protease gene signal peptide.

SEQ ID NO:28 is the nucleic acid sequence for the *Bifidobacterium breve* gene mbc2g.pk018.j20 signal peptide linked to the coding sequence for the *Bifidobacterium breve* mbc2g.pk018.h12 gene.

SEQ ID NO:29 is the amino acid sequence for the *Bifidobacterium breve* gene mbc2g.pk018.j20 signal peptide linked to the amino acid sequence for the *Bifidobacterium breve* mbc2g.pk018.h12 gene.

SEQ ID NO:30 is the nucleic acid sequence for the *Bifidobacterium breve* gene mbc2g.pk018.j20 without its native signal peptide sequence.

SEQ ID NO:31 is the amino acid sequence for the *Bifidobacterium breve* gene mbc2g.pk018.j20 without its native signal peptide sequence.

SEQ ID NO:32 is the nucleic acid sequence for the *Bifidobacterium breve* gene mbc2g.pk018.j20 signal peptide linked to the coding sequence for the *Bifidobacterium breve* mbc2g.pk018.k1 gene.

SEQ ID NO:33 is the amino acid sequence for the *Bifidobacterium breve* gene mbc2g.pk018.j20 signal peptide linked to the amino acid sequence for the *Bifidobacterium breve* mbc2g.pk018.k1 gene.

SEQ ID NO:34 is the nucleic acid sequence for the *Bifidobacterium breve* gene mbc2g.pk018.j20 signal peptide linked to the coding sequence for the *Streptococcus mutans* dexB gene.

SEQ ID NO:35 is the amino acid sequence for the *Bifidobacterium breve* gene mbc2g.pk018.j20 signal peptide linked to the amino acid sequence for the *Streptococcus mutans* dexB gene.

SEQ ID NO:36 is the nucleic acid sequence for the *Bacillus subtilis* neutral protease gene signal peptide linked to the coding sequence for the *Bifidobacterium breve* mbc2g.pk018.h12 gene.

SEQ ID NO:37 is the amino acid sequence for the *Bacillus subtilis* neutral protease gene signal peptide linked to the amino acid sequence for the *Bifidobacterium breve* mbc2g.pk018.h12 gene.

SEQ ID NO:38 is the nucleic acid sequence for the *Bacillus subtilis* neutral protease gene signal peptide linked to the coding sequence for the *Bifidobacterium breve* mbc2g.pk018.j20 gene.

SEQ ID NO:39 is the amino acid sequence for the *Bacillus subtilis* neutral protease gene signal peptide linked to the amino acid sequence for the *Bifidobacterium breve* mbc2g.pk018.j20 gene.

SEQ ID NO:40 is the nucleic acid sequence for the *Bacillus subtilis* neutral protease gene signal peptide linked to the coding sequence for the *Bifidobacterium breve* mbc2g.pk018.k1 gene.

SEQ ID NO:41 is the amino acid sequence for the *Bacillus subtilis* neutral protease gene signal peptide linked to amino acid sequence for the *Bifidobacterium breve* mbc2g.pk018.k1 gene.

SEQ ID NO:42 is the nucleic acid sequence for the *Bacillus subtilis* neutral protease gene signal peptide linked to the coding sequence for the *Streptococcus mutans* dexB gene.

SEQ ID NO:43 is the amino acid sequence for the *Bacillus subtilis* neutral protease gene signal peptide linked to amino acid sequence for the *Streptococcus mutans* dexB gene.

DETAILED DESCRIPTION OF THE INVENTION

Applicants have solved the stated problem. The present invention provides several enzymes that, when expressed in a production host, enable the host to utilize α(1,6)-linked glucose oligosaccharides, which are components of low cost starch products. The invention also provides signal sequences that enable α(1,6)-linked glucose oligosaccharide hydrolyzing enzymes to be targeted extracellularly.

Low cost starch products are obtained, for example, from the action of commercially available amylase enzymes on raw starch and other feed stocks containing α(1,6)-linked glucose oligosaccharides to produce a limit dextrin. The efficient use of the low cost starch products requires genetically engineering a host organism (for example, *E. coli*), such that the recombinant organism produces an enzyme that degrades α(1,6)-linked glucose oligosaccharides. Enzymes that degrade α(1,6)-linked glucose oligosaccharides are known (Vihinen and Mantsala *Crit. Rev. in Biochem. Mol. Biol.* 4:329-427 (1989)). Further, enzymes that degrade these linkages are known to be present both intracellularly (within the cytoplasm) and extracellularly (external to the cytoplasm) in their native state.

Where a host organism lacks a transport system, engineering an intracellular enzyme to have access to limit dextrin (or other feedstocks containing α(1,6)-linked glucose oligosaccharides) supplied externally may be accomplished by adding a native or non-native signal peptide. Signal peptides enable the α(1,6)-linked glucose oligosaccharide degrading protein to be directed to an extracellular location (external to the cytoplasm), and give access to substrates not taken into the cell (Nagarajan et al., *Gene* 114:121-126 (1992)). Examples of signal peptides that translocate protein across the cell's membrane include, but are not limited to, SEQ ID NOs:24 and 25. Proteins containing a signal peptide are directed to the secretory pathway and are then translocated across the cell's membrane. The general mechanism of protein secretion is conserved among all gram-negative and gram-positive bacteria (Simonen and Palva (1993) *Microbiol. Rev.* 57:109-137; Fekkes and Driessen (1999) *Microbiol. Rev.* 63:161-173). All bacterial signal peptides contain a string of 13 to 20 hydrophobic amino acids (Bae and Schneewind, *J. Bacteriol.*, 185: 2910-2919 (2003)).

Native *E. coli* does not hydrolyze α(1,6)-glycosidic linkages, thus the compounds containing (1,6)-linkages are not utilized in fermentations. The (1,6)-linkages are hydrolyzed by both "isoamylase" and "glucosidase" enzymes (isomaltose and panose are model compounds for (1,6)-linked oligosaccharides). A recombinant *E. coli* containing a non-native extracellular "isoamylase" or "glucosidase" will utilize compounds containing (1,6)-linkages (e.g., isomaltose and panose) in fermentations to produce useful products. Further, any recombinant organism containing a non-native extracellular "isoamylase" or "glucosidase" will utilize compounds containing (1,6)-linkages more efficiently. Increased utilization efficiency will be through constitutive expression or altered timing of the recombinant "isoamylase" or "glucosidase" genes. Recombinant gene expression will also increase the level of activity over that of any endogenous "isoamylase" or "glucosidase" genes that may be present, thus increasing utilization of (1,6)-linked substrate.

The present invention may be used to produce various products of biofermentation including, but not limited to, organic acids, antibiotics, amino acids, enzymes, vitamins, alcohols such as bioethanol, and cell mass. The bio-production of glycerol, 1,3-propanediol, and cell mass using limit dextrin made available as a carbon source to the host microorganism through use of the signal peptide serve to exemplify the invention.

The polyol, 1,3-propanediol, is a monomer useful for producing polyester fibers and manufacturing polyurethanes and cyclic compounds. A process for the biological production of 1,3-propanediol by a single organism from carbon substrate such as glucose or other sugars has been described in U.S. Pat. No. 5,686,276, incorporated by reference herein.

Starch is a homopolysaccharide of glucose. It is synthesized in higher plants as a granule containing two components, amylose and amylopectin (Vihinen and Mantsala, *Crit. Rev. Biochem. Mol. Biol.*, 24:329-418 (1989)). Amylose, essentially a linear polysaccharide formed by $\alpha(1,4)$-linked glucose residues, accounts for 15-25% of the granule (content varies with plant species). By contrast, amylopectin is highly branched, with about 4 to 5% of the glucosidic linkages being $\alpha(1,6)$-linked glucose residues. Amylolytic enzymes that degrade starch are well studied. Metabolism of starch, by first degrading the polymer into individual glucose residues in higher plant species, requires the interaction of several amylolytic enzymes.

Amylolytic enzymes, acting alone, often only partially degrade starch into smaller linear or branched chains. Combinations of amylolytic enzymes or enzyme combinations along with acid treatment may be used to increase the depolymerization of starch.

Enzymes and enzyme combinations may degrade starch partially, resulting in smaller linear or branched chains, or completely to glucose. The $\alpha$-glucosidases hydrolyze both (1,4)- and (1,6)-linkages found in oligosaccharides which are formed by the action of other amylolytic enzymes such as $\alpha$-amylases, $\beta$-amylases, glucoamylases, isoamylases and pullulanases, or by acid and heat treatments.

$\alpha$-Glucosidases ($\alpha$-D-glucoside glucohydrolase; for example, EC 3.2.1.20) are distributed widely among microorganisms. They hydrolyze (1,4)- and (1,6)-linkages and liberate $\alpha$-D-glucose units from the nonreducing end. Various types of these enzymes with different (and wide) substrate specificity have been found in bacterial species of the genus *Bacillus, Streptococcus, Escherichia, Pseudomonas*, hyperthermophilic archaeobacteria such as *Pyrococcus, Thermococcus*, and *Thermotoga*, and fungal species such as *Penicillium, Tetrahymena, Saccharomyces*, and *Aspergillus*.

The enzyme from *Aspergillus niger* has been intensively studied for many years and possesses wide substrate specificity. It hydrolyzes such substrates such as maltose, kojibiose, nigerose, isomaltose, phenyl-$\alpha$-glucoside, phenyl-$\alpha$-maltoside, oligosaccharides, maltodextrin, and soluble starch. Similar properties are exhibited by $\alpha$-glucosidases from *A. oryzae, Bacillus subtilis*, and *B. cereus* and the hyperthermophilic archaea.

Oligo-(1,6)-glucosidase or isomaltase (dextrin 6-$\alpha$-D-glucanohydrolase, EC 3.2.1.10; coded for by the dexB gene) is an enzyme similar to $\alpha$-glucosidase (Krasikov et al., *Biochemistry* (Moscow). 66:332-348 (2001)). It catalyzes the hydrolysis of (1,6)-$\alpha$-D-glucosidic linkages in isomaltose and dextrins produced from starch and glycogen by $\alpha$-amylase (Enzyme Nomenclature, C. Webb, ed. (1984) Academic Press, San Diego, Calif.). The enzyme is less well distributed than the $\alpha$-glucosidases, but is found in organisms such as *Bacillus* species including *B. thermoglucosidius* KP1006, *B. cereus* ATCC 7064, and possibly *B. amyloliquefaciens* ATCC 23844 (Vihinen and Mantsala, Critical Reviews in Biochemistry. 24:329-418 (1989)), as well as *Bacillus coagulans* (Suzuki and Tomura, *Eur. J. Biochem.*, 158:77-83 (1986)). The *Bacillus* enzymes are typically 60-63 kDa in size. An oligo-(1,6)-alpha-glucosidase (EC 3.2.1.10) has also been isolated from *Thermoanaerobium* Tok6-B1, with a reported molecular mass of 30-33 kDa.

The dexB enzyme from *Steptococcus mutans* has a pattern of activity similar to the dextranase enzymes (EC 3.2.1.11) that catalyze the endohydrolysis of the (1,6)-$\alpha$-D-glucosidic linkages in dextran. There is a high degree of similarity between the dexB enzyme and *Bacillus* spp. oligo-(1,6)-glucosidases (Whiting et al., *J. Gen. Microbiol.*, 139:2019-2026 (1993)). DexB is approximately 62 kDa in size (Aduse-Opoku et al., *J. Gen Microbiol.*, 137:757-764 (1991)).

Enzymes with $\alpha(1,6)$ hydrolase activity belong to a very broad category of over 81 recognized families of glucosyl hydrolases (Henrissat, *Biochem. J.*, 280:309-316 (1991); Henrissat and Bairoch, *Biochem. J.*, 293:781-788 (1993)). The broad grouping of enzymes capable of utilizing $\alpha(1,6)$ linked glucose units as a fermentable substrate is further emphasized by demonstrating the utility of this invention, using enzymes with as little as 69% amino acid sequence identity. Enzymes with the ability to depolymerize oligosaccharides containing $\alpha(1,6)$-linked glucose residues are known and include glucoamylase, (EC 3.2.1.3, also known as amyloglucosidase), which rapidly hydrolyzes (1,6)-$\alpha$-D-glucosidic bonds or linkages when the next linkage in sequence is a (1,4)-$\alpha$-D-glucosidic linkage; $\alpha$-dextrin endo-(1,6)-$\alpha$-glucanosidase (EC 3.2.1.41, also known as pullulanase), which degrades (1,6)-$\alpha$-D-glucosidic linkages in pullulan, amylopectin, glycogen, and the $\alpha$- and $\beta$-amylase limit dextrins of amylopectin and glycogen; sucrase (EC 3.2.1.48), which is isolated from intestinal mucosa and has activity against isomaltose; isoamylase (EC 3.2.1.68), which hydrolyzes the (1,6)-$\alpha$-D-glucosidic linkages in glycogen, amylopectin and their $\beta$-limit dextrins; and glucan (1,6)-$\alpha$-glucosidase (EC 3.2.1.70), which hydrolyzes successive glucose residues from (1,6)-$\alpha$-D-glucans and derived oligosaccharides.

In the context of this disclosure, a number of terms are used.

The term "starch" refers to a homopolysaccharide composed of D-glucose units linked by glycosidic linkages that forms the nutritional reservoir in plants. Starch occurs in two forms, amylose and amylopectin. In amylose, D-glucose units are linked exclusively by $\alpha(1,4)$ glycosidic linkages. Chains composed of multiple $\alpha(1,4)$ glycosidic linkages are considered to be linear or unbranched. In amylopectin, while the predominant connection is via $\alpha(1,4)$ glycosidic linkages, the occasional presence of an $\alpha(1,6)$ glycosidic linkage forms a branch point amongst the otherwise linear sections. Amylopectin contains about one $\alpha(1,6)$ linkage per thirty $\alpha(1,4)$ linkages.

The term "monosaccharide" refers to a compound of empirical formula $(CH_2O)_n$, where $n \leq 3$, the carbon skeleton is unbranched, each carbon atom except one contains a hydroxyl group, and the remaining carbon atom is an aldehyde or ketone at carbon atom 2. The term "monosaccharide" also refers to intracellular cyclic hemiacetal or hemiketal forms. The most familiar monosaccharide is D-glucose. The cyclic form of D-glucose involves reaction of the hydroxyl group of carbon atom 5 with the aldehyde of carbon atom 1 to form a hemiacetal, the carbonyl carbon being referred to as the anomeric carbon.

The terms "glycosidic bond" and "glycosidic linkage" refers to acetals formed by reaction of an anomeric carbon with a hydroxyl group of an alcohol. Reaction of the anomeric carbon of one D-glucose molecule with the hydroxyl group on carbon atom 4 of a second D-glucose molecule leads to a (1,4) glycosidic bond or linkage. Similarly, reaction of the anomeric carbon of one D-glucose molecule with the hydroxyl group on carbon atom 6 of a second D-glucose molecule leads to a (1,6) glycosidic bond or linkage. One skilled in the art will recognize that the glycosidic linkages may occur in $\alpha$ or $\beta$ configurations. Glycosidic linkage configurations are designated by, for example, $\alpha(1,4)$ and $\alpha(1,6)$.

The term "$\alpha$" refers to the conformation of the linkage being above the plane of the ring. In contrast, a "$\beta$" linkage refers to a linkage below the plane of the ring.

The term "oligosaccharide" refers to compounds containing between two and ten monosaccharide units linked by glycosidic linkages. The term "polysaccharide" refers to compounds containing more than ten monosaccharide units linked by glycosidic linkages and generally refers to a mixture of the larger molecular weight species. A polysaccharide composed of a single monomer unit is referred to by the term "homopolysaccharide".

The term "isomaltosaccharide" refers to an oligosaccharide with at least one α(1,6)-linkage.

The term "(1,4) linkage" refers to the relationship of two saccharides in that the C1 from one saccharide unit is bonded to the C4 of the second saccharide unit.

The term "(1,6) linkage" refers to the relationship of two saccharides in that the C1 from one saccharide unit is bonded to the C6 of the second saccharide unit.

The terms "amylase" and "α-amylase" refer to an enzyme that catalyzes the hydrolysis of an α(1,4) glycosidic linkage. The activity, hydrolysis of an α(1,4) glycosidic linkage, is referred to by the terms "amylase activity" or "amylolytic activity". Amylases include but are not limited to the group comprising IUBMB classifications EC 3.2.1.1 (amylase), EC 3.2.1.60 ((1,4)-α-maltotetraohydrolase), and EC 3.2.1.98 ((1,4)-α-maltohexaosidase).

The terms "isoamylase" and "α-isoamylase" refer to an enzyme that catalyzes the hydrolysis of an α(1,6) glycosidic linkage. The activity, hydrolysis of an α(1,6) glycosidic linkage, is referred to by the terms "isoamylase activity" or "isoamylolytic activity". Isoamylases include but are not limited to the group comprising IUBMB classifications EC 3.2.1.10 (oligo-(1,6)-glucosidase), EC 3.2.1.11 (dextranase), EC 3.2.1.41 (pullulanase), and EC 3.2.1.68 (isoamylase).

The terms "glucosidase" and "α-glucosidase" refer to an enzyme that catalyzes the hydrolysis of both an α(1,4) glycosidic linkage and an α(1,6) glycosidic linkage and liberates α-D-glucose units from the non-reducing end of oligosaccharides. A glucosidase has both amylolytic activity and isoamylolytic activity. Glucosidases include but are not limited to the group comprising IUBMB classification EC 3 2.1.3 (amyloglucosidase) and EC 3.2.1.20 (α-Glucosidases).

The term "α(1,6)-linked glucose oligosaccharide hydrolyzing enzyme" refers to an enzyme possessing the functional activity to catalyze the hydrolysis of an α(1,6) glycosidic linkage. Specific examples of an enzyme possessing such a functional activity include isoamylases, α-isoamylases, glucosidases, and α-glucosidases.

The term "isomaltase" or "oligo-(1,6)-glucosidase" or "dextrin 6-α-D-glucanohydrolase" refers to an enzyme (EC 3.2.1.10) that hydrolyzes only α(1,6)-linkages at the nonreducing end of oligosaccharides.

The term "DexB" refers to the (1,6)-α-glucosidase encoded by the dexB gene (GenBank Accession number M77351) of *Streptococcus mutans*, which releases glucose from the non-reducing ends of α(1,6)-linked isomaltosaccharides and dextran.

The term "limit dextrin" refers to the product of the amylolytic degradation of starch comprising monosaccharides and oligosaccharides. The action of amylase on amylopectin yields a mixture of monosaccharide (D-glucose), disaccharides (maltose, α(1,4) linked, and isomaltose, α(1,6) linked) and higher oligosaccharides. The higher oligosaccharides may be linear (contain exclusively α(1,4) linkages) or branched (contain predominantly α(1,4) linkages and α(1,6) linkages).

The term "degree of polymerization" or "DP" refers to the number of monomer units present in an individual component of a saccharide mixture; for example, a monosaccharide such as D-glucose has a DP of 1, a disaccharide such as maltose has a DP of 2, a trisaccharide such as panose has a DP of 3, etc. When applied to polysaccharide mixtures or oligosaccharide mixtures, DP refers to the average number of monomers per molecule.

The term "dextrose equivalent" ("DE") refers to the "reducing sugar content expressed as dextrose percentage on dry matter" as determined by the Lane-Eynon titration. (Handbook of Starch Hydrolysis Products and their Derivatives, M. W. Kearsely and S. Z. Dziedzic, eds., Blackie Academic & Professional, page 86). The DE scale indicates the degree of hydrolysis of starch, starch having a nominal value of 0 DE and the ultimate hydrolysis product having a value of 100 DE.

Amylase and isoamylase activity may be intracellular or extracellular. For the purposes of this invention, the term "intracellular activity" is meant to refer to enzymatic activity that can be observed with disrupted cells or cell extracts when provided substrate but not with intact cells when provided substrate extracellularly. The term "extracellular activity" is meant to refer to activity that is observed with intact cells (including growing cells) when provided substrate extracellularly. The inability of the enzyme substrates to passively diffuse or be actively transported into the cell is implied in the terms "intracellular activity" and "extracellular activity"

"Target molecule" refers to a biocatalytically-produced product. This may be a compound that is naturally produced by the biocatalyst or non-native genes may be genetically engineered into a microorganism for their functional expression in the biofermentation. "Target molecule" in this context also refers to any by-product of the biofermentation that would be desirable to selectively remove from the biofermentation system to eliminate feedback inhibition and/or to maximize biocatalyst activity.

"Volumetric productivity" refers to the mass of target molecule produced in a biofermentor in a given volume per time, with units of grams/(liter hour) (abbreviated g/(L hr)). This measure is determined by the specific activity of the biocatalyst and the concentration of the biocatalyst. It is calculated from the titer, run time, and the working volume of the biofermentor.

"Titer" refers to the target molecule concentration with units of grams/liter (abbreviated g/L).

The terms "polynucleotide" or "polynucleotide sequence", "oligonucleotide", "nucleic acid sequence", and "nucleic acid fragment" or "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, an "isolated nucleic acid molecule" or "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

As used herein, "substantially similar" refers to nucleic acid fragments wherein changes in one or more nucleotide bases results in substitution of one or more amino acids, but do not affect the functional properties of the polypeptide encoded by the nucleotide sequence. It is therefore understood that the invention encompasses more than the specific exemplary nucleotide or amino acid sequences and includes functional equivalents thereof. The terms "substantially similar" and "corresponding substantially" are used interchangeably herein.

Moreover, alterations in a nucleic acid fragment that result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes that result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%. The term "% identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity"and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 60% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein.

A "substantial portion" of an amino acid or nucleotide sequence comprises an amino acid or a nucleotide sequence that is sufficient to afford putative identification of the protein or gene that the amino acid or nucleotide sequence comprises.

Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J Mol. Biol.* 215:403-410; see also the explanation of the BLAST alogarithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" or "synthetic genes" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well-established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNAS-TAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

"Gene" refers to a nucleic acid fragment that expresses a specific protein, including regulatory sequences preceding (5' non-coding sequences) and following (3'non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "chimeric protein" is a protein encoded by a chimeric gene. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or chimeric genes. A "transgene" is a gene that has been introduced into the genome by a transformation procedure.

"Coding sequence" refers to a nucleotide sequence that codes for a specific amino acid sequence.

"Regulatory sequences" and "suitable regulatory sequence" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". It is further recognized that since in most cases the exact boundaries of regulatory sequences have not been completely defined, nucleic acid fragments of different lengths may have identical promoter activity.

Promoters which are useful to drive expression of the genes of the present invention in a desired host cell are numerous and familiar to those skilled in the art. Virtually any promoter capable of driving these genes is suitable for the present invention including but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*), *Streptomyces lividins* GI, as well as the amy, apr, and npr promoters and various phage promoters useful for expression in *Bacillus*.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

"3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. ((1989) *Plant Cell* 1:671-680).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to two or more nucleic acid fragments located on a single polynucleotide and associated with each other so that the function of one affects the function of the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Signal sequence" refers to a nucleotide sequence that encodes a signal peptide.

"Transformation" refers to the transfer of a nucleic acid fragment into a host organism or the genome of a host organism, resulting in genetically stable inheritance. Host organisms containing the transformed nucleic acid fragments are referred to as "recombinant", "transgenic" or "transformed" organisms. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal.

The terms "host cell" or "host organism" refer to a microorganism capable of receiving foreign or heterologous genes or multiple copies of endogenous genes and of expressing those genes to produce an active gene product.

The terms "DNA construct" or "construct" refer to an artificially constructed fragment of DNA. Such construct may be used by alone or may be used in conjunction with a vector.

The terms "plasmid", "vector" and "cassette" refer to an extra chromosomal element often carrying genes that are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements, in addition to the foreign gene, that facilitate transformation of a particular host cell. "Expression cassette" refers to a specific vector containing a foreign gene and having elements in addition to the foreign gene that allow for enhanced expression of that gene in a foreign host.

The terms "encoding" and "coding" refer to the process by which a gene, through the mechanisms of transcription and translation, produces an amino acid sequence. The process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences.

"PCR" or "polymerase chain reaction" is well known by those skilled in the art as a technique used for the amplification of specific DNA segments (U.S. Pat. Nos. 4,683,195 and 4,800,159).

"ORF" or "open reading frame" is a sequence of nucleotides in a DNA molecule that encodes a peptide or protein. This term is often used when, after the sequence of a DNA fragment has been determined, the function of the encoded protein is not known.

The term "fermentable carbon substrate" refers to a carbon source capable of being metabolized by host organisms of the present invention and particularly those carbon sources selected from the group consisting of monosaccharides, oligosaccharides, polysaccharides, and one-carbon substrates or mixtures thereof.

Isolation of Homologs

The nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction (PCR), Mullis et al., U.S. Pat. No. 4,683,202), ligase chain reaction (LCR), Tabor et al., *Proc. Acad. Sci.* USA 82,1074, (1985)), or strand displacement amplification (SDA, Walker et al., *Proc. Natl. Acad. Sci.* U.S.A., 89, 392, (1992)).

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33-50 IRL Press, Herndon, Va.); Rychlik, W. (1993) In White, B. A. (ed.), *Methods in Molecular Biology*, Vol. 15, pages 31-39, PCR Protocols: Current Methods and Applications. Humania Press, Inc., Totowa, N.J.)

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed.

Various hybridization solutions can be employed. Typically, these comprise from about 20 to 60% volume, preferably 30%, of a polar organic solvent. A common hybridization solution employs about 30-50% v/v formamide, about 0.15 to 1M sodium chloride, about 0.05 to 0.1 M buffers, such as sodium citrate, Tris-HCl, PIPES or HEPES (pH range about 6-9), about 0.05 to 0.2% detergent, such as sodium dodecylsulfate, or between 0.5-20 mM EDTA, FICOLL (Pharmacia Inc.) (about 300-500 kilodaltons), polyvinylpyrrolidone (about 250-500 kDal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents that include a variety of polar water-soluble or swellable agents, such as polyethylene glycol, anionic polymers such as polyacrylate or polymethylacrylate, and anionic saccharidic polymers, such as dextran sulfate.

Recombinant Expression—Microbial

The genes and gene products of the present sequences may be introduced into microbial host cells. Preferred host cells for expression of the instant genes and nucleic acid molecules are microbial hosts that can be found broadly within the fungal or bacterial families and which grow over a wide range of temperature, pH values, and solvent tolerances. Large scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of suitable host strains include but are not limited to fungal or yeast species such as *Aspergillus, Trichoderma, Saccharomyces, Pichia, Candida, Hansenula*, or bacterial species such as member of the proteobacteria and actinomycetes as well as the specific genera *Rhodococcus, Acinetobacter, Arthrobacter, Brevibacterium, Acidovorax, Bacillus, Streptomyces, Escherichia, Salmonella, Pseudomonas*, and *Cornyebacterium*.

*E. coli* is particularly well suited to use as the host microorganism in the instant invention fermentative processes. *E. coli* is not able to metabolize oligosaccharides containing an α(1,6) linkage and also has difficulty metabolizing any oligosaccharide of DP>7.

Microbial expression systems and expression vectors containing regulatory sequences that direct high level expression of foreign proteins are well known to those skilled in the art. Any of these could be used to construct chimeric genes to produce the any of the gene products of the instant sequences. These chimeric genes could then be introduced into appropriate microorganisms via transformation techniques to provide high-level expression of the enzymes.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene harboring transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of gene products. Termination control regions may also be derived from various genes native to the preferred hosts. Optionally, a termination site may be unnecessary, however, it is most preferred if included.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences.

Enzymes having Enhanced Activity

It is contemplated that the present sequences may be used to produce gene products having enhanced or altered activity. Various methods are known for mutating a native gene sequence to produce a gene product with altered or enhanced activity including but not limited to error prone PCR (Melnikov et al., *Nucleic Acids Research*, (Feb. 15, 1999) Vol. 27, No. 4, pp. 1056-1062); site directed mutagenesis (Coombs et al., *Proteins* (1998), 259-311, 1 plate. Editor(s): Angeletti, Ruth Hogue. Publisher: Academic, San Diego, Calif.) and "gene shuffling" (U.S. Pat. No. 5,605,793; U.S. Pat No. 5,811,238; U.S. Pat. No. 5,830,721; and U.S. Pat. No. 5,837,458, incorporated herein by reference).

Pathway Modulation

Knowledge of the sequence of the present genes will be useful in manipulating the sugar metabolism pathways in any organism having such a pathway. Methods of manipulating genetic pathways are common and well known in the art. Selected genes in a particularly pathway may be up-regulated or down-regulated by variety of methods. Additionally, competing pathways organism may be eliminated or sublimated by gene disruption and similar techniques.

Once a key genetic pathway has been identified and sequenced specific genes may be up-regulated to increase the output of the pathway. For example, additional copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may be used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565,350; Zarling et al., PCT/US93/03868).

Within the context of the present invention it may be useful to modulate the expression of the sugar metabolism pathway by any one of a number of well-known methods (e.g., antisense, radiation- or chemically-induced mutations, geneshuffling, etc.). For example, the present invention provides a number of genes encoding key enzymes in the sugar metabolism pathway leading to the production of simple sugars. The isolated genes include the α-glucosidase and isomaltase genes. Where, for example, it is desired to accumulate glucose or maltose, any of the above methods may be employed to overexpress the α-glucosidase and isomaltase genes of the present invention. Similarly, biosynthetic genes' accumulation of glucose or maltose may be effected by the disruption of down stream genes such as those of the glycolytic pathway by any one of the methods described above.

Biofermentations

The present invention is adaptable to a variety of biofermentation methodologies, especially those suitable for large-scale industrial processes. The invention may be practiced using batch, fed-batch, or continuous processes, but is preferably practiced in fed-batch mode. These methods of biofermentation are common and well known in the art (Brock, T. D.; *Biotechnology: A Textbook of Industrial Microbiology*, 2nd ed.; Sinauer Associates: Sunderland, Mass. (1989); or Deshpande, *Appl. Biochem. Biotechnol.* 36:227 (1992)).

"Biofermentation system" or "biofermentation" refers to a system that uses a biocatalyst to catalyze a reaction between substrate(s) and product(s).

The Biocatalyst

The biocatalyst initiates or modifies the rate of a chemical reaction between substrate(s) and product(s). The biocatalyst may be whole microorganisms or in the form of isolated enzyme catalysts. Whole microbial cells can be used as a biocatalyst without any pretreatment such as permeabilization. Alternatively, the whole cells may be permeabilized by methods familiar to those skilled in the art (e.g., treatment with toluene, detergents, or freeze-thawing) to improve the rate of diffusion of materials into and out of the cells.

Microorganisms useful in the present invention may include, but are not limited to, bacteria (such as the enteric bacteria *Escherichia* and *Salmonella*, for example, as well as *Bacillus, Acinetobacter, Streptomyces, Methylobacter, Rhodococcus*, and *Pseudomonas*); cyanobacteria (such as *Rhodobacter* and *Synechocystis*); yeasts (such as *Saccharomyces, Zygosaccharomyces, Kluyveromyces, Candida, Hansenula, Debaryomyces, Mucor, Pichia*, and *Torulopsis*); filamentous fungi (such as *Aspergillus* and *Arthrobotrys*); and algae. For purposes of this application, "microorganism" also encompasses cells from insects, animals, or plants.

Culture Conditions

Materials and methods suitable for maintenance and growth of microbial cultures are well known to those in the art of microbiology or biofermentation science art (Bailey and Ollis, *Biochemical Engineering Fundamentals*, $2^{nd}$ Edition; McGraw-Hill: NY (1986)). Consideration must be given to appropriate media, pH, temperature, and requirements for aerobic, microaerobic, or anaerobic conditions, depending on the specific requirements of the microorganism for the desired functional gene expression.

Media and Carbon Substrates

Biofermentation media (liquid broth or solution) for use in the present invention must contain suitable carbon substrates, chosen in light of the needs of the biocatalyst. Suitable substrates may include, but are not limited to, monosaccharides (such as glucose and fructose), disaccharides (such as lactose or sucrose), oligosaccharides and polysaccharides (such as starch or cellulose or mixtures thereof), or unpurified mixtures from renewable feedstocks (such as cheese whey permeate, cornsteep liquor, sugar beet molasses, and barley malt). The carbon substrate may also be one-carbon substrates (such as carbon dioxide, methanol, or methane).

In addition to an appropriate carbon source, biofermentation media must contain suitable minerals, salts, vitamins, cofactors, buffers, and other components, known to those skilled in the art (Bailey and Ollis, *Biochemical Engineering*

Fundamentals, 2$^{nd}$ ed; pp 383-384 and 620-622; McGraw-Hill: New York (1986)). These supplements must be suitable for the growth of the biocatalyst and promote the enzymatic pathway necessary to produce the biofermentation target product.

Finally, functional genes that express an industrially useful product may be regulated, repressed, or derepressed by specific growth conditions (for example, the form and amount of nitrogen, phosphorous, sulfur, oxygen, carbon or any trace micronutrient including small inorganic ions). The regulation of functional genes may be achieved by the presence or absence of specific regulatory molecules (such as gratuitous inducers) that are added to the culture and are not typically considered nutrient or energy sources. Growth rate may also be an important regulatory factor in gene expression.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

The meaning of abbreviations is as follows: "h" means hour(s), "min" means minute(s), "sec" means second(s), "d" means day(s), "mL" means milliliter(s), "L" means liter(s), "mM" means millimolar, "nm" means nanometer, "g" means gram(s), and "kg" means kilogram(s), "HPLC" means high performance liquid chromatography, "RI" means refractive index.

General Methods:

Materials and methods suitable for the maintenance and growth of bacterial cultures are well known in the art. Techniques suitable for use in the following examples may be found as set out in *Manual of Methods for General Bacteriology*; Phillipp Gerhardt, R. G. E. Murray, Ralph N. Costilow, Eugene W. Nester, Willis A. Wood, Noel R. Krieg and G. Briggs Phillips, Eds., American Society for Microbiology: Washington, D.C. (1994) or in *Biotechnology: A Textbook of Industrial Microbiology*; Brock, T. D., 2$^{nd}$ ed.; Sinauer Associates: Sunderland, Mass. (1989).

The conversion of glycerol to 1,3-propanediol was monitored by HPLC. Analyses were performed using standard techniques and materials available to one of skill in the art of chromatography. One suitable method utilized a Waters Maxima 820 HPLC system using UV (210 nm) and RI detection. Samples were injected onto a Shodex SH-1011 column (8 mm×300 mm, purchased from Waters, Milford, Mass.) equipped with a Shodex SH-1011 P precolumn (6 mm×50 mm), temperature controlled at 50° C., using 0.01 N H$_2$SO$_4$ as mobile phase at a flow rate of 0.5 mL/min. When quantitative analysis was desired, samples were prepared with a known amount of trimethylacetic acid as external standard. Typically, the retention times of glucose (RI detection), glycerol, 1,3-propanediol (RI detection), and trimethylacetic acid (UV and RI detection) were 15.27 min, 20.67 min, 26.08 min, and 35.03 min, respectively.

Example 1

Genome Sequencing of Bifidobacterium breve ATCC 15700

*Bifidobacterium breve* (ATCC 15700) was purchased from the American Type Culture Collection, P.O. Box 1549, Manassas, Va. 20108, U.S.A. A cell pellet was obtained and suspended in a solution containing 10 mM Na-EDTA and 50 mM Tris-HCl, pH 7.5. Genomic DNA was isolated from *Bifidobacterium breve* (ATCC 15700) according to standard protocols. Genomic DNA and library construction were prepared according to published protocols (Fraser et al., *Science* 270 (5235):397-403 (1995)).

Genomic DNA preparation: After suspension, the cells were gently lysed in 0.2% sarcosine, 20 mM beta-mercaptoethanol, and 150 units/mL of Lyticase and incubated for 30 min at 37° C. DNA was extracted twice with Tris-equilibrated phenol and twice with chloroform. DNA was precipitated in 70% ethanol and suspended in a solution containing 1 mM Na-EDTA and 10 mM Tris-HCl, pH 7.5. The DNA solution was treated with a mix of RNAases, then extracted twice with Tris-equilibrated phenol and twice with chloroform. This was followed by precipitation in ethanol and suspension in 1 mM Na-EDTA and 10 mM Tris-HCl, pH 7.5.

Library construction: 50 to 100 μg of chromosomal DNA was suspended in a solution containing 30% glycerol, 300 mM sodium acetate, 1 mM Na-EDTA, and 10 mM Tris-HCl, pH 7.5 and sheared at 12 psi for 60 sec in an Aeromist Downdraft Nebulizer chamber (IBI Medical products, Chicago, Ill.). The DNA was precipitated, suspended and treated with BAL-31 nuclease. After size fractionation on a low melt agarose gel, a fraction (2.0 kb or 5.0 kb) was excised, cleaned, and ligated to the phosphatased SmaI site of pUC18 (Amersham Biosciences) using T4 DNA ligase (New England Biolabs, Inc., Beverly, Mass.). The ligation mix was run on a gel and the DNA band representing the vector plus one insert ligation product was excised, treated with T4 DNA polymerase (New England Biolabs), and then religated. This two-step ligation procedure was applied to produce a high titer library with greater than 99% single inserts.

Sequencing: A shotgun sequencing strategy approach was adopted for the sequencing of the whole microbial genome (Fleischmann, R. et al., *Science* 269(5223):496-512 (1995)). Sequence was generated on an ABI Automatic sequencer (Applied Biosystems, Foster City, Calif.) using dye terminator technology (U.S. Pat. No. 5,366,860; EP 272,007) using a combination of vector and insert-specific primers. Sequence editing was performed in either DNAStar (DNA Star Inc., Madison, Wis.) or the Wisconsin GCG program (Wisconsin Package Version 9.0, Genetics Computer Group (GCG), Madison, Wis.) and the CONSED package (version 7.0). All sequences represent coverage at least two times in both directions. Sequence assembly was performed using the Phred/Phrap software package (version 0.961028. m/0.990319).

Example 2

Identification of Carbohydrate Degradation Genes

Genes encoding isoamylase activity were identified by conducting BLAST (Basic Local Alignment Search Tool; Altschul et al., *J. Mol. Biol.* 215:403-410 (1993); see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The sequences obtained were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTP algorithm (Gish and States, *Nature Genetics* 3:266-272 (1993)) provided by the NCBI.

All comparisons were done using either the BLASTN or BLASTP algorithm. The results of the BLAST comparison are presented in Table 1, which summarizes the sequences to which they have the most similarity. Table 1 displays data based on the BLASTP algorithm with values reported in expectation values. The expectation value (E-value) is the number of different alignments with scores equivalent to or better than a particular score S that are expected to occur in a database search by chance. The lower the E-value, the more significant the score.

(Qiagen, Valencia, Calif.). Reactions contained 1 ng of genomic DNA and 1 µM each of primers. The resulting 1.6 kb DNA fragment was digested with the enzymes BamHI and SalI. The digested fragment was cloned directly into the plasmid pTRC99a (amp$^R$) (Amersham-Pharmacia, Amersham, UK) resulting in a translational fusion with the LacZ gene. The plasmid, designated pTRC99-dexB, also contains the coding sequence for the first 10 amino acids of the LacZ gene, which upon expression are fused to the N-terminal end of native DexB protein. pTRC99-dexB plasmid was transformed into *E. coli* DH5α cells using the manufacturer's protocol (Invitrogen, Carlsbad, Calif.) and plated on Luria Broth (LB) medium containing 100 µg/mL ampicillin.

Isoamylase activity was assessed from crude protein extract following expression in *E. coli*. A single colony of *E. coli* DH5α/pTRC99-dexB was cultured overnight in LB medium and then diluted 1:100 into fresh LB medium (3.0 mL) and cultured for an additional two hr at 37° C. Following this incubation, the DexB gene was induced by adding isopropyl β-D-1-thiogalactopyranoside (IPTG) to a final concentration of 1 mM. Crude protein was extracted from induced cells following an additional two hr incubation. To isolate the crude protein extract, cells were collected by centrifugation (1×8000 g) and then suspended in 0.5 mL of

TABLE 1

| Clone Name | Similarity Identified | SEQ ID | SEQ ID | % Identity[a] | % Similarity[b] | E-value[c] | Citation |
|---|---|---|---|---|---|---|---|
| mbc1g.pk007.h12 *Bifidobacterium breve* | (AF411186) alpha-glucosidase [*Bifidobacterium adolescentis*] | 1 | 2 | 61 | 70 | 0.0 | Van den Broek, L. A. M. et al. "Cloning and characterization of two alpha-glucosidases from *Bifidobacterium adolescentis*" NCBI database |
| Mbc2g.pk018.j20 *Bifidobacterium breve* | (AF358444) alpha-glucosidase [*Bifidobacterium adolescentis*] | 3 | 4 | 73 | 84 | 0.0 | Van den Broek, L. A. M. et al. "Cloning and characterization of two alpha-glucosidases from *Bifidobacterium adolescentis*" NCBI database |
| mbc1g.pk026.k1 *Bifidobacterium breve* | (AF358444) alpha-glucosidase [*Bifidobacterium adolescentis*] | 5 | 6 | 69 | 82 | 0.0 | Van den Broek, L. A. M. et al. "Cloning and characterization of two alpha-glucosidases from *Bifidobacterium adolescentis*" NCBI database |
| DexB *Steptococcus mutans* | (M77351) dextran glucosidase [*Streptococcus mutans*] | 16 | 17 | 100 | 100 | 0.0 | Russell, R. R. and Ferretti, J. J. "Nucleotide sequence of the dextran glucosidase (dexB) gene of *Streptococcus mutans*" J. Gen. Microbiol. 136 (Pt 5), 803-810 (1990) |

[a]% Identity is defined as percentage of amino acids that are identical between the two proteins.
[b]% Similarity is defined as percentage of amino acids that are identical or conserved between the two proteins.
[c]Expectation value. The Expectation value estimates the statistical significance of the match, specifying the number of matches, with a given score, that are expected in a search of a database of this size absolutely by chance.

Example 3

Intracellular Isoamylase Activity in *E. coli* Containing the *Streptococcus mutans* dexB Gene For cloning of the dexB gene, genomic DNA was isolated from *Streptococcus mutans* (ATCC 25175D) using the protocol described in Jagusztyn et al. (*J. Gen. Microbiol.* 128: 1135-1145(1982)).

Oligonucleotide primers (SEQ ID NO:7 and SEQ ID NO:8) were designed based on *Streptococcus mutans* (dexB) DNA sequence (Ferretti et al., *Infection and Immunity* 56:1585-1588 (1988)) and also included BamHI and SalI restriction sites. The dexB gene was amplified using the standard PCR protocol included with the HotStartTaq™ kit phosphate buffer (10 mM, pH 6.8). The suspension was sonicated to release total cellular protein and centrifuged (1×14,000 g) to remove cell debris. Total protein present in the supernatant was assayed for isoamylase activity by incubation with isomaltose or separately with panose at 37° C. in 10 mM phosphate buffer (pH 6.8) for two hrs. Products of the reaction were characterized by High Performance Anion Exchange Chromatography (HPAEC).

For HPAEC, samples were prepared and analyzed in the following manner. After the two-hr incubation with isomaltose or panose, total protein extracts were filtered through a 0.22 µM Spin-X (R) centrifuge tube filter (Costar, Corning, N.Y.) and diluted with sterile filtered water. Samples were analyzed by HPAEC (Dionex, Sunnyvale, Calif.) using a PA10 column, 100 mM sodium hydroxide as the eluent and a 0-150 mM sodium acetate linear gradient. Results demonstrating degradation of isomaltose using pTRC99-dexB cell-extract are listed in Table 2. Degradation of panose, and the products formed by incubation with pTRC99-dexB cell-extract are listed in Table 3.

TABLE 2

Activity of DexB Crude Protein Extract with Isomaltose (250 μg/mL)

| Cell Line | Isomaltose (μg/mL) |
| --- | --- |
| DH5α/pTRC99a (negative control) | 256 |
| DH5α/pTRC99-dexB | ND |

ND = not detected

TABLE 3

Activity of DexB Crude Protein Extracts with Panose (150 μg/mL)

| Cell Line | Panose (μg/mL) | Maltose (μg/mL) | Isomaltose (μg/mL) | Glucose (μg/Ml) |
| --- | --- | --- | --- | --- |
| DH5α/pTRC99a (negative control) | 122 | ND | ND | ND |
| DH5α/pTRC99-dexB | ND | 74 | 8 | 82 |

ND = not detected

Example 4

Expression of the *Bifidobacterium breve* Isoamylolytic Genes in *E. Coli*

Several open reading frames from the Bifidobacterium breve (ATCC 15700) library were identified as putative candidate genes with activity against α(1,6)-linked glucose oliogosaccharides (Example 2). Three putative clones, mbc1g.pk007.h12 (h12), mbc1g.pk026.k1 (k1), and mbc2g.pk018.j20(j20) were chosen for detailed characterization of isoamylolytic activity, using oligosaccharides containing α(1,6)-linked glucose.

*E. coli* DH5α strains containing the cloned full length coding sequence of the putative isoamylolytic *Bifidobacterium* genes in pUC18 from Example 1 were inoculated to LB medium and cultured at 37° C. The culture was diluted after 20 hr (1:100) in fresh LB medium and incubated for an additional 3-4 hr at 37° C. Total protein extract was prepared from cells as described in Example 3. Total protein present in the supernatant was assayed for isoamylolytic activity by incubation with isomaltose or separately with panose at 37° C. in 10 mM phosphate buffer (pH 6.8) for two hr. Samples were prepared and products of the reaction were characterized by High Performance Anion Exchange Chromatography (HPAEC) as described in Example 3. Results demonstrated that the enzymes produced from clones h12, k1, and j20 degraded isomaltose to glucose (Table 4).

TABLE 4

Activity of *B. breve* crude extracts with Isomaltose (150 μg/mL)

| Cell line | Isomaltose (μg/mL) | Glucose (μg/mL) |
| --- | --- | --- |
| DH5α/pUC18 (negative control) | 107 | 37 |
| DH5α - h12 | 6 | 187 |
| DH5α - k1 | 5 | 165 |
| DH5α - j20 | 8 | 154 |

ND = not detected

Total protein extracts were incubated with panose (250 μg/mL) for two hr and then filtered through a 0.22 μM Spin-X (R) centrifuge tube filter (Costar, Corning, N.Y.). Samples were analyzed by HPAEC as described in Example 3. The absence of panose following incubation demonstrated that the enzymes produced from the clones h12, k1 and j20 are capable of degrading panose. FIG. 1 shows that the clone h12 degrades panose completely to glucose (also shown is the negative control, plasmid pUC18 in *E. coli* DH5α). FIG. 1 also shows that the enzymes from the k1 and j20 clones degrade panose to glucose and maltose.

Example 5

Expression of the native *B. breve* j20 Isoamylase gene in *E. coli*

The native *Bifidobacterium breve* gene j20 (obtained in Example 1) appeared to have a signal peptide at the NH-end of the mature coding sequence (determined by pSort prediction software; Nakai and Kanehisa, Expert, PROTEINS: *Structure, Function, and Genetics* 11:95-110 (1991)). The nucleic and amino acid sequences for the *Bifidobacterium breve* j20 gene, which codes for an α(1,6)-linked glucose oligosaccharide hydrolyzing activity, are SEQ ID NO:30 SEQ ID NO:31, respectively.

Metabolism of isomaltose was, therefore, attempted using intact whole cells. This was accomplished by culturing a single colony of *E. coli* DH5α cells expressing the j20 gene in LB medium containing isomaltose (500 μg/mL) at 37° C. for 24 hr. Following incubation, cells were removed from the medium, and the medium was prepared and analyzed by HPAEC methods described in Example 3. The presence of extracellular isoamylase activity in cells expressing the *B. breve* j20 gene was demonstrated by reduced levels of isomaltose compared to the negative control (*E. coli* DH5α cells containing only the original pUC18 plasmid). The results in Table 5 demonstrate that *E. coli* cells expressing the native j20 gene degraded isomaltose supplied extracellularly.

TABLE 5

Isomaltose Metabolized by the Native j20 Gene

| Cell line | Isomaltose (μg/mL) | Glucose (μg/mL) |
| --- | --- | --- |
| DH5α/pUC18 (negative control) | 508 | 26 |
| DH5α - j20 | 180 | 22 |

Example 6

Extracellular Targeting of the *S. mutans* dexB and *B. breve* Isoamylase Enzymes Because the *Bifidobacterium breve* k1 and *Streptococcus mutans* dexB genes do not appear to contain native signal peptides (pSort prediction software; Nakai and Kanehisa, Expert, PROTEINS: *Structure, Function, and Genetics* 11:95-110 (1991)), the mature coding sequences were linked in a translational fusion to signal peptides by PCR methods, allowing extracellular expression.

Modular expression vectors containing the *Bacillus subtilis* alkaline and neutral protease genes were constructed in a series of steps beginning with the plasmids pBE505 (Borchert and Nagarajan, *J. Bacteriol.* 173:276-282 (1991)) and pBE311 (Nagarajan and Borchert, *Res. Microbiol.* 142:787-792 (1991)). The plasmids were digested with the restriction enzymes KpnI and NruI. The resulting 969 bp KpnI-NruI fragment from pBE505 was isolated and ligated into the large 7.2 kb KpnI-NruI fragment from pBE311, resulting in pBE559.

Plasmids pBE559 and pBE597 (Chen and Nagarajan, *J. Bacteriol.* 175:5697-5700 (1993)) were then digested with the restriction enzymes KpnI and EcoRV. The 941 bp KpnI-EcoRV fragment from pBE559 was ligated into the 8.9 kb KpnI-EcoRV fragment from pBE597, resulting in plasmid pBE592.

Plasmid pBE26 (Ribbe and Nagarajan, *Mol. Gen. Genet.* 235:333-339 (1992)) was used as a template to amplify the *B. amyloliquefaciens* alkaline protease (apr) promoter region using PCR methods described in Example 3. The oligonucleotide primer SEQ ID NO:9 was designed and synthesized to introduce an NheI restriction site at the alkaline protease signal cleavage site and an EcoRV restriction site immediately downstream of the cleavage site. The oligonucleotide primer SEQ ID NO:10 was designed to anneal to the 5' polylinker region upstream of the apr promoter region in pBE26. A PCR reaction was carried out using the described primers and plasmid pBE26 template DNA. The resulting 1.2 kb PCR product was digested with KpnI and EcoRV and ligated into the large KpnI-EcoRV fragment from pBE592, resulting in pBE92.

Plasmid pBE80 (Nagarajan et al., *Gene* 114:121-126 (1992)) was used as a template to amplify the *B. amyloliquefaciens* neutral protease (npr) promoter region using PCR methods described in Example 3. The downstream primer SEQ ID NO:11 was designed and synthesized to introduce an NheI restriction site at the neutral protease signal cleavage site and an EcoRV restriction site immediately downstream of the cleavage site. The primer SEQ ID NO:12 was designed to anneal to the 5' region of the Npr promoter in pBE80. A PCR reaction was carried out using the described primers and DNA template. The resulting 350 bp PCR product was enzymatically digested with KpnI and EcoRV and ligated into the large KpnI-EcoRV fragment from pBE592, resulting in pBE93.

A translational fusion of the k1 and dexB genes to signal peptides of the *Bacillus subtilis* alkaline and neutral protease genes in the vectors pBE92 and pBE93 was accomplished using oligonucleotide primers described in Table 6. PCR amplfication was performed by the protocol described in Example 3, using genomic DNA from *Bifidobacterium breve* (ATCC 15700) or pTRC99-dexB plasmid, respectively, as a template.

Oligonucleotide primers SEQ ID NO:14 and SEQ ID NO:15, engineered with NheI and BamHI sites, were used to amplify a 1.8 kb k1 gene DNA fragment. Oligonucleotide primers SEQ ID NO:13 and SEQ ID NO:8, containing NheI and SalI restriction enzyme sites, resulted in amplification of a 1.6 kb dexB gene DNA fragment. The fragments were digested with the appropriate enzymes and cloned into modular vectors pBE92 and pBE93.

The resulting plasmids (designated pBE92-dexB, pBE93-dexB, pBE92-k1, and pBE93-k1, respectively) contained the native enzyme linked in a translational fusion to the signal peptide such that the signal peptide cleavage site (Ala Ser Ala) was conserved. Nucleic and amino acid sequences for the *Bacillus subtilis* neutral protease signal peptide linked to the *Bifidobacterium breve* k1 gene are SEQ ID NOs:40 and 41, respectively. Nucleic and amino acid sequences for the *Bacillus subtilis* neutral protease signal peptide linked to the *Streptococcus mutans* dexB gene are SEQ ID NOs:42 and 43, respectively. The plasmids were transformed into *E. coli* DH5α cells using the manufacturer's protocol (Invitrogen, Carlsbad, Calif.) and plated on Luria Broth (LB) medium containing ampicillin (100 μg/mL).

Characterization of activity in *E. coli* DH5α cells containing the pBE93 (negative control), pBE93-dexB or pBE93-k1 plasmid was carried out by inoculating 3.0 mL of LB medium containing ampicillin (100 μg/mL) and isomaltose (0.250 mg/mL). The cells were grown at 37° C. for 20 hr. Following incubation, cells were removed from the medium and prepared and analyzed by methods described in Example 3. The presence of extracellular isoamylase activity in cells containing the pBE93, pBE93-dexB or pBE93-k1 plasmid was demonstrated by reduced levels of isomaltose compared to the negative control (*E. coli* DH5α cells containing only the original pBE92 plasmid). The results in Table 6 demonstrate that the Npr-gene fusion proteins degraded isomaltose supplied extracellularly.

TABLE 6

DexB and K1 Extracellular Fusion Protein Activity in *E. coli* DH5α cells

| Cell line | Isomaltose (μg/mL) |
|---|---|
| pBE93 (negative control) | 215 |
| pBE93-dexB (isolate 4) | 117 |
| pBE93-dexB (isolate 8) | 89 |
| pBE93-k1 (isolate 7) | 76 |
| pBE93-k1 (isolate 8) | 74 |
| pBE93-k1 (isolate 9) | 62 |

*E. coli* DH5α cells containing the pBE93-dexB or pBE93-k1 plasmids degraded isomaltose; however, cell growth in minimal media containing isomaltose as the sole carbon source is a much more stringent measure of isoamylase activity. Therefore pBE93-dexB and pBE93-k1 plasmids were transformed into the *E. coli* strain FM5. The FM5 strain, unlike DH5α, has the ability to grow in a minimal medium, containing only salts and trace metals in addition to a carbon source (Maniatis et al. (1982) Molecular Cloning; a Laboratory Manual. Cold Spring Harbor Laboratory, Cold Spring Harbor, N.Y; Neidhardt (1987) *Escherichia coli* and *Salmonella typhimurium*, ASM Press, Washington, D.C.). Native FM5 cells, like the DH5α strain, cannot utilize isomaltose as a carbon source. To confirm this, FM5 cells transformed with the plasmid pBE93 were inoculated into M9 media (Maniatis et al., supra; Neidhardt, supra) containing either glucose (1 mg/mL) or isomaltose (1 mg/mL) and incubated at 37° C. for at least 20 hr. Cell growth was observed after 20 hr in flasks containing glucose, but not in flasks containing isomaltose, even after a 60 hr incubation.

In contrast to the negative control, FM5 cells containing the Npr-DexB and Npr-k1 fusion proteins (pBE93-dexB and pBE93-k1, respectively) grew well in M9 medium containing isomaltose following a 20 hr incubation period. For this experiment FM5/pBE93, FM5/pBE93-dexB and FM5/pBE93-k1 strains were inoculated into 2.0 mL M9 medium supplemented with either glucose or isomaltose (1 mg/mL) as the sole carbon source. The results, shown in Table 7, indicated that when the dexB or k1 genes, are linked in a translational fusion to the Npr signal peptide, are expressed in Fm5 cells, isomaltose is metabolized and supports cell growth.

TABLE 7

DexB and K1 Extracellular Fusion Protein Activity in *E. coli* FM5 cells

| Cell line | Isomaltose (μg/mL) |
|---|---|
| pBE93 (negative control) | 1091 |
| pBE93-dexB (isolate 2) | 319 |
| pBE93-dexB (isolate 15) | 197 |
| pBE93-dexB (isolate 3) | 183 |
| pBE93-k1 (isolate 5) | 34 |
| pBE93-k1 (isolate 4) | 20 |
| pBE93-k1 (isolate 3) | 17 |

Example 7

Expression of the Npr-dexB and Npr-k1 Fusion Genes in *E. coli* Leads to Increased Synthesis of Various Fermentation Products The ability of production hosts to metabolize oligosaccharides containing α(1,6)-linked glucose residues may increase the yield of a fermentation product when a mixture of sugars is supplied as the carbon source. The ability of the Npr-dexB and Npr-k1 fusion proteins to degrade α(1,6)-linkages was tested by first transforming the plasmids pBE93-dexB and pBE93-k1 into a cell line engineered to produce glycerol.

One microgram of plasmid DNA was used to transform *E. coli* strain RJ8n (ATCC PTA-4216), which also contained the plasmid pSYCO101 (spec$^R$) (described in U.S. patent application Ser. No. 10/420,587 herein incorporated by reference), which encodes the DARB1 and GPP2 genes from *Saccharomyces cerevisiase*, and dhaB and orf operons from *Klebsiella pnuemoniae*. The transformed *E. coli* strain produces glycerol from glucose as well as 1,3-propanediol when vitamin B12 is added. Methods for the production of glycerol and 1,3-propanediol from glucose are described in detail in U.S. Pat. No. 6,358,716 and U.S. Pat. No. 6,013,494 herein incorporated by reference. The transformed RJ8n cells were plated on LB medium containing 50 μg/mL spectinomycin and 100 μg/mL ampicillin. Single colonies were used to inoculate 2.0 mL of TM2 medium (potassium phosphate, 7.5 g/L; citric acid, 2.0 g/L; ammonium sulfate, 3.0 g/L; magnesium sulfate, 2.0 g/L; calcium chloride, 0.2 g/L; ferric ammonium citrate, 0.33 g/L; yeast extract (Difco-BD, Sparks, Md.) 5.0 g/L; trace elements (zinc sulfate, copper sulfate, cobalt chloride, manganese sulfate, ferric sulfate, sodium chloride); ammonium hydroxide, pH to 6.5; also containing glucose or isomaltose (1 mg/mL). Cultures were grown for 24 hr at 37° C. Cells were prepared and analyzed by methods described in Example 3.

Glycerol was shown to accumulate when *E. coli* RJ8n cells containing only the plasmid pSYCO101 were cultured for 24 hr at 37° C. in TM2 medium with glucose as the carbon source (Table 8). However, this negative control line produced negligible levels of glycerol when isomaltose was substituted for glucose in the medium, demonstrating that α(1,6)-linked glucose does not support accumulation of a fermentation product. By contrast, glycerol was produced in *E. coli* RJ8n containing the plasmids pSYCO101 and pBE93-dexB or pBE93-k1 when either isomaltose or glucose was provided as sole carbon sources (Table 8). When isomaltose was used as a carbon source, glycerol production was shown to be 8 to 9 times higher in *E. coli* RJ8n containing both the pBE93-dexB and pSYCO101 plasmids as compared to the negative control line, RJ8n containing only pSYCO101. Glycerol accumulation, using isomaltose, was 6 to 10 times higher in lines containing pSYCO101 and pBE93-k1 as compared to the negative control. The data in Table 8 demonstrate that expression of the Npr-dexB or Npr-k1 genes resulted in glycerol production in cultures supplied with isomaltose. The data further demonstrate that levels of product accumulated were comparable for cultures containing the fusion proteins regardless of whether the carbon source was glucose or isomaltose.

TABLE 8

Glycerol Accumulation Due to Expression of Npr-DexB or Npr-K1

| | Glycerol Accumulated (μg/mL) | |
|---|---|---|
| Cell line | Glucose-supplied cultures | Isomaltose-supplied cultures |
| RJ8n/pSYCO101 | 430 | 39 |
| RJ8n/pSYCO101/pBE93-dexB (isolate 4) | 381 | 362 |
| RJ8n/pSYCO101/pBE93-dexB (isolate 8) | 353 | 354 |
| RJ8n/pSYCO101/pBE93-k1 (isolate 2) | 383 | 401 |
| RJ8n/pSYCO101/pBE93-k1 (isolate 6) | 412 | 226 |

The capability of *E. coli* line RJ8n containing the plasmids pSYCO101 and pBE93-k1 to produce fermentation products using α(1,6)-linked glucose as a substrate was further characterized by culturing in TM2 medium containing panose (1 mg/mL) and comparing the results to the same line using glucose as a substrate (1 mg/mL).

Data in Table 9 also show that *E. coli* strain RJ8n containing only the plasmid pSYCO101 (negative control) does not synthesize glycerol when panose is supplied as the sole carbohydrate source in TM2 medium. However, glycerol is produced when the plasmid pBE93-k1 is present in this same strain and cultured in TM2 medium with panose. Glycerol accumulation in *E. Coli* RJ8n containing the plasmids pSYCO101 and pBE93-k1 was comparable when either glucose or panose was supplied as a carbohydrate source.

TABLE 9

Glycerol Accumulation Due to Expression of Npr-K1

| | Glycerol Accumulated (μg/mL) | |
|---|---|---|
| Cell line | Glucose-supplied cultures | Isomaltose-supplied cultures |
| RJ8n/pSYCO101 | 417 | 25 |
| RJ8n/pSYCO101/pBE93-k1 (9) | 396 | 363 |
| RJ8n/pSYCO101/pBE93-k1 (7) | 376 | 347 |

The data above demonstrate that expression of the Npr-dexB or Npr-k1 fusion protein in *E. coli* results in increased production of glycerol when isomaltose or panose represents the sole carbohydrate source in the medium. Demonstrating that this result is not limited to glycerol production alone was accomplished by synthesis of another fermentation product (1,3-propanediol) using the same fusion protein expression system.

RJ8n cells transformed with the plasmids pSYCO101 and pBE93-dexB or pBE93-k1 were used to inoculate 2.0 mL of TM2 medium (described above) also containing glucose (1 mg/mL) or isomaltose (1 mg/mL) and vitamin B12 (100 ng/L). Cultures were grown for 20 hr at 37° C. Cells were prepared and analyzed by methods described in Example 3.

The data in Table 10 demonstrate that 1,3-propanediol was not synthesized by the negative control line (RJ8n/pSYCO101) when grown in media containing only isomaltose as a carbohydrate source. However, when either the Npr-dexB or Npr-k1 fusion protein was expressed in RJ8n cells, isomaltose was shown to be metabolized. This resulted in accumulation of the fermentation product 1,3-propanediol. The data further demonstrate that the level of 1,3-propanediol synthesized by RJ8n cells expressing the Npr-dexB or Npr-K1 fusion protein was comparable whether glucose or isomaltose was supplied as the sole carbohydrate.

TABLE 10

1,3-Propanediol Accumulation Due to Expression of Npr--dexB or Npr-k1

| | 1,3-Propanediol (mg/mL) | | |
|---|---|---|---|
| Cell line | Glucose-supplied cultures | Isomaltose-supplied cultures | Isomaltose (µg/mL) |
| RJ8n/pSYCO101 | 2.8 | ND | 1225 |
| RJ8n/pSYCO101/pBE93-k1 (9) | 1.7 | 2.8 | 12 |
| RJ8n/pSYCO101/pBE93-k1 (7) | 3.0 | 2.9 | 14 |
| RJ8n/pSYCO101/pBE93-dexB | 3.0 | 3.1 | 27 |

ND = not detected

Example 8

Expression of the *B. breve* k1 Gene in *E. coli* Using an Alternative Promoter

The use of alternative promoters to direct expression of a preferred gene is often highly desirable. Alternative promoters may be used to vary the level or timing of gene expression and, therefore, increase utilization of a preferred substrate.

Effective expression of the *B. breve* k1 isoamylase gene using an alternative promoter was demonstrated by replacing the neutral protease promoter in the plasmid pBE93 -k1 (Example 6) with a glucose isomerase (GI) promoter and variant of the GI-promoter. Isolation of the *Streptomyces lividins* GI-promoter and creation of the variant promoter was disclosed in U.S. patent application Ser. No. 10/420,587. Prior to replacing the NPR-promoter, modifications of the non-coding nucleotide sequences of the neutral protease signal peptide and K1 gene were made. The sequence modifications resulted in restriction enzyme sites, which would be used in subsequent cloning steps.

The restriction enzyme sites SacI and PacI were added to the 5' and 3'-ends of the neutral protease signal peptide and K1 gene sequences, respectively, by PCR using the primers SEQ ID NO. 18 and SEQ ID NO. 19. PCR amplfication was performed by the protocol described in Example 3. A 1919 bp PCR product was isolated and ligated into the pSYCO109mcs wild-type GI yqhD plasmid as disclosed in U.S. patent application Ser. No. 10/420,587, which was also digested with the enzymes SacI and PacI. The resulting plasmid contains a wild-type GI promoter and the NPR-signal sequence linked in a translational fusion to the k1 gene. This construct was designated WTGI-ss-K1. A variant GI promoter was also used to direct expression of the NPR-signal peptide/K1 fusion. A 1919 bp PCR product, resulting from a reaction using the primers SEQ ID NO:18 and SEQ ID NO:19 was placed into the pSYCO109mcs-short 1.6 GI yqhD plasmid, using SacI and PacI restriction enzyme sites. The resulting plasmid was designated LowGI-ss-K1. This variant promoter when operably linked to a yqhD gene was previously shown to direct lower levels of gene expression (U.S. patent application Ser. No. 10/420,587) as compared to the wild-type GI promoter-yqhD construct.

Demonstrating effective expression of the K1 gene using the wild-type and variant GI promoters was accomplished by an activity assay. *E. coli* cells (strain DH5α, Invitrogen, Carlsbad, Calif.) were transformed with the plasmids WTGI-ss-K1 and LowGI-ss-K1 and grown overnight in LB medium. Cell pellets were recovered by centrifugation and suspended in 1/10 volume sodium-phosphate buffer (10 mM, pH 7.0). The cells in the suspension were lysed with a French press and cell-debris was removed by centrifugation. Total protein concentration was determined by Bradford assay (Bio-Rad, Hercules, Calif.). Activity of the K1 gene product in a total protein isolate was assayed using 4-nitrophenyl-α-D-glucopyranoside (PNPG, Sigma, ST. Louis, Mo.). Total protein extract from cells containing the plasmids WTGI-ss-K1, LowGI-ss-K1, NPR-ss-K1 (positive control) and pSYCO109 (negative control) were incubated in a 10 mM sodium phosphate buffered solution containing 10 mM PNPG for up to 30 min at 30°C. Release of the glucose residue from PNPG results in PNP accumulation, which absorbs light at 400 nm. PNP accumulation as a direct result of k1 enzyme activity was monitored over time by absorbance at a wavelength of 400 nm. Table 11 below demonstrates that a promoter, other than the neutral protease promoter, may be used to direct expression of an active K1 gene. The results also demonstrate that an alternative promoter may be used to modify the level of K1 expression and that K1 activity corresponds to the relative level of promoter strength.

TABLE 11

Rate of PNP production resulting from K1 enzyme activity

| Plasmid | Activity (mM PNP/mg protein $min^{-1}$) |
|---|---|
| WTGI-ss-K1 (high expresser) | 0.0144 |
| NPR-ss-K1 (positive control) | 0.0104 |
| LowGI-ss-K1 (low expresser) | 0.0028 |
| pSYCO109 (negative control) | 0.0002 |

Example 9

Integration of the *B. breve* k1 Gene into the *E. coli* Genome

Integrating the desired DNA into the cell's genome may enhance the stability of gene expression over time and under a variety of fermentation conditions. However, the location of integration may affect gene expression level and, ultimately, the effectiveness of the desired enzyme activity.

Integration of the k1 expression cassette (NPR promoter-signal peptide-k1 gene) into the genome of *E. coli* (strain Fm5) and the demonstration of utility by the use of an α(1,6)-linked glucose substrate was accomplished by first cloning into the plasmid pKD3 (Datsenko and Wanner, *Proc. Natl. Acad. Sci.* 97:6640-6645 (2000)). The host aldA (aldehyde dehydrogenase A) and aldB (aldehyde dehydrogenase B) genomic sites were chosen for integration. PCR primers were designed that had homology to the plasmid pKD3, aldA or aldB and k1 gene sequences (SEQ ID NOs:20 through 23).

PCR amplification was performed by the protocol described in Example 3. PCR products resulting from a reaction with the primers SEQ ID NOs. 21-23 and the plasmid pKD3 containing the k1 expression cassette were isolated, ligated and transformed into *E. coli* (Fm5). Cells containing the integrated k1 expression cassette were selected by growth on LB medium containing chloramphenicol. Chloramphenicol positive colonies were tested for the presence of the k1 gene by PCR reaction, using the primers SEQ ID NO:7 and SEQ ID NO:8.

Fm5 lines containing the integrated k1 expression cassette were further tested for activity by growth analysis in media containing isomaltose as the sole carbohydrate source. Chloramphenicol and PCR positive colonies were inoculated into TM2 medium (see Example 7) with 0.5% isomaltose (w/v) and grown at 35° C. Samples were removed at various time points and characterized for cell mass accumulation by optical density (A600 nm) and isomaltose consumption (by HPLC, see General Methods).

Table 12 below demonstrates that Fm5 cells alone do not metabolize isomaltose when provided as the sole carbohydrate source. This is shown by the low level of cell mass accumulation when grown in TM2 medium with 0.5% isomaltose. Low-level growth of the negative line Fm5 was observed, but due only to a small amount of the fermentable sugar maltose contaminating the isomaltose source material (Sigma, St. Louis, Mo.). Cells containing the integrated K1 expression cassette grew at a much higher rate and to a higher final optical density following the 25 hr time period. A PCR-positive colony containing the k1 expression cassette integrated at the aldA site was designated A2-3. Colonies, positive by PCR, containing the k1 expression cassette integrated at the aldB site were designated B1-1 and B1-2.

TABLE 12

Cell mass accumulation (A600 nm)

| Time (hours) | FM5 | FM5-A2-3 | FM5-B1-1 | FM5-B1-2 |
|---|---|---|---|---|
| 0 | 0.02 | 0.02 | 0.02 | 0.02 |
| 3 | 0.66 | 0.72 | 0.76 | 0.75 |
| 6 | 2.75 | 3.17 | 6.60 | 6.01 |
| 8 | 3.34 | 4.50 | 10.40 | 9.92 |
| 11 | 3.72 | 8.34 | 10.41 | 10.10 |
| 25 | 3.66 | 10.16 | 11.10 | 10.78 |

Isomaltose consumption by cells containing the integrated K1 expression cassette was also compared to the Fm5 negative control line by HPLC analysis. The data in Table 13 demonstrate that the K1 expression cassette is active following integration and allows cells to completely utilize available sugar containing α(1,6)-linked glucose, compared to the negative control which does not utilize this carbohydrate. The data also show that isomaltose is not consumed at the same rate in lines where the gene has been integrated into the aldA, as compared to the aldB, sites.

TABLE 13

Isomaltose Consumption (g/L)

| Time (hours) | FM5 | FM5-A2-3 | FM5-B1-1 | FM5-B1-2 |
|---|---|---|---|---|
| 0 | 5.56 | 5.46 | 5.36 | 5.31 |
| 3 | 5.52 | 5.35 | 5.31 | 5.30 |
| 6 | 5.60 | 4.73 | 1.81 | 1.78 |
| 8 | 5.48 | 3.64 | 0 | 0 |
| 11 | 5.77 | 1.34 | 0 | 0 |
| 25 | 5.55 | 0 | 0 | 0 |

What is claimed is:

1. An isolated nucleic acid molecule encoding an α(1,6)-linked glucose oligosaccharide hydrolyzing polypeptide selected from the group consisting of:
   (a) an isolated nucleic acid molecule encoding the amino acid sequence SEQ ID NO:2;
   (b) a nucleic acid molecule that hybridizes with (a) under the following stringent hybridization conditions: 0.1× SSC, 0.1% SDS, 65° C. and washed with 2×SSC, 0.1% SDS followed by 0.1×SSC, 0.1% SDS; and
   (c) a nucleic acid molecule that is fully complementary to (a) or (b).

2. The isolated nucleic acid molecule of claim 1 wherein said nucleic acid molecule is set forth in SEQ ID NO:1.

3. An isolated nucleic acid having the SEQ ID NO: 1 encoding an α(1,6)-linked glucose oligosaccharide hydrolyzing polypeptide consisting of:
   (a) an isolated nucleic acid molecule encoding a chimeric protein comprised of a signal peptide operably linked to an α(1,6)-linked glucose oligosaccharide hydrolyzing polypeptide;
   (b) a nucleic acid molecule that hybridizes with (a) under the following stringent hybridization conditions: 0.1× SSC, 0.1% SDS, 65° C. and washed with 2×SSC, 0.1% SDS followed by 0.1×SSC, 0.1% SDS; and
   (c) a nucleic acid molecule that is fully complementary to (a) or (b).

4. The isolated nucleic acid molecule of claim 3, wherein the α(1,6)-linked glucose oligosaccharide hydrolyzing polypeptide is SEQ ID NO:2.

5. The isolated nucleic acid molecule of claim 3, wherein the signal peptide is SEQ ID NO:24 or SEQ ID NO:25, and wherein the α(1,6)-linked glucose oligosaccharide hydrolyzing polypeptide is SEQ ID NO:2.

6. The isolated nucleic acid molecule of claim 3 encoding the α(1,6)-linked glucose oligosaccharide hydrolyzing polypeptide, the isolated nucleic acid molecule having the sequence as set forth in SEQ ID NO:1.

7. A chimeric gene comprising the isolated nucleic acid molecule of claim 1 or claim 3 operably linked to suitable regulatory sequences.

8. The chimeric gene of claim 7 wherein the suitable regulatory sequence is selected from the group comprising CYC1, HIS3, GAL1, GAL10, ADH1, PGK, PHO5, GAPDH, ADC1, TRP1, URA3, LEU2, ENO, TPI, AOX1, lac, ara, tet, trp, $IP_L$, $IP_R$, T7, tac, trc, apr, npr, nos, and GI.

9. A vector comprising the chimeric gene of claim 7.

10. A transformed host cell comprising the chimeric gene of claim 7.

11. The transformed host cell of claim 10 wherein the chimeric gene is integrated into the chromosome or is plasmid-borne.

12. The transformed host cell of claim 10, wherein the host cell is selected from the group consisting of bacteria, yeast, and filamentous fungi.

13. The transformed host cell of claim 12, wherein the transformed host cell is selected from the genera *Aspergillus, Trichoderma, Saccharomyces, Pichia, Candida, Hansenula, Rhodococcus, Acinetobacter, Arthrobacter, Brevibacterium, Acidovorax, Bacillus, Streptomyces, Escherichia, Salmonella, Pseudomonas,* or *Cornyebacterium.*

14. The transformed host cell of claim 12 wherein the transformed host cell is *E. coli.*

15. A method for the production of a target molecule in a recombinant host cell comprising:
   (a) contacting a transformed host cell comprising:
      (i) an isolated nucleic acid molecule encoding a chimeric protein comprised of a signal peptide operably linked to an α(1,6)-linked glucose oligosaccharide hydrolyzing polypeptide;
      (ii) a nucleic acid molecule that hybridizes with (i) under the following stringent hybridization conditions: 0.1× SSC, 0.1% SDS, 65° C. and washed with 2×SSC, 0.1% SDS followed by 0.1×SSC, 0.1% SDS; or
      (iii) a nucleic acid molecule that is fully complementary to (i) or (ii); and
      (iv) at least one chimeric gene for converting mononsaccharides to the target molecule,
   in the presence of limit dextrin under suitable conditions whereby the target molecule is produced; and
   (b) optionally recovering the target molecule produced in (a).

16. A method for the production of glycerol in a recombinant host cell comprising:
   (a) contacting a transformed host cell comprising:
      (i) an isolated nucleic acid molecule encoding a chimeric protein comprised of a signal peptide operably linked to an α(1,6)-linked glucose oligosaccharide hydrolyzing polypeptide;
      (ii) a nucleic acid molecule that hybridizes with (i) under the following stringent hybridization conditions: 0.1× SSC, 0.1% SDS, 65° C. and washed with 2×SSC, 0.1% SDS followed by 0.1×SSC, 0.1% SDS; or
      (iii) a nucleic acid molecule that is fully complementary to (i) or (ii); and
      (iv) at least one chimeric gene for converting mononsaccharides to glycerol,
   in the presence of limit dextrin under suitable conditions whereby glycerol is produced; and
   (b) optionally recovering the glycerol produced in (a).

17. A method for the production of 1,3-propanediol in a recombinant host cell comprising:
   (a) contacting a transformed host cell comprising:
      (i) an isolated nucleic acid molecule encoding a chimeric protein comprised of a signal peptide operably linked to an α(1,6)-linked glucose oligosaccharide hydrolyzing polypeptide;
      (ii) a nucleic acid molecule that hybridizes with (i) under the following stringent hybridization conditions: 0.1× SSC, 0.1% SES, 65° C. and washed with 2×SSC, 0.1% SDS followed by 0.1×SSC, 0.1% SDS; or
      (iii) a nucleic acid molecule that is fully complementary to (i) or (ii),
      (iv) at least one chimeric gene for converting mononsaccharides to 1,3-propanediol,
   in the presence of limit dextrin under suitable conditions whereby 1,3-propanediol is produced; and
   (b) optionally recovering the 1,3-propanediol produced in (a).

18. A method for the production of cell mass in a recombinant host cell comprising:
   (a) contacting a transformed host cell comprising:
      (i) an isolated nucleic acid molecule encoding a chimeric protein comprised of a signal peptide linked to an α(1,6)-linked glucose oligosaccharide hydrolyzing polypeptide;
      (ii) a nucleic acid molecule that hybridizes with (i) under the following stringent hybridization conditions: 0.1× SSC, 0.1% SDS, 65° C. and washed with 2×SSC, 0.1% SDS followed by 0.1×SSC, 0.1% SDS; and (iii) a nucleic acid molecule that is fully complementary to (i) or (ii), under suitable conditions in the presence of limit dextrin;

(b) optionally recovering the cell mass produced in (a).

19. The method of claim 15, claim 16, claim 17 or claim 18 wherein the signal peptide comprises SEQ ID NO:24 or SEQ ID NO:25.

20. A method for the production of a target molecule in a recombinant host cell comprising:
   (a) contacting a transformed host cell comprising:
      (i) an isolated nucleic acid molecule encoding the amino acid sequence of SEQ ID NO:2;
      (ii) a nucleic acid molecule that hybridizes with (i) under the following stringent hybridization conditions: 0.1× SSC, 0.1% SDS, 65° C. and washed with 2×SSC, 0.1% SDS followed by 0.1×SSC, 0.1% SDS; or
      (iii) a nucleic acid molecule that is fully complementary to (i) or (ii); and
      (iv) at least one chimeric gene for converting mononsaccharides to the target molecule,
   in the presence of limit dextrin under suitable conditions whereby the target molecule is produced; and
   (b) optionally recovering the target molecule produced in (a).

21. A method for the production of 1,3-propanediol in a recombinant host cell comprising:
   (a) contacting a transformed host cell comprising:
      (i) an isolated nucleic acid molecule encoding the amino acid sequence of SEQ ID NO:2;
      (ii) a nucleic acid molecule that hybridizes with (i) under the following stringent hybridization conditions: 0.1× SSC, 0.1% SDS, 65° C. and washed with 2×SSC, 0.1% SDS followed by 0.1×SSC, 0.1% SDS; or
      (iii) a nucleic acid molecule that is fully complementary to (i) or (ii); and
      (iv) at least one chimeric gene for converting mononsaccharides to 1,3-propanediol;
   in the presence of limit dextrin under suitable conditions whereby 1,3-propanediol is produced; and
   (b) optionally recovering the 1,3-propanediol produced in (a).

22. A method for the production of glycerol in a recombinant host cell comprising:
   (a) contacting a transformed host cell comprising:
      (i) an isolated nucleic acid molecule encoding the amino acid sequence of SEQ NO:2;
      (ii) a nucleic acid molecule that hybridizes with (i) under the following stringent hybridization conditions: 0.1× SSC, 0.1% SDS, 65° C. and washed with 2×SSC, 0.1% SDS followed by 0.1×SSC, 0.1% SDS; or
      (iii) a nucleic acid molecule that is fully complementary to (i) or (ii); and
      (iv) at least one chimeric gene for converting mononsaccharides to glycerol;
   in the presence of limit dextrin under suitable conditions whereby glycerol is produced; and
   (b) optionally recovering the glycerol produced in (a).

23. A method for the production of cell mass in a recombinant host cell comprising:
   (a) contacting a transformed host cell comprising:
      (i) an isolated nucleic acid molecule encoding the amino acid sequence of SEQ ID NO:2;
      (ii) a nucleic acid molecule that hybridizes with (i) under the following stringent hybridization conditions: 0.1× SSC, 0.1% SDS, 65° C. and washed with 2×SSC, 0.1% SDS followed by 0.1×SSC, 0.1% SDS; or
      (iii) a nucleic acid molecule that is fully complementary to (i) or (ii),
   in the presence of limit dextrin under suitable conditions whereby cell mass is produced; and
   (b) optionally recovering the cell mass produced in (a).

24. The method of claim 20, claim 21, claim 22 or claim 23 wherein the signal peptide is SEQ ID NO:24 or SEQ ID NO:25.

25. A method for degrading limit dextrin comprising:
   (a) contacting a transformed host cell comprising:
      (i) a nucleic acid molecule encoding the enzyme having amino acid sequence of SEQ ID NO:2;
      (ii) a nucleic acid molecule that hybridizes with (i) under the following stringent hybridization conditions: 0.1× SSC, 0.1% SDS, 65° C. and washed with 2×SSC, 0.1% SDS followed by 0.1×SSC, 0.1% SDS; or
      (iii) a nucleic acid molecule that is fully complementary to (i) or (ii),
   with an effective amount of limit dextrin substrate under suitable growth conditions; and
   (b) optionally recovering the product of step (a).

\* \* \* \* \*

SEQUENCE LISTING

<160> NUMBER OF SEQ ID NOS: 43

<210> SEQ ID NO 1
<211> LENGTH: 1815
<212> TYPE: DNA
<213> ORGANISM: Bifidobacterium breve
<220> FEATURE:
<221> NAME/KEY: misc_feature
<223> OTHER INFORMATION: ATCC#15700

<400> SEQUENCE: 1

```
atgaccgcca acaacctcaa tgacgactgg tggaagcagg ccgtcgttta ccagatttac     60
ccgcgcagct tcaaggacgt taacggcgac ggcatcggcg acatcgccgg cgttaccgag    120
aaaatggact acctgaaaaa cctcggcgtg gacgccatct ggctctcccc gttctacccc    180
tccgatctgg cggacggcgg ctacgacgtg atcgactacc gcaacgtcga cccgcgactg    240
ggcaccatgg acgacttcga cgccatggcc aaagccgcgc atgaggccgg catcaaggtg    300
atcgtggaca tcgtgcccaa tcacaccgcc gacaagcacg tgttcttcaa ggaagccctc    360
gccgccgagc ccggctcccc ggcgcgcgac cgctacatct tccgcgacgg ccgcggcgag    420
cacggcgaac tgccgcccaa cgactggcag tccttcttcg gcggcccggc ctgggctcgc    480
```

```
gtggccgacg gccagtggta tctgcacctg ttcgacaagg cgcaaccgga cgtcaactgg    540
aagaacccgg acatccacga ggaattcaag aaaaccctgc gcttctggtc cgaccacggc    600
accgacggct tccgcatcga cgtggcgcac ggtctggcca agaccttgaa atccaagccg    660
ctggaggagc tcggccgcga atacagcgtg gtcggcgtgc tgaatcacga cttcagccat    720
ccgctgttcg accgccgcga agtgcacgac atctaccgcg aatggcgcaa ggtgttcaac    780
gagtacgacc cgccgcgctt tgccgtggcc gaggcgtggg tggtacccga gcaccagcac    840
ctgtatgcct cgatggatga gctggggcag tccttcaact tcgactttgc gcaggccagc    900
tggtatgccg atgagttccg cgcagccatc gccgcgggtc tcaaggccgc tgccgaaacc    960
ggcggttcca ccaccacgtg ggtgatgaac aaccatgacg tgccgcgcag ccctccccgc    1020
tatggtctac gcaggtcaa gggcgcgcct taccaccagc tgccgcacga ctggctgctg    1080
cgcaacggca ccacgtatcc cgaggatcgc gagcttggca cccgccgcgc ccgcgccgcc    1140
gctttgatgg agctcggcct gcccggcgcc gcctatatct atcagggcga ggagctgggc    1200
ctgtttgaag tggccgatat tccgtgggat cgactggaag atccgaccgc tttccacacc    1260
gctcaggcca cgatggacaa gggccgagac ggctgccgcg tgccgattcc gtggaccgct    1320
gcaaacgaac cgaccttggc tgatttcagc cgcccgatcc cggccgatga cggcaccggc    1380
gagaaccacg tgccgctgtg cgccgccggc cagttcggca cgggcgcttc cttcggcttc    1440
tcgccggcta cgcgcgctga gggcgtgacg ccggccgccg acccgcacct gccgcagccg    1500
ttgtggttca aggattacgc ggtggacgtg gagcaggccg accggattc aatgctcgcg    1560 ctgtatcatg cggcgttggc gattcgtcag gagtcgctga ccgccacgcg tgacaccacc    1620
gctgagcagg tggatatggg gccggacgtg gtggcctaca cccgcgcggc ggttggtggc    1680
cgcacgttca cctcgatcac caacttcggc accgagccgg tggagctgcc tggaggctcc    1740
gtcgtgctga cgtccggccc gctgaccccc gacggccagc tccccaccga cacttctgcg    1800
tgggttatca agtag                                                     1815
```

<210> SEQ ID NO 2
<211> LENGTH: 604
<212> TYPE: PRT
<213> ORGANISM: Bifidobacterium breve
<220> FEATURE:
<221> NAME/KEY: misc_feature
<223> OTHER INFORMATION: ATCC#15700

<400> SEQUENCE: 2

```
Met Thr Ala Asn Asn Leu Asn Asp Asp Trp Trp Lys Gln Ala Val Val
1               5                   10                  15

Tyr Gln Ile Tyr Pro Arg Ser Phe Lys Asp Val Asn Gly Asp Gly Ile
            20                  25                  30

Gly Asp Ile Ala Gly Val Thr Glu Lys Met Asp Tyr Leu Lys Asn Leu
        35                  40                  45

Gly Val Asp Ala Ile Trp Leu Ser Pro Phe Tyr Pro Ser Asp Leu Ala
    50                  55                  60

Asp Gly Gly Tyr Asp Val Ile Asp Tyr Arg Asn Val Asp Pro Arg Leu
65                  70                  75                  80

Gly Thr Met Asp Asp Phe Asp Ala Met Ala Lys Ala Ala His Glu Ala
                85                  90                  95

Gly Ile Lys Val Ile Val Asp Ile Val Pro Asn His Thr Ala Asp Lys
            100                 105                 110
```

-continued

```
His Val Phe Phe Lys Glu Ala Leu Ala Ala Glu Pro Gly Ser Pro Ala
115                 120                 125

Arg Asp Arg Tyr Ile Phe Arg Asp Gly Arg Gly Glu His Gly Glu Leu
130                 135                 140

Pro Pro Asn Asp Trp Gln Ser Phe Phe Gly Pro Ala Trp Ala Arg
145                 150                 155                 160

Val Ala Asp Gly Gln Trp Tyr Leu His Leu Phe Asp Lys Ala Gln Pro
165                 170                 175

Asp Val Asn Trp Lys Asn Pro Asp Ile His Glu Glu Phe Lys Lys Thr
180                 185                 190

Leu Arg Phe Trp Ser Asp His Gly Thr Asp Gly Phe Arg Ile Asp Val
195                 200                 205

Ala His Gly Leu Ala Lys Asp Leu Glu Ser Lys Pro Leu Glu Glu Leu
210                 215                 220

Gly Arg Glu Tyr Ser Val Val Gly Val Leu Asn His Asp Phe Ser His
225                 230                 235                 240

Pro Leu Phe Asp Arg Arg Glu Val His Asp Ile Tyr Arg Glu Trp Arg
245                 250                 255

Lys Val Phe Asn Glu Tyr Asp Pro Pro Arg Phe Ala Val Ala Glu Ala
260                 265                 270

Trp Val Val Pro Glu His Gln His Leu Tyr Ala Ser Met Asp Glu Leu
275                 280                 285

Gly Gln Ser Phe Asn Phe Asp Phe Ala Gln Ala Ser Trp Tyr Ala Asp
290                 295                 300

Glu Phe Arg Ala Ala Ile Ala Ala Gly Leu Lys Ala Ala Ala Glu Thr
305                 310                 315                 320

Gly Gly Ser Thr Thr Thr Trp Val Met Asn Asn His Asp Val Pro Arg
325                 330                 335

Ser Pro Ser Arg Tyr Gly Leu Pro Gln Val Lys Gly Ala Pro Tyr His
340                 345                 350

Gln Leu Pro His Asp Trp Leu Leu Arg Asn Gly Thr Thr Tyr Pro Glu
355                 360                 365

Asp Arg Glu Leu Gly Thr Arg Arg Ala Arg Ala Ala Leu Met Glu
370                 375                 380

Leu Gly Leu Pro Gly Ala Ala Tyr Ile Tyr Gln Gly Glu Glu Leu Gly
385                 390                 395                 400

Leu Phe Glu Val Ala Asp Ile Pro Trp Asp Arg Leu Glu Asp Pro Thr
405                 410                 415

Ala Phe His Thr Ala Gln Ala Thr Met Asp Lys Gly Arg Asp Gly Cys
420                 425                 430

Arg Val Pro Ile Pro Trp Thr Ala Ala Asn Glu Pro Thr Leu Ala Asp
435                 440                 445

Phe Ser Arg Pro Ile Pro Ala Asp Asp Gly Thr Gly Glu Asn His Val
450                 455                 460

Pro Leu Cys Ala Ala Gly Gln Phe Gly Thr Gly Ala Ser Phe Gly Phe
465                 470                 475                 480

Ser Pro Ala Thr Arg Ala Glu Gly Val Thr Pro Ala Ala Asp Pro His
485                 490                 495

Leu Pro Gln Pro Leu Trp Phe Lys Asp Tyr Ala Val Asp Val Glu Gln
500                 505                 510

Ala Asp Pro Asp Ser Met Leu Ala Leu Tyr His Ala Ala Leu Ala Ile
515                 520                 525

Arg Gln Glu Ser Leu Thr Ala Thr Arg Asp Thr Thr Ala Glu Gln Val
```

```
                    Asp Met Gly Pro Asp Val Val Ala Tyr Thr Arg Ala Ala Val Gly Gly
                    545                 550                 555                 560

Arg Thr Phe Thr Ser Ile Thr Asn Phe Gly Thr Glu Pro Val Glu Leu
                    565                 570                 575

Pro Gly Gly Ser Val Val Leu Thr Ser Gly Pro Leu Thr Pro Asp Gly
                    580                 585                 590

Gln Leu Pro Thr Asp Thr Ser Ala Trp Val Ile Lys
                    595                 600

<210> SEQ ID NO 3
<211> LENGTH: 1845
<212> TYPE: DNA
<213> ORGANISM: Bifidobacterium breve
<220> FEATURE:
<221> NAME/KEY: misc_feature
<223> OTHER INFORMATION: ATCC#15700

<400> SEQUENCE: 3
atgaataagg agccaacgat gactactttc aaccgcacaa taattcccga cgccattcgc      60
accaacggag ccacgcccaa cccgtggtgg tcgaacgccg tcgtctacca gatttaccca     120
cgttccttcc aggacacgaa cggcgatggt ctcggcgacc tgaagggcat cacctcccgc     180
ctcgactatc tcgccgacct cggcgtggat gtgctgtggc tctctccggt ctacaggtcc     240
ccgcaagacg acaacggcta cgacatctcc gactaccggg acatcgaccc gctgttcggc     300
acgcttgaca catggacga gctgctcgcc gaagcgcaca agcgcggcct caagatcgtg     360
atggacctgg tggtcaatca cacctctgac gagcacgcgt ggttcgaggc gtcgaaggac     420
aaggacgacc cgcacgccga ctggtactgg tggcgtcccg cccgccccgg ccacgagccg     480
ggcacgcccg cgccgagcc gaatcagtgg ggctcctact cggcggttc cgcatgggag     540 tacagcccg agcgcggcga gtactacctg caccagttct cgaagaagca gcctgatctc     600
aactgggaga acccggccgt gcgccgtgca gtgtacgaca tgatgaactg gtggctcgat     660
cgcggcatcg acggcttccg tatggacgtc atcacccta tctccaagcg caccgacccc     720
aacggcaggc tccccggcga ggccggttcc gagctgcagg acctgccggt gggggaggag     780
ggctactccg acccgaatcc gttctgtgcg acggccccc gtcaggatga attcctggct     840
gaaatgcgcc gtgaggtatt cgaagggcgt gacggcttcc tgactgtagg cgaggcgcca     900
ggcgtcacag cccagcgcaa cgaatacatc accgatccgg ccaatggcga gctggatatg     960
ctcttcctat ttgagcatgt tgattttgat tgcgaaggta ccaagtggaa gccgttgccg    1020
ctcgatctgc cgaagcttaa gagcatcatg gccggctatc aggccgctgt gcagaacgca    1080
ggatgggcca gcctattcac cggcaaccac gatcagccgc gcgtggtttc cgctggggt    1140 gacgattcct cggaagaggc tcgggtccgc tcggccaagg cccttggcct gatgctgcac    1200
ctgcaccgtg gtaccccgta catctatcag ggtgaagaat gggcatgac cgacgcccac    1260 ttcactcgtc tcgaccagta ccgcgaccct gaatccctga cgccctaccg tcaaagggtc    1320
gaagaggcca aggtgcagtc gcccgaatcc atgatggccg gtatcgccgc ccgcggtcgt    1380
gacaactcac gcacaccgat gcagtgggat ggctccgtct acgccggttt caccgcacct    1440
gacgcagccg ccgagccatg gatctccgtg aatccgaatc atgccgagat caacgccgcc    1500
ggcgaattcg atgatccgga ttcggtgtac tccttctaca agcggctcat cgcgctgcgc    1560
cacgacatgc ctgtcgtgga ggccggcgac tggcatctgc tcgacgcgga cgatgcgcat    1620
```

-continued

```
gtgtatgcct tcactcgtac cctcggtgac gagaagttgt tggtcgtggt caatatgtcc    1680
gggcgaactg ttgatttgcc tcgcgaatcc gccgaactgt ggcagtggc cgatggcctt     1740 gccgagtcga acgtggtgat cagcacgtat gatgccccgc acgctgtgac cgctcttgcc    1800
ggccgtgagc ttgcaccatg ggagggcgtc gtcgtcagcc tataa                    1845
```

<210> SEQ ID NO 4
<211> LENGTH: 613
<212> TYPE: PRT
<213> ORGANISM: Bifidobacterium breve
<220> FEATURE:
<221> NAME/KEY: misc_feature
<223> OTHER INFORMATION: ATCC#15700

<400> SEQUENCE: 4

```
Met Asn Lys Glu Pro Thr Met Thr Thr Phe Asn Arg Thr Ile Ile Pro
1               5                   10                  15

Asp Ala Ile Arg Thr Asn Gly Ala Thr Pro Asn Pro Trp Trp Ser Asn
            20                  25                  30

Ala Val Val Tyr Gln Ile Tyr Pro Arg Ser Phe Gln Asp Thr Asn Gly
        35                  40                  45

Asp Gly Leu Gly Asp Leu Lys Gly Ile Thr Ser Arg Leu Asp Tyr Leu
    50                  55                  60

Ala Asp Leu Gly Val Asp Val Leu Trp Leu Ser Pro Val Tyr Arg Ser
65                  70                  75                  80

Pro Gln Asp Asp Asn Gly Tyr Asp Ile Ser Asp Tyr Arg Asp Ile Asp
                85                  90                  95

Pro Leu Phe Gly Thr Leu Asp Asp Met Asp Glu Leu Leu Ala Glu Ala
            100                 105                 110

His Lys Arg Gly Leu Lys Ile Val Met Asp Leu Val Val Asn His Thr
        115                 120                 125

Ser Asp Glu His Ala Trp Phe Glu Ala Ser Lys Asp Lys Asp Asp Pro
    130                 135                 140

His Ala Asp Trp Tyr Trp Trp Arg Pro Ala Arg Pro Gly His Glu Pro
145                 150                 155                 160

Gly Thr Pro Gly Ala Glu Pro Asn Gln Trp Gly Ser Tyr Phe Gly Gly
                165                 170                 175

Ser Ala Trp Glu Tyr Ser Pro Glu Arg Gly Glu Tyr Tyr Leu His Gln
            180                 185                 190

Phe Ser Lys Lys Gln Pro Asp Leu Asn Trp Glu Asn Pro Ala Val Arg
        195                 200                 205

Arg Ala Val Tyr Asp Met Met Asn Trp Trp Leu Asp Arg Gly Ile Asp
    210                 215                 220

Gly Phe Arg Met Asp Val Ile Thr Leu Ile Ser Lys Arg Thr Asp Pro
225                 230                 235                 240

Asn Gly Arg Leu Pro Gly Glu Ala Gly Ser Glu Leu Gln Asp Leu Pro
                245                 250                 255

Val Gly Glu Glu Gly Tyr Ser Asp Pro Asn Pro Phe Cys Ala Asp Gly
            260                 265                 270

Pro Arg Gln Asp Glu Phe Leu Ala Glu Met Arg Arg Glu Val Phe Glu
        275                 280                 285

Gly Arg Asp Gly Phe Leu Thr Val Gly Glu Ala Pro Gly Val Thr Ala
    290                 295                 300

Gln Arg Asn Glu Tyr Ile Thr Asp Pro Ala Asn Gly Glu Leu Asp Met
305                 310                 315                 320
```

```
Leu Phe Leu Phe Glu His Val Asp Phe Asp Cys Glu Gly Thr Lys Trp
325                 330                 335
Lys Pro Leu Pro Leu Asp Leu Pro Lys Leu Lys Ser Ile Met Ala Gly
340                 345                 350
Tyr Gln Ala Ala Val Gln Asn Ala Gly Trp Ala Ser Leu Phe Thr Gly
355                 360                 365
Asn His Asp Gln Pro Arg Val Val Ser Arg Trp Gly Asp Ser Ser
370                 375                 380
Glu Glu Ala Arg Val Arg Ser Ala Lys Ala Leu Gly Leu Met Leu His
385                 390                 395                 400
Leu His Arg Gly Thr Pro Tyr Ile Tyr Gln Gly Glu Glu Leu Gly Met
405                 410                 415
Thr Asp Ala His Phe Thr Arg Leu Asp Gln Tyr Arg Asp Leu Glu Ser
420                 425                 430
Leu Asn Ala Tyr Arg Gln Arg Val Glu Glu Ala Lys Val Gln Ser Pro
435                 440                 445
Glu Ser Met Met Ala Gly Ile Ala Ala Arg Gly Arg Asp Asn Ser Arg
450                 455                 460
Thr Pro Met Gln Trp Asp Gly Ser Val Tyr Ala Gly Phe Thr Ala Pro
465                 470                 475                 480
Asp Ala Ala Ala Glu Pro Trp Ile Ser Val Asn Pro Asn His Ala Glu
485                 490                 495
Ile Asn Ala Ala Gly Glu Phe Asp Asp Pro Asp Ser Val Tyr Ser Phe
500                 505                 510
Tyr Lys Arg Leu Ile Ala Leu Arg His Asp Met Pro Val Val Glu Ala
515                 520                 525
Gly Asp Trp His Leu Leu Asp Ala Asp Asp Ala His Val Tyr Ala Phe
530                 535                 540
Thr Arg Thr Leu Gly Asp Glu Lys Leu Leu Val Val Asn Met Ser
545                 550                 555                 560
Gly Arg Thr Val Asp Leu Pro Arg Glu Ser Ala Glu Leu Leu Ala Val
565                 570                 575
Ala Asp Gly Leu Ala Glu Ser Asn Val Val Ile Ser Thr Tyr Asp Ala
580                 585                 590
Pro His Ala Val Thr Ala Leu Ala Gly Arg Glu Leu Ala Pro Trp Glu
595                 600                 605
Gly Val Val Val Ser
610

<210> SEQ ID NO 5
<211> LENGTH: 1818
<212> TYPE: DNA
<213> ORGANISM: Bifidobacterium breve
<220> FEATURE:
<221> NAME/KEY: misc_feature
<223> OTHER INFORMATION: ATCC#15700

<400> SEQUENCE: 5
atgatgacct ctttcaaccg tgaaccctg cccgacgccg tccgcacgaa tggcgcctcc      60
ccgaacccgt ggtggtcgaa cgccgtcgtc taccagattt acccacgttc cttccaggac    120
acgaacggcg atggtttcgg agatcttaag ggcattactt cccgcctcga ctatcttgcc    180
gacctcggcg tggatgtgct gtggctctcc ccggtctaca ggtccccgca agacgacaac    240
ggctacgaca tctccgacta ccgggacatc gaccgctgt cggcacgct cgacgacatg      300 gacgagctgc tcgccgaagc gcacaagcgc ggcctcaaga tcgtgatgga cctggtcgtc    360
```

```
aaccacacct ccgacgagca cgcgtggttc gaggcgtcga aggacaagga cgacccgcac    420
gccgactggt actggtggcg tcccgcccgc cccggccacg agcccggcac gcccggcgcc    480
gagccgaacc agtggggctc ctacttcggc ggctccgcat gggaatattg ccccgagcgt    540
ggtgagtact atctccacca gttctcgaag aagcagccgg acctcaactg ggagaacccg    600
gccgtacgcc gagccgtgta cgacatgatg aactggtggc tcgatcgcgg catcgacggc    660
ttccgcatgg acgtcatcac cctgatctcc aagcgcacgg atgcaaacgg caggctgccc    720
ggcgagaccg gttccgagct gcaggacctg ccggtggggg aggagggcta ctccaacccg    780
aacccgttct gcgccgacgg tccgcgtcag gacgagttcc tcgccgagat gcgccgcgag    840
gtgttcgacg ggcgtgacgg cttcctcacc gtcggcgagg cccccggcat caccgccgaa    900
cgcaacgagc acatcaccga ccccgccaac ggcgagctgg atatgctctt cctgttcgaa    960
cacatgggcg tcgaccaaac ccccgaatcg aaatgggacg acaaaccatg gacgccggcc   1020
gacctcgaaa ccaagctcgc cgaacaacag gacgccatcg cccgacacgg ctgggccagc   1080
ctgttcctcg acaaccacga ccagccgcgt gtcgtctccc gttggggcga cgacaccagc   1140
aagaccggcc gcatccgctc cgccaaggcg ctcgcgctgc tgctgcacat gcaccgcggc   1200
actccgtatg tctaccaggg cgaggagctc ggcatgacca tgcgcacttt cacctcgctc   1260
gaccagtacc gcgacctcga atccatcaac gcctaccatc aacgcgtcga ggaaaccggg   1320
atacggacat cggagaccat gatgcgatcc ctcgcccgat acggcaggga caacgcgcgc   1380
accccgatgc aatgggacga ctccacctac gccggcttca ccatgcccga cgccccggtc   1440
gaaccctgga tcgccgtcaa cccgaaccac acggagatca acgccgccga cgagatcgac   1500
gaccccgact ccgtgtactc gttccacaaa cggctcatcg ccctgcgtca caccgacccc   1560
gtggtcgccg ccggcgacta ccgacgcgtg gaaaccggaa acgaccggat catcgccttc   1620
accagaaccc tcgacgagcg aaccatcctc accgtcatca acctctcgcc cacacaggcc   1680
gcaccggccg gagaactgga aacgatgccc gacggcacga tcctcatcgc caacacggac   1740
gatcccgtag gaaacctgaa accacgggga cactcggac catgggaggc gttcgccatg    1800
gaaaccgatc cggaataa                                                 1818
```

<210> SEQ ID NO 6
<211> LENGTH: 605
<212> TYPE: PRT
<213> ORGANISM: Bifidobacterium breve
<220> FEATURE:
<221> NAME/KEY: misc_feature
<223> OTHER INFORMATION: ATCC#15700

<400> SEQUENCE: 6

```
Met Met Thr Ser Phe Asn Arg Glu Pro Leu Pro Asp Ala Val Arg Thr
1               5                   10                  15

Asn Gly Ala Ser Pro Asn Pro Trp Trp Ser Asn Ala Val Val Tyr Gln
            20                  25                  30

Ile Tyr Pro Arg Ser Phe Gln Asp Thr Asn Gly Asp Gly Phe Gly Asp
        35                  40                  45

Leu Lys Gly Ile Thr Ser Arg Leu Asp Tyr Leu Ala Asp Leu Gly Val
    50                  55                  60

Asp Val Leu Trp Leu Ser Pro Val Tyr Arg Ser Pro Gln Asp Asp Asn
65                  70                  75                  80

Gly Tyr Asp Ile Ser Asp Tyr Arg Asp Ile Asp Pro Leu Phe Gly Thr
                85                  90                  95
```

```
Leu Asp Asp Met Asp Glu Leu Leu Ala Glu Ala His Lys Arg Gly Leu
100                 105                 110

Lys Ile Val Met Asp Leu Val Val Asn His Thr Ser Asp Glu His Ala
115                 120                 125

Trp Phe Glu Ala Ser Lys Asp Lys Asp Pro His Ala Asp Trp Tyr
130                 135                 140

Trp Trp Arg Pro Ala Arg Pro Gly His Glu Pro Gly Thr Pro Gly Ala
145                 150                 155                 160

Glu Pro Asn Gln Trp Gly Ser Tyr Phe Gly Gly Ser Ala Trp Glu Tyr
165                 170                 175

Cys Pro Glu Arg Gly Glu Tyr Tyr Leu His Gln Phe Ser Lys Lys Gln
180                 185                 190

Pro Asp Leu Asn Trp Glu Asn Pro Ala Val Arg Arg Ala Val Tyr Asp
195                 200                 205

Met Met Asn Trp Trp Leu Asp Arg Gly Ile Asp Gly Phe Arg Met Asp
210                 215                 220

Val Ile Thr Leu Ile Ser Lys Arg Thr Asp Ala Asn Gly Arg Leu Pro
225                 230                 235                 240

Gly Glu Thr Gly Ser Glu Leu Gln Asp Leu Pro Val Gly Glu Glu Gly
245                 250                 255

Tyr Ser Asn Pro Asn Pro Phe Cys Ala Asp Gly Pro Arg Gln Asp Glu
260                 265                 270

Phe Leu Ala Glu Met Arg Arg Glu Val Phe Asp Gly Arg Asp Gly Phe
275                 280                 285

Leu Thr Val Gly Glu Ala Pro Gly Ile Thr Ala Glu Arg Asn Glu His
290                 295                 300

Ile Thr Asp Pro Ala Asn Gly Glu Leu Asp Met Leu Phe Leu Phe Glu
305                 310                 315                 320

His Met Gly Val Asp Gln Thr Pro Glu Ser Lys Trp Asp Asp Lys Pro
325                 330                 335

Trp Thr Pro Ala Asp Leu Glu Thr Lys Leu Ala Glu Gln Gln Asp Ala
340                 345                 350

Ile Ala Arg His Gly Trp Ala Ser Leu Phe Leu Asp Asn His Asp Gln
355                 360                 365

Pro Arg Val Val Ser Arg Trp Gly Asp Asp Thr Ser Lys Thr Gly Arg
370                 375                 380

Ile Arg Ser Ala Lys Ala Leu Ala Leu Leu His Met His Arg Gly
385                 390                 395                 400

Thr Pro Tyr Val Tyr Gln Gly Glu Glu Leu Gly Met Thr Asn Ala His
405                 410                 415

Phe Thr Ser Leu Asp Gln Tyr Arg Asp Leu Glu Ser Ile Asn Ala Tyr
420                 425                 430

His Gln Arg Val Glu Glu Thr Gly Ile Arg Thr Ser Glu Thr Met Met
435                 440                 445

Arg Ser Leu Ala Arg Tyr Gly Arg Asp Asn Ala Arg Thr Pro Met Gln
450                 455                 460

Trp Asp Asp Ser Thr Tyr Ala Gly Phe Thr Met Pro Asp Ala Pro Val
465                 470                 475                 480

Glu Pro Trp Ile Ala Val Asn Pro Asn His Thr Glu Ile Asn Ala Ala
485                 490                 495

Asp Glu Ile Asp Asp Pro Asp Ser Val Tyr Ser Phe His Lys Arg Leu
500                 505                 510
```

```
Ile Ala Leu Arg His Thr Asp Pro Val Val Ala Ala Gly Asp Tyr Arg
515                 520                 525
Arg Val Glu Thr Gly Asn Asp Arg Ile Ile Ala Phe Thr Arg Thr Leu
530                 535                 540
Asp Glu Arg Thr Ile Leu Thr Val Ile Asn Leu Ser Pro Thr Gln Ala
545                 550                 555                 560
Ala Pro Ala Gly Glu Leu Glu Thr Met Pro Asp Gly Thr Ile Leu Ile
565                 570                 575
Ala Asn Thr Asp Asp Pro Val Gly Asn Leu Lys Thr Thr Gly Thr Leu
580                 585                 590
Gly Pro Trp Glu Ala Phe Ala Met Glu Thr Asp Pro Glu
595                 600                 605

<210> SEQ ID NO 7
<211> LENGTH: 39
<212> TYPE: DNA
<213> ORGANISM: artificial sequence
<220> FEATURE:
<223> OTHER INFORMATION: primer

<400> SEQUENCE: 7
gcatgcggat ccatgcaaaa acattggtgg cacaaggca                              39

<210> SEQ ID NO 8
<211> LENGTH: 44
<212> TYPE: DNA
<213> ORGANISM: artificial sequence
<220> FEATURE:
<223> OTHER INFORMATION: primer

<400> SEQUENCE: 8
ggtaccgtcg acttagttta tcttaataca aaaagcatcc caag                        44

<210> SEQ ID NO 9
<211> LENGTH: 39
<212> TYPE: DNA
<213> ORGANISM: artificial sequence
<220> FEATURE:
<223> OTHER INFORMATION: primer

<400> SEQUENCE: 9
gacgtatatg atatccgcgc tagcagagga tgtgctgcc                              39

<210> SEQ ID NO 10
<211> LENGTH: 17
<212> TYPE: DNA
<213> ORGANISM: artificial sequence
<220> FEATURE:
<223> OTHER INFORMATION: primer

<400> SEQUENCE: 10
gaattcgagc tcggtac                                                      17

<210> SEQ ID NO 11
<211> LENGTH: 39
<212> TYPE: DNA
<213> ORGANISM: artificial sequence
<220> FEATURE:
<223> OTHER INFORMATION: primer

<400> SEQUENCE: 11
gacgtatatg atatccgcgc tagcacccgg cagactgat                              39
```

<210> SEQ ID NO 12
<211> LENGTH: 29
<212> TYPE: DNA
<213> ORGANISM: artificial sequence
<220> FEATURE:
<223> OTHER INFORMATION: primer

<400> SEQUENCE: 12
atgcatggta ccgatctaac attttcccc                                29

<210> SEQ ID NO 13
<211> LENGTH: 36
<212> TYPE: DNA
<213> ORGANISM: artificial sequence
<220> FEATURE:
<223> OTHER INFORMATION: primer

<400> SEQUENCE: 13
gagtctgcta gcgcgatgca aaaacattgg tggcac                        36

<210> SEQ ID NO 14
<211> LENGTH: 42
<212> TYPE: DNA
<213> ORGANISM: artificial sequence
<220> FEATURE:
<223> OTHER INFORMATION: primer

<400> SEQUENCE: 14
cgcggatccg ctagcgcgat gatgacctct ttcaaccgtg aa                 42

<210> SEQ ID NO 15
<211> LENGTH: 36
<212> TYPE: DNA
<213> ORGANISM: artificial sequence
<220> FEATURE:
<223> OTHER INFORMATION: primer

<400> SEQUENCE: 15
gagtctaagc ttttattccg gatcggtttc catggc                        36

<210> SEQ ID NO 16
<211> LENGTH: 1611
<212> TYPE: DNA
<213> ORGANISM: Streptococcus mutans
<220> FEATURE:
<221> NAME/KEY: misc_feature
<223> OTHER INFORMATION: ATCC#25175D

<400> SEQUENCE: 16
atgcaaaaac attggtggca caaggcaact gtttatcaaa tttatccaaa atctttatg      60 gatacaaatg tgatggaat tggtgatctc aaaggtatta cgagtaaatt ggattatttg     120
caaaagttag gggttatggc tatttggcta tctccagttt atgatagccc catggatgac    180
aatggctatg acattgcgaa ctatgaagca attgcggata tttttggcaa tatggctgat    240
atggataatt tgctgacgca ggcaaaaatg cgcgacataa aaatcattat ggatctagtg    300
gttaatcata cctcagatga acatacttgg tttattgaag cacgtgagca tccagacagt    360
tctgaacgcg attattatat tggtgtgac cagccaaatg atttggaatc tattttcggt     420
ggttctgctt ggcagtatga tgataagtcc gatcaatatt atttgcattt ttttagtaag    480
aagcagccag atctaaactg gaaaacgca aacttacgtc agaagattta tgatatgatg    540
aatttctgga ttgataaagg tattggcggc tttcggatgg acgtcattga tatgattggg    600
aaaattcctg ctcagcatat tgtcagtaac ggaccaaaat tgcatgctta tcttaaggag    660

-continued

```
atgaatgccg ctagttttgg tcaacatgat ctgctgactg tgggggaaac ttggggagca      720
acgcctgaga ttgcgaagca atattcaaat ccagtcaatc acgaactctc tatgattttt      780
caatttgaac atattggtct tcagcataaa ccagaagctc ctaaatggga ttatgtgaag      840
gaacttaatg ttcctgcttt aaaaacaatc tttaataaat ggcagactga gttggaatta      900
ggacaggggt ggaattcgtt attctggaat aaccatgacc tgcctcgtgt tttatcaatc      960
tggggaaata cggcaaata tcgtgagaag tctgctaaag cactggctat tcttcttcac     1020
cttatgcgtg ggacacctta tatttatcaa ggtgaagaga ttgggatgac caattatcct     1080
tttaaagatt taaatgaact tgatgatatt gaatcactta attatgctaa ggaagctttt     1140
acaaatggta agtctatgga aactatcatg gacagtattc gtatgattgg ccgtgataat     1200
gccagaacac ctatgcaatg ggatgcttct caaaatgccg attttcaac agcggataaa      1260 acatggctgc cagttaatcc aaactataaa gacatcaatg ttcaagcagc tctgaaaaat     1320
tccaattcta tcttttacac ctatcaacaa ctcattcagc ttcgaaaaga aaatgattgg     1380
ctagtagatg ccgattttga attgctccct acagcggaca agtatttgc ctatttacga      1440 aaggtaagag aagaaaggta tcttatagtg gtcaatgttt cagatcagga agaagttcta     1500
gagattgatg ttgacaaaca agaaactctc attagcaata caatgaaag cgctgctctt      1560 gccaatcaca aactccagcc ttgggatgct ttttgtatta agataaacta a              1611
```

<210> SEQ ID NO 17
<211> LENGTH: 536
<212> TYPE: PRT
<213> ORGANISM: Streptococcus mutans
<220> FEATURE:
<221> NAME/KEY: misc_feature
<223> OTHER INFORMATION: ATCC#25175D

<400> SEQUENCE: 17

```
Met Gln Lys His Trp Trp His Lys Ala Thr Val Tyr Gln Ile Tyr Pro
1               5                   10                  15

Lys Ser Phe Met Asp Thr Asn Gly Asp Gly Ile Gly Asp Leu Lys Gly
            20                  25                  30

Ile Thr Ser Lys Leu Asp Tyr Leu Gln Lys Leu Gly Val Met Ala Ile
        35                  40                  45

Trp Leu Ser Pro Val Tyr Asp Ser Pro Met Asp Asp Asn Gly Tyr Asp
    50                  55                  60

Ile Ala Asn Tyr Glu Ala Ile Ala Asp Ile Phe Gly Asn Met Ala Asp
65                  70                  75                  80

Met Asp Asn Leu Leu Thr Gln Ala Lys Met Arg Asp Ile Lys Ile Ile
                85                  90                  95

Met Asp Leu Val Val Asn His Thr Ser Asp Glu His Thr Trp Phe Ile
            100                 105                 110

Glu Ala Arg Glu His Pro Asp Ser Ser Glu Arg Asp Tyr Tyr Ile Trp
        115                 120                 125

Cys Asp Gln Pro Asn Asp Leu Glu Ser Ile Phe Gly Gly Ser Ala Trp
    130                 135                 140

Gln Tyr Asp Asp Lys Ser Asp Gln Tyr Tyr Leu His Phe Phe Ser Lys
145                 150                 155                 160

Lys Gln Pro Asp Leu Asn Trp Glu Asn Ala Asn Leu Arg Gln Lys Ile
                165                 170                 175

Tyr Asp Met Met Asn Phe Trp Ile Asp Lys Gly Ile Gly Gly Phe Arg
            180                 185                 190
```

```
Met Asp Val Ile Asp Met Ile Gly Lys Ile Pro Ala Gln His Ile Val
195                 200                 205

Ser Asn Gly Pro Lys Leu His Ala Tyr Leu Lys Glu Met Asn Ala Ala
210                 215                 220

Ser Phe Gly Gln His Asp Leu Leu Thr Val Gly Glu Thr Trp Gly Ala
225                 230                 235                 240

Thr Pro Glu Ile Ala Lys Gln Tyr Ser Asn Pro Val Asn His Glu Leu
245                 250                 255

Ser Met Ile Phe Gln Phe Glu His Ile Gly Leu Gln His Lys Pro Glu
260                 265                 270

Ala Pro Lys Trp Asp Tyr Val Lys Glu Leu Asn Val Pro Ala Leu Lys
275                 280                 285

Thr Ile Phe Asn Lys Trp Gln Thr Glu Leu Leu Gly Gln Gly Trp
290                 295                 300

Asn Ser Leu Phe Trp Asn Asn His Asp Leu Pro Arg Val Leu Ser Ile
305                 310                 315                 320

Trp Gly Asn Thr Gly Lys Tyr Arg Glu Lys Ser Ala Lys Ala Leu Ala
325                 330                 335

Ile Leu Leu His Leu Met Arg Gly Thr Pro Tyr Ile Tyr Gln Gly Glu
340                 345                 350

Glu Ile Gly Met Thr Asn Tyr Pro Phe Lys Asp Leu Asn Glu Leu Asp
355                 360                 365

Asp Ile Glu Ser Leu Asn Tyr Ala Lys Glu Ala Phe Thr Asn Gly Lys
370                 375                 380

Ser Met Glu Thr Ile Met Asp Ser Ile Arg Met Ile Gly Arg Asp Asn
385                 390                 395                 400

Ala Arg Thr Pro Met Gln Trp Asp Ala Ser Gln Asn Ala Gly Phe Ser
405                 410                 415

Thr Ala Asp Lys Thr Trp Leu Pro Val Asn Pro Asn Tyr Lys Asp Ile
420                 425                 430

Asn Val Gln Ala Ala Leu Lys Asn Ser Asn Ser Ile Phe Tyr Thr Tyr
435                 440                 445

Gln Gln Leu Ile Gln Leu Arg Lys Glu Asn Asp Trp Leu Val Asp Ala
450                 455                 460

Asp Phe Glu Leu Leu Pro Thr Ala Asp Lys Val Phe Ala Tyr Leu Arg
465                 470                 475                 480

Lys Val Arg Glu Glu Arg Tyr Leu Ile Val Val Asn Val Ser Asp Gln
485                 490                 495

Glu Glu Val Leu Glu Ile Asp Val Asp Lys Gln Glu Thr Leu Ile Ser
500                 505                 510

Asn Thr Asn Glu Ser Ala Ala Leu Ala Asn His Lys Leu Gln Pro Trp
515                 520                 525

Asp Ala Phe Cys Ile Lys Ile Asn
530                 535

<210> SEQ ID NO 18
<211> LENGTH: 35
<212> TYPE: DNA
<213> ORGANISM: artificial sequence
<220> FEATURE:
<223> OTHER INFORMATION: primer

<400> SEQUENCE: 18
tccgagctca tgggtttagg taagaaattg tctgt                          35
```

<210> SEQ ID NO 19
<211> LENGTH: 37
<212> TYPE: DNA
<213> ORGANISM: artificial sequence
<220> FEATURE:
<223> OTHER INFORMATION: primer

<400> SEQUENCE: 19
accttaatta aggttattcc ggatcggttt ccatggc                                37

<210> SEQ ID NO 20
<211> LENGTH: 89
<212> TYPE: DNA
<213> ORGANISM: artificial sequence
<220> FEATURE:
<223> OTHER INFORMATION: primer

<400> SEQUENCE: 20
gtgatagctg tcgtaaagct gttaccgact ggcgaagatt tcgccagtca cgtctaccct       60
tgttataccg tgtaggctgg agctgcttc                                         89

<210> SEQ ID NO 21
<211> LENGTH: 93
<212> TYPE: DNA
<213> ORGANISM: artificial sequence
<220> FEATURE:
<223> OTHER INFORMATION: primer

<400> SEQUENCE: 21
tcagaacagc cccaacggtt tatccgagta gctcaccagc aggcacttgg tttgctggta       60
atgctccagc ttattccgga tcggtttcca tgg                                    93

<210> SEQ ID NO 22
<211> LENGTH: 89
<212> TYPE: DNA
<213> ORGANISM: artificial sequence
<220> FEATURE:
<223> OTHER INFORMATION: primer

<400> SEQUENCE: 22
atgtcagtac ccgttcaaca tcctatgtat atcgatggac agtttgttac ctggcgtgga       60
gacgcatggg tgtaggctgg agctgcttc                                         89

<210> SEQ ID NO 23
<211> LENGTH: 93
<212> TYPE: DNA
<213> ORGANISM: artificial sequence
<220> FEATURE:
<223> OTHER INFORMATION: primer

<400> SEQUENCE: 23
ttaagactgt aaataaacca cctgggtctg cagatattca tgcaagccat gtttaccatc       60
tgcgccgcca ttattccgga tcggtttcca tgg                                    93

<210> SEQ ID NO 24
<211> LENGTH: 19
<212> TYPE: PRT
<213> ORGANISM: Artificial sequence
<220> FEATURE:
<223> OTHER INFORMATION: NPR signal

<400> SEQUENCE: 24

Met Asn Lys Glu Pro Thr Met Thr Thr Phe Asn Arg Thr Ile Pro Asp

```
                1               5                  10                 15

Ala Ile Arg

<210> SEQ ID NO 25
<211> LENGTH: 14
<212> TYPE: PRT
<213> ORGANISM: Artificial sequence
<220> FEATURE:
<223> OTHER INFORMATION: B. breve signal

<400> SEQUENCE: 25

Met Ser Leu Thr Ile Ser Leu Pro Gly Val Gln Ala Ser Ala
1               5                  10

<210> SEQ ID NO 26
<211> LENGTH: 62
<212> TYPE: DNA
<213> ORGANISM: Artificial sequence
<220> FEATURE:
<223> OTHER INFORMATION: B. breve signal

<400> SEQUENCE: 26
atgaataagg agccaacgat gactactttc aaccgcacaa taattcccga cgccattcgc      60
ac                                                                    62

<210> SEQ ID NO 27
<211> LENGTH: 42
<212> TYPE: DNA
<213> ORGANISM: artificial sequence
<220> FEATURE:
<223> OTHER INFORMATION: NPR signal

<400> SEQUENCE: 27
atgagtttaa ccatcagtct gccgggtgtt caggctagcg cg                         42

<210> SEQ ID NO 28
<211> LENGTH: 1877
<212> TYPE: DNA
<213> ORGANISM: Bifidobacterium breve

<400> SEQUENCE: 28
atgaataagg agccaacgat gactactttc aaccgcacaa taattcccga cgccattcgc      60
acatgaccgc caacaacctc aatgacgact ggtggaagca ggccgtcgtt taccagattt     120
acccgcgcag cttcaaggac gttaacggca acggcatcgg cgacatcgcc ggcgttaccg     180
agaaaatgga ctacctgaaa aacctcggcg tggacgccat ctggctctcc ccgttctacc     240
cctccgatct ggcggacggc ggctacgacg tgatcgacta ccgcaacgtc gacccgcgac     300
tgggcaccat ggacgacttc gacgccatgg ccaaagccgc gcatgaggcc ggcatcaagg     360
tgatcgtgga catcgtgccc aatcacaccg ccgacaagca cgtgttcttc aaggaagccc     420
tcgccgccga gcccggctcc ccggcgcgcg accgctacat cttccgcgac ggccgcggcg     480
agcacggcga actgccgccc aacgactggc agtccttctt cggcggcccg gcctgggctc     540
gcgtggccga cggccagtgg tatctgcacc tgttcgacaa ggcgcaaccg gacgtcaact     600
ggaagaaccc ggacatccac gaggaattca agaaaaccct gcgcttctgg tccgaccacg     660
gcaccgacgg cttccgcatc gacgtggcgc acggtctggc caaagacctt gaatccaagc     720
cgctggagga gctcgccgc gaatacagcg tggtcggcgt gctgaatcac gacttcagcc     780
atccgctgtt cgaccgccgc gaagtgcacg acatctaccg cgaatggcgc aaggtgttca     840
```

```
acgagtacga cccgccgcgc tttgccgtgg ccgaggcgtg ggtggtaccc gagcaccagc    900
acctgtatgc ctcgatggat gagctggggc agtccttcaa cttcgacttt gcgcaggcca    960
gctggtatgc cgatgagttc cgcgcagcca tcgccgcggg tctcaaggcc gctgccgaaa   1020
ccggcggttc caccaccacg tgggtgatga caaccatga cgtgccgcgc agcccctccc   1080
gctatggtct accgcaggtc aagggcgcgc cttaccacca gctgccgcac gactggctgc   1140
tgcgcaacgg caccacgtat cccgaggatc gcgagcttgg cacccgccgc gcccgcgccg   1200
ccgctttgat ggagctcggc ctgcccggcg ccgcctatat ctatcagggc gaggagctgg   1260
gcctgtttga agtggccgat attccgtggg atcgactgga agatccgacc gctttccaca   1320
ccgctcaggc cacgatggac aagggccgag acggctgccg cgtgccgatt ccgtggaccg   1380
ctgcaaacga accgaccttg gctgatttca gccgcccgat cccggccgat gacggcaccg   1440
gcgagaaacca cgtgccgctg tgcgccgccg gccagttcgg cacgggcgct tccttcggct   1500
tctcgccggc tacgcgcgct gagggcgtga cgccggccgc cgacccgcac ctgccgcagc   1560
cgttgtggtt caaggattac gcggtggacg tggagcaggc cgacccggat tcaatgctcg   1620
cgctgtatca tgcggcgttg gcgattcgtc aggagtcgct gaccgccacg cgtgacacca   1680
ccgctgagca ggtggatatg gggccggacg tggtggccta cacccgcgcg gcggttggtg   1740
gccgcacgtt cacctcgatc accaacttcg gcaccgagcc ggtggagctg cctggaggct   1800
ccgtcgtgct gacgtccggc ccgctgaccc ccgacggcca gctccccacc gacacttctg   1860
cgtgggttat caagtag                                                 1877

<210> SEQ ID NO 29
<211> LENGTH: 624
<212> TYPE: PRT
<213> ORGANISM: Bifidobacterium breve

<400> SEQUENCE: 29

Met Asn Lys Glu Pro Thr Met Thr Thr Phe Asn Arg Thr Ile Ile Pro
1               5                   10                  15

Asp Ala Ile Arg Met Thr Ala Asn Asn Leu Asn Asp Asp Trp Trp Lys
            20                  25                  30

Gln Ala Val Val Tyr Gln Ile Tyr Pro Arg Ser Phe Lys Asp Val Asn
        35                  40                  45

Gly Asp Gly Ile Gly Asp Ile Ala Gly Val Thr Glu Lys Met Asp Tyr
    50                  55                  60

Leu Lys Asn Leu Gly Val Asp Ala Ile Trp Leu Ser Pro Phe Tyr Pro
65                  70                  75                  80

Ser Asp Leu Ala Asp Gly Gly Tyr Asp Val Ile Asp Tyr Arg Asn Val
                85                  90                  95

Asp Pro Arg Leu Gly Thr Met Asp Asp Phe Asp Ala Met Ala Lys Ala
            100                 105                 110

Ala His Glu Ala Gly Ile Lys Val Ile Val Asp Ile Val Pro Asn His
        115                 120                 125

Thr Ala Asp Lys His Val Phe Phe Lys Glu Ala Leu Ala Ala Glu Pro
    130                 135                 140

Gly Ser Pro Ala Arg Asp Arg Tyr Ile Phe Arg Asp Gly Arg Gly Glu
145                 150                 155                 160

His Gly Glu Leu Pro Pro Asn Asp Trp Gln Ser Phe Phe Gly Gly Pro
                165                 170                 175

Ala Trp Ala Arg Val Ala Asp Gly Gln Trp Tyr Leu His Leu Phe Asp
            180                 185                 190
```

```
Lys Ala Gln Pro Asp Val Asn Trp Lys Asn Pro Asp Ile His Glu Glu
195                 200                 205

Phe Lys Lys Thr Leu Arg Phe Trp Ser Asp His Gly Thr Asp Gly Phe
210                 215                 220

Arg Ile Asp Val Ala His Gly Leu Ala Lys Asp Leu Glu Ser Lys Pro
225                 230                 235                 240

Leu Glu Glu Leu Gly Arg Glu Tyr Ser Val Val Gly Val Leu Asn His
245                 250                 255

Asp Phe Ser His Pro Leu Phe Asp Arg Arg Glu Val His Asp Ile Tyr
260                 265                 270

Arg Glu Trp Arg Lys Val Phe Asn Glu Tyr Asp Pro Pro Arg Phe Ala
275                 280                 285

Val Ala Glu Ala Trp Val Val Pro Glu His Gln His Leu Tyr Ala Ser
290                 295                 300

Met Asp Glu Leu Gly Gln Ser Phe Asn Phe Asp Phe Ala Gln Ala Ser
305                 310                 315                 320

Trp Tyr Ala Asp Glu Phe Arg Ala Ala Ile Ala Ala Gly Leu Lys Ala
325                 330                 335

Ala Ala Glu Thr Gly Gly Ser Thr Thr Thr Trp Val Met Asn Asn His
340                 345                 350

Asp Val Pro Arg Ser Pro Ser Arg Tyr Gly Leu Pro Gln Val Lys Gly
355                 360                 365

Ala Pro Tyr His Gln Leu Pro His Asp Trp Leu Leu Arg Asn Gly Thr
370                 375                 380

Thr Tyr Pro Glu Asp Arg Glu Leu Gly Thr Arg Arg Ala Arg Ala Ala
385                 390                 395                 400

Ala Leu Met Glu Leu Gly Leu Pro Gly Ala Ala Tyr Ile Tyr Gln Gly
405                 410                 415

Glu Glu Leu Gly Leu Phe Glu Val Ala Asp Ile Pro Trp Asp Arg Leu
420                 425                 430

Glu Asp Pro Thr Ala Phe His Thr Ala Gln Ala Thr Met Asp Lys Gly
435                 440                 445

Arg Asp Gly Cys Arg Val Pro Ile Pro Trp Thr Ala Ala Asn Glu Pro
450                 455                 460

Thr Leu Ala Asp Phe Ser Arg Pro Ile Pro Ala Asp Asp Gly Thr Gly
465                 470                 475                 480

Glu Asn His Val Pro Leu Cys Ala Ala Gly Gln Phe Gly Thr Gly Ala
485                 490                 495

Ser Phe Gly Phe Ser Pro Ala Thr Arg Ala Glu Gly Val Thr Pro Ala
500                 505                 510

Ala Asp Pro His Leu Pro Gln Pro Leu Trp Phe Lys Asp Tyr Ala Val
515                 520                 525

Asp Val Glu Gln Ala Asp Pro Asp Ser Met Leu Ala Leu Tyr His Ala
530                 535                 540

Ala Leu Ala Ile Arg Gln Glu Ser Leu Thr Ala Thr Arg Asp Thr Thr
545                 550                 555                 560

Ala Glu Gln Val Asp Met Gly Pro Asp Val Val Ala Tyr Thr Arg Ala
565                 570                 575

Ala Val Gly Gly Arg Thr Phe Thr Ser Ile Thr Asn Phe Gly Thr Glu
580                 585                 590

Pro Val Glu Leu Pro Gly Gly Ser Val Val Leu Thr Ser Gly Pro Leu
595                 600                 605
```

```
Thr Pro Asp Gly Gln Leu Pro Thr Asp Thr Ser Ala Trp Val Ile Lys
610                 615                 620
```

<210> SEQ ID NO 30
<211> LENGTH: 1611
<212> TYPE: DNA
<213> ORGANISM: Bifidobacterium breve

<400> SEQUENCE: 30

```
atgcaaaaac attggtggca caaggcaact gtttatcaaa tttatccaaa atcttttatg      60
gatacaaatg gtgatggaat tggtgatctc aaaggtatta cgagtaaatt ggattatttg     120
caaaagttag gggttatggc tatttggcta tctccagttt atgatagccc catggatgac     180
aatggctatg acattgcgaa ctatgaagca attgcggata ttttggcaa tatggctgat     240
atggataatt tgctgacgca ggcaaaaatg cgcgacataa aaatcattat ggatctagtg     300
gttaatcata cctcagatga acatacttgg tttattgaag cacgtgagca tccagacagt     360
tctgaacgcg attattatat ttggtgtgac cagccaaatg atttggaatc tattttcggt     420
ggttctgctt ggcagtatga tgataagtcc gatcaatatt atttgcattt ttttagtaag     480
aagcagccag atctaaactg ggaaaacgca aacttacgtc agaagattta tgatatgatg     540
aatttctgga ttgataaagg tattggcggc tttcggatgg acgtcattga tatgattggg     600
aaaattcctg ctcagcatat tgtcagtaac ggaccaaaat tgcatgctta tcttaaggag     660
atgaatgccg ctagttttgg tcaacatgat ctgctgactg tgggggaaac ttggggagca     720
acgcctgaga ttgcgaagca atattcaaat ccagtcaatc acgaactctc tatgattttt     780
caatttgaac atattggtct tcagcataaa ccagaagctc ctaaatggga ttatgtgaag     840
gaacttaatg ttcctgcttt aaaaacaatc tttaataaat ggcagactga gttggaatta     900
ggacagggt ggaattcgtt attctggaat aaccatgacc tgcctcgtgt tttatcaatc     960
tggggaaata cgggcaaata tcgtgagaag tctgctaaag cactggctat tcttcttcac    1020
cttatgcgtg ggacacctta tatttatcaa ggtgaagaga ttgggatgac caattatcct    1080
tttaaagatt taaatgaact tgatgatatt gaatcactta attatgctaa ggaagctttt    1140
acaaatggta agtctatgga aactatcatg gacagtattc gtatgattgg ccgtgataat    1200
gccagaacac ctatgcaatg ggatgcttct caaaatgccg gatttcaac agcggataaa    1260
acatggctgc cagttaatcc aaactataaa gacatcaatg ttcaagcagc tctgaaaaat    1320
tccaattcta tcttttacac ctatcaacaa ctcattcagc ttcgaaaaga aaatgattgg    1380
ctagtagatg ccgattttga attgctccct acagcggaca aagtatttgc ctatttacga    1440
aaggtaagag aagaaaggta tcttatagtg gtcaatgttt cagatcagga agaagttcta    1500
gagattgatg ttgacaaaca agaaactctc attagcaata caaatgaaag cgctgctctt    1560
gccaatcaca aactccagcc ttgggatgct ttttgtatta agataaacta a              1611
```

<210> SEQ ID NO 31
<211> LENGTH: 536
<212> TYPE: PRT
<213> ORGANISM: Bifidobacterium breve

<400> SEQUENCE: 31

```
Met Gln Lys His Trp Trp His Lys Ala Thr Val Tyr Gln Ile Tyr Pro
1               5                   10                  15

Lys Ser Phe Met Asp Thr Asn Gly Asp Gly Ile Gly Asp Leu Lys Gly
            20                  25                  30
```

-continued

```
Ile Thr Ser Lys Leu Asp Tyr Leu Gln Lys Leu Gly Val Met Ala Ile
 35                  40                  45
Trp Leu Ser Pro Val Tyr Asp Ser Pro Met Asp Asp Asn Gly Tyr Asp
 50                  55                  60
Ile Ala Asn Tyr Glu Ala Ile Ala Asp Ile Phe Gly Asn Met Ala Asp
 65                  70                  75                  80
Met Asp Asn Leu Leu Thr Gln Ala Lys Met Arg Asp Ile Lys Ile Ile
 85                  90                  95
Met Asp Leu Val Val Asn His Thr Ser Asp Glu His Thr Trp Phe Ile
100                 105                 110
Glu Ala Arg Glu His Pro Asp Ser Ser Glu Arg Asp Tyr Tyr Ile Trp
115                 120                 125
Cys Asp Gln Pro Asn Asp Leu Glu Ser Ile Phe Gly Gly Ser Ala Trp
130                 135                 140
Gln Tyr Asp Asp Lys Ser Asp Gln Tyr Tyr Leu His Phe Phe Ser Lys
145                 150                 155                 160
Lys Gln Pro Asp Leu Asn Trp Glu Asn Ala Asn Leu Arg Gln Lys Ile
165                 170                 175
Tyr Asp Met Met Asn Phe Trp Ile Asp Lys Gly Ile Gly Gly Phe Arg
180                 185                 190
Met Asp Val Ile Asp Met Ile Gly Lys Ile Pro Ala Gln His Ile Val
195                 200                 205
Ser Asn Gly Pro Lys Leu His Ala Tyr Leu Lys Glu Met Asn Ala Ala
210                 215                 220
Ser Phe Gly Gln His Asp Leu Leu Thr Val Gly Glu Thr Trp Gly Ala
225                 230                 235                 240
Thr Pro Glu Ile Ala Lys Gln Tyr Ser Asn Pro Val Asn His Glu Leu
245                 250                 255
Ser Met Ile Phe Gln Phe Glu His Ile Gly Leu Gln His Lys Pro Glu
260                 265                 270
Ala Pro Lys Trp Asp Tyr Val Lys Glu Leu Asn Val Pro Ala Leu Lys
275                 280                 285
Thr Ile Phe Asn Lys Trp Gln Thr Glu Leu Glu Leu Gly Gln Gly Trp
290                 295                 300
Asn Ser Leu Phe Trp Asn Asn His Asp Leu Pro Arg Val Leu Ser Ile
305                 310                 315                 320
Trp Gly Asn Thr Gly Lys Tyr Arg Glu Lys Ser Ala Lys Ala Leu Ala
325                 330                 335
Ile Leu Leu His Leu Met Arg Gly Thr Pro Tyr Ile Tyr Gln Gly Glu
340                 345                 350
Glu Ile Gly Met Thr Asn Tyr Pro Phe Lys Asp Leu Asn Glu Leu Asp
355                 360                 365
Asp Ile Glu Ser Leu Asn Tyr Ala Lys Glu Ala Phe Thr Asn Gly Lys
370                 375                 380
Ser Met Glu Thr Ile Met Asp Ser Ile Arg Met Ile Gly Arg Asp Asn
385                 390                 395                 400
Ala Arg Thr Pro Met Gln Trp Asp Ala Ser Gln Asn Ala Gly Phe Ser
405                 410                 415
Thr Ala Asp Lys Thr Trp Leu Pro Val Asn Pro Asn Tyr Lys Asp Ile
420                 425                 430
Asn Val Gln Ala Ala Leu Lys Asn Ser Asn Ser Ile Phe Tyr Thr Tyr
435                 440                 445
Gln Gln Leu Ile Gln Leu Arg Lys Glu Asn Asp Trp Leu Val Asp Ala
```

```
                450               455               460
Asp Phe Glu Leu Leu Pro Thr Ala Asp Lys Val Phe Ala Tyr Leu Arg
465               470               475               480

Lys Val Arg Glu Glu Arg Tyr Leu Ile Val Val Asn Val Ser Asp Gln
485               490               495

Glu Glu Val Leu Glu Ile Asp Val Asp Lys Gln Glu Thr Leu Ile Ser
500               505               510

Asn Thr Asn Glu Ser Ala Ala Leu Ala Asn His Lys Leu Gln Pro Trp
515               520               525

Asp Ala Phe Cys Ile Lys Ile Asn
530               535

<210> SEQ ID NO 32
<211> LENGTH: 1880
<212> TYPE: DNA
<213> ORGANISM: Bifidobacterium breve

<400> SEQUENCE: 32
atgaataagg agccaacgat gactactttc aaccgcacaa taattcccga cgccattcgc    60
acatgatgac ctcttcaac cgtgaacccc tgcccgacgc cgtccgcacg aatggcgcct    120
ccccgaaccc gtggtggtcg aacgccgtcg tctaccagat ttacccacgt tccttccagg    180
acacgaacgg cgatggtttc ggagatctta agggcattac ttcccgcctc gactatcttg    240
ccgacctcgg cgtggatgtg ctgtggctct ccccggtcta caggtccccg caagacgaca    300
acggctacga catctccgac taccgggaca tcgacccgct gttcggcacg ctcgacgaca    360
tggacgagct gctcgccgaa gcgcacaagc gcggcctcaa gatcgtgatg gacctggtcg    420
tcaaccacac ctccgacgag cacgcgtggt tcgaggcgtc gaaggacaag gacgacccgc    480
acgccgactg gtactggtgg cgtcccgccc gccccggcca cgagcccggc acgcccggcg    540
ccgagccgaa ccagtggggc tcctacttcg gcggctccgc atgggaatat tgccccgagc    600
gtggtgagta ctatctccac cagttctcga agaagcagcc ggacctcaac tgggagaacc    660
cggccgtacg ccgagccgtg tacgacatga tgaactggtg gctcgatcgc ggcatcgacg    720
gcttccgcat ggacgtcatc accctgatct ccaagcgcac ggatgcaaac ggcaggctgc    780
ccggcgagac cggttccgag ctgcaggacc tgccggtggg ggaggagggc tactccaacc    840
cgaacccgtt ctgcgccgac ggtccgcgtc aggacgagtt cctcgccgag atgcgccgcg    900
aggtgttcga cgggcgtgac ggcttcctca cgtcggcga ggcccccggc atcaccgccg    960
aacgcaacga gcacatcacc gaccccgcca acggcgagct ggatatgctc ttcctgttcg    1020
aacacatggg cgtcgaccaa cccccgaat cgaaatggga cgacaaacca tggacgccgg    1080
ccgacctcga aaccaagctc gccgaacaac aggacgccat cgcccgacac ggctgggcca    1140
gcctgttcct cgacaaccac gaccagccgc gtgtcgtctc ccgttggggc gacgacacca    1200
gcaagaccgg ccgcatccgc tccgccaagg cgctcgcgct gctgctgcac atgcaccgcg    1260
gcactccgta tgtctaccag ggcgaggagc tcggcatgac caatgcgcac ttcacctcgc    1320
tcgaccagta ccgcgacctc gaatccatca acgcctacca tcaacgcgtc gaggaaaccg    1380
ggatacggac atcggagacc atgatgcgat ccctcgcccg atacggcagg acaacgcgc    1440 gcaccccgat gcaatgggac gactccacct acgccggctt caccatgccc gacgcccgg    1500 tcgaaccctg gatcgccgtc aacccgaacc acacggagat caacgccgcc gacgagatcg    1560 acgacccga ctccgtgtac tcgttccaca acggctcat cgccctgcgt cacaccgacc    1620
```

-continued

```
ccgtggtcgc cgccggcgac taccgacgcg tggaaaccgg aaacgaccgg atcatcgcct    1680
tcaccagaac cctcgacgag cgaaccatcc tcaccgtcat caacctctcg cccacacagg    1740
ccgcaccggc cggagaactg gaaacgatgc ccgacggcac gatcctcatc gccaacacgg    1800
acgatcccgt aggaaacctg aaaaccacgg gaacactcgg accatgggag gcgttcgcca    1860
tggaaaccga tccggaataa                                                1880
```

```
<210> SEQ ID NO 33
<211> LENGTH: 625
<212> TYPE: PRT
<213> ORGANISM: Bifidobacterium breve

<400> SEQUENCE: 33

Met Asn Lys Glu Pro Thr Met Thr Thr Phe Asn Arg Thr Ile Ile Pro
1               5                   10                  15

Asp Ala Ile Arg Met Met Thr Ser Phe Asn Arg Glu Pro Leu Pro Asp
            20                  25                  30

Ala Val Arg Thr Asn Gly Ala Ser Pro Asn Trp Trp Ser Asn Ala
        35                  40                  45

Val Val Tyr Gln Ile Tyr Pro Arg Ser Phe Gln Asp Thr Asn Gly Asp
    50                  55                  60

Gly Phe Gly Asp Leu Lys Gly Ile Thr Ser Arg Leu Asp Tyr Leu Ala
65                  70                  75                  80

Asp Leu Gly Val Asp Val Leu Trp Leu Ser Pro Val Tyr Arg Ser Pro
                85                  90                  95

Gln Asp Asp Asn Gly Tyr Asp Ile Ser Asp Tyr Arg Asp Ile Asp Pro
            100                 105                 110

Leu Phe Gly Thr Leu Asp Asp Met Asp Glu Leu Leu Ala Glu Ala His
        115                 120                 125

Lys Arg Gly Leu Lys Ile Val Met Asp Leu Val Val Asn His Thr Ser
    130                 135                 140

Asp Glu His Ala Trp Phe Glu Ala Ser Lys Asp Lys Asp Pro His
145                 150                 155                 160

Ala Asp Trp Tyr Trp Trp Arg Pro Ala Arg Pro Gly His Glu Pro Gly
                165                 170                 175

Thr Pro Gly Ala Glu Pro Asn Gln Trp Gly Ser Tyr Phe Gly Gly Ser
            180                 185                 190

Ala Trp Glu Tyr Cys Pro Glu Arg Gly Glu Tyr Tyr Leu His Gln Phe
        195                 200                 205

Ser Lys Lys Gln Pro Asp Leu Asn Trp Glu Asn Pro Ala Val Arg Arg
    210                 215                 220

Ala Val Tyr Asp Met Met Asn Trp Trp Leu Asp Arg Gly Ile Asp Gly
225                 230                 235                 240

Phe Arg Met Asp Val Ile Thr Leu Ile Ser Lys Arg Thr Asp Ala Asn
                245                 250                 255

Gly Arg Leu Pro Gly Glu Thr Gly Ser Glu Leu Gln Asp Leu Pro Val
            260                 265                 270

Gly Glu Glu Gly Tyr Ser Asn Pro Asn Pro Phe Cys Ala Asp Gly Pro
        275                 280                 285

Arg Gln Asp Glu Phe Leu Ala Glu Met Arg Arg Glu Val Phe Asp Gly
    290                 295                 300

Arg Asp Gly Phe Leu Thr Val Gly Glu Ala Pro Gly Ile Thr Ala Glu
305                 310                 315                 320

Arg Asn Glu His Ile Thr Asp Pro Ala Asn Gly Glu Leu Asp Met Leu
```

-continued

```
                325                 330                 335
        Phe Leu Phe Glu His Met Gly Val Asp Gln Thr Pro Glu Ser Lys Trp
        340                 345                 350

Asp Asp Lys Pro Trp Thr Pro Ala Asp Leu Glu Thr Lys Leu Ala Glu
        355                 360                 365

Gln Gln Asp Ala Ile Ala Arg His Gly Trp Ala Ser Leu Phe Leu Asp
        370                 375                 380

Asn His Asp Gln Pro Arg Val Val Ser Arg Trp Gly Asp Asp Thr Ser
        385                 390                 395                 400

Lys Thr Gly Arg Ile Arg Ser Ala Lys Ala Leu Ala Leu Leu Leu His
        405                 410                 415

Met His Arg Gly Thr Pro Tyr Val Tyr Gln Gly Glu Glu Leu Gly Met
        420                 425                 430

Thr Asn Ala His Phe Thr Ser Leu Asp Gln Tyr Arg Asp Leu Glu Ser
        435                 440                 445

Ile Asn Ala Tyr His Gln Arg Val Glu Glu Thr Gly Ile Arg Thr Ser
        450                 455                 460

Glu Thr Met Met Arg Ser Leu Ala Arg Tyr Gly Arg Asp Asn Ala Arg
        465                 470                 475                 480

Thr Pro Met Gln Trp Asp Asp Ser Thr Tyr Ala Gly Phe Thr Met Pro
        485                 490                 495

Asp Ala Pro Val Glu Pro Trp Ile Ala Val Asn Pro Asn His Thr Glu
        500                 505                 510

Ile Asn Ala Ala Asp Glu Ile Asp Asp Pro Asp Ser Val Tyr Ser Phe
        515                 520                 525

His Lys Arg Leu Ile Ala Leu Arg His Thr Asp Pro Val Val Ala Ala
        530                 535                 540

Gly Asp Tyr Arg Arg Val Glu Thr Gly Asn Asp Arg Ile Ile Ala Phe
        545                 550                 555                 560

Thr Arg Thr Leu Asp Glu Arg Thr Ile Leu Thr Val Ile Asn Leu Ser
        565                 570                 575

Pro Thr Gln Ala Ala Pro Ala Gly Glu Leu Glu Thr Met Pro Asp Gly
        580                 585                 590

Thr Ile Leu Ile Ala Asn Thr Asp Asp Pro Val Gly Asn Leu Lys Thr
        595                 600                 605

Thr Gly Thr Leu Gly Pro Trp Glu Ala Phe Ala Met Glu Thr Asp Pro
        610                 615                 620

Glu
        625

<210> SEQ ID NO 34
<211> LENGTH: 1673
<212> TYPE: DNA
<213> ORGANISM: Artificial sequence
<220> FEATURE:
<223> OTHER INFORMATION: Bifidobacterium breve gene mbc2g.pk018.j20
      signal peptide linkedto the coding sequence for the
      Streptococcus mutans dexB gene

<400> SEQUENCE: 34
atgaataagg agccaacgat gactactttc aaccgcacaa taattcccga cgccattcgc    60
acatgcaaaa acattggtgg cacaaggcaa ctgtttatca aatttatcca aaatctttta   120
tggatacaaa tggtgatgga attggtgatc tcaaaggtat tacgagtaaa ttggattatt   180
tgcaaaagtt aggggttatg ctatttggc tatctccagt ttatgatagc cccatggatg   240
```

```
acaatggcta tgacattgcg aactatgaag caattgcgga tattttggc aatatggctg    300
atatggataa tttgctgacg caggcaaaaa tgcgcgacat aaaaatcatt atggatctag   360
tggttaatca tacctcagat gaacatactt ggtttattga agcacgtgag catccagaca   420
gttctgaacg cgattattat atttggtgtg accagccaaa tgatttggaa tctattttcg   480
gtggttctgc ttggcagtat gatgataagt ccgatcaata ttatttgcat ttttttagta   540
agaagcagcc agatctaaac tgggaaaacg caaacttacg tcagaagatt tatgatatga   600
tgaatttctg gattgataaa ggtattggcg gctttcggat ggacgtcatt gatatgattg   660
ggaaaattcc tgctcagcat attgtcagta acggaccaaa attgcatgct tatcttaagg   720
agatgaatgc cgctagtttt ggtcaacatg atctgctgac tgtgggggaa acttggggag   780
caacgcctga gattgcgaag caatattcaa atccagtcaa tcacgaactc tctatgattt   840
ttcaatttga acatattggt cttcagcata accagaagc tcctaaatgg gattatgtga    900
aggaacttaa tgttcctgct ttaaaaacaa tctttaataa atggcagact gagttggaat   960
taggacaggg gtggaattcg ttattctgga ataaccatga cctgcctcgt gttttatcaa  1020
tctggggaaa tacgggcaaa tatcgtgaga agtctgctaa agcactggct attcttcttc  1080
accttatgcg tgggacacct tatatttatc aaggtgaaga gattgggatg accaattatc  1140
cttttaaaga tttaaatgaa cttgatgata ttgaatcact taattatgct aaggaagctt  1200
ttacaaatgg taagtctatg gaaactatca tggacagtat tcgtatgatt ggccgtgata  1260
atgccagaac acctatgcaa tgggatgctt ctcaaaatgc cggattttca acagcggata  1320
aaacatggct gccagttaat ccaaactata agacatcaa tgttcaagca gctctgaaaa   1380
attccaattc tatcttttac acctatcaac aactcattca gcttcgaaaa gaaaatgatt  1440
ggctagtaga tgccgatttt gaattgctcc ctacagcgga caagtatttt gcctatttac  1500
gaaaggtaag agaagaaagg tatcttatag tggtcaatgt ttcagatcag gaagaagttc  1560
tagagattga tgttgacaaa caagaaactc tcattagcaa tacaaatgaa agcgctgctc  1620
ttgccaatca caactccag ccttgggatg cttttttgtat taagataaac taa         1673
```

<210> SEQ ID NO 35
<211> LENGTH: 556
<212> TYPE: PRT
<213> ORGANISM: Artificial sequence
<220> FEATURE:
<223> OTHER INFORMATION: Bifidobacterium breve gene mbc2g.pk018.j20
      signal peptide linkedto the coding sequence for the
      Streptococcus mutans dexB gene

<400> SEQUENCE: 35

Met Asn Lys Glu Pro Thr Met Thr Thr Phe Asn Arg Thr Ile Ile Pro
1               5                   10                  15

Asp Ala Ile Arg Met Gln Lys His Trp Trp His Lys Ala Thr Val Tyr
            20                  25                  30

Gln Ile Tyr Pro Lys Ser Phe Met Asp Thr Asn Gly Asp Gly Ile Gly
        35                  40                  45

Asp Leu Lys Gly Ile Thr Ser Lys Leu Asp Tyr Leu Gln Lys Leu Gly
    50                  55                  60

Val Met Ala Ile Trp Leu Ser Pro Val Tyr Asp Ser Pro Met Asp Asp
65                  70                  75                  80

Asn Gly Tyr Asp Ile Ala Asn Tyr Glu Ala Ile Ala Asp Ile Phe Gly
                85                  90                  95

Asn Met Ala Asp Met Asp Asn Leu Leu Thr Gln Ala Lys Met Arg Asp

-continued

```
                100             105             110
Ile Lys Ile Ile Met Asp Leu Val Val Asn His Thr Ser Asp Glu His
115             120             125

Thr Trp Phe Ile Glu Ala Arg Glu His Pro Asp Ser Ser Glu Arg Asp
130             135             140

Tyr Tyr Ile Trp Cys Asp Gln Pro Asn Asp Leu Glu Ser Ile Phe Gly
145             150             155             160

Gly Ser Ala Trp Gln Tyr Asp Asp Lys Ser Asp Gln Tyr Tyr Leu His
165             170             175

Phe Phe Ser Lys Lys Gln Pro Asp Leu Asn Trp Glu Asn Ala Asn Leu
180             185             190

Arg Gln Lys Ile Tyr Asp Met Met Asn Phe Trp Ile Asp Lys Gly Ile
195             200             205

Gly Gly Phe Arg Met Asp Val Ile Asp Met Ile Gly Lys Ile Pro Ala
210             215             220

Gln His Ile Val Ser Asn Gly Pro Lys Leu His Ala Tyr Leu Lys Glu
225             230             235             240

Met Asn Ala Ala Ser Phe Gly Gln His Asp Leu Leu Thr Val Gly Glu
245             250             255

Thr Trp Gly Ala Thr Pro Glu Ile Ala Lys Gln Tyr Ser Asn Pro Val
260             265             270

Asn His Glu Leu Ser Met Ile Phe Gln Phe Glu His Ile Gly Leu Gln
275             280             285

His Lys Pro Glu Ala Pro Lys Trp Asp Tyr Val Lys Glu Leu Asn Val
290             295             300

Pro Ala Leu Lys Thr Ile Phe Asn Lys Trp Gln Thr Glu Leu Glu Leu
305             310             315             320

Gly Gln Gly Trp Asn Ser Leu Phe Trp Asn Asn His Asp Leu Pro Arg
325             330             335

Val Leu Ser Ile Trp Gly Asn Thr Gly Lys Tyr Arg Glu Lys Ser Ala
340             345             350

Lys Ala Leu Ala Ile Leu Leu His Leu Met Arg Gly Thr Pro Tyr Ile
355             360             365

Tyr Gln Gly Glu Glu Ile Gly Met Thr Asn Tyr Pro Phe Lys Asp Leu
370             375             380

Asn Glu Leu Asp Asp Ile Glu Ser Leu Asn Tyr Ala Lys Glu Ala Phe
385             390             395             400

Thr Asn Gly Lys Ser Met Glu Thr Ile Asp Ser Ile Arg Met Ile
405             410             415

Gly Arg Asp Asn Ala Arg Thr Pro Met Gln Trp Asp Ala Ser Gln Asn
420             425             430

Ala Gly Phe Ser Thr Ala Asp Lys Thr Trp Leu Pro Val Asn Pro Asn
435             440             445

Tyr Lys Asp Ile Asn Val Gln Ala Ala Leu Lys Asn Ser Asn Ser Ile
450             455             460

Phe Tyr Thr Tyr Gln Gln Leu Ile Gln Leu Arg Lys Glu Asn Asp Trp
465             470             475             480

Leu Val Asp Ala Asp Phe Glu Leu Leu Pro Thr Ala Asp Lys Val Phe
485             490             495

Ala Tyr Leu Arg Lys Val Arg Glu Glu Arg Tyr Leu Ile Val Val Asn
500             505             510

Val Ser Asp Gln Glu Glu Val Leu Glu Ile Asp Val Asp Lys Gln Glu
515             520             525
```

```
Thr Leu Ile Ser Asn Thr Asn Glu Ser Ala Ala Leu Ala Asn His Lys
530                 535                 540

Leu Gln Pro Trp Asp Ala Phe Cys Ile Lys Ile Asn
545                 550                 555

<210> SEQ ID NO 36
<211> LENGTH: 1857
<212> TYPE: DNA
<213> ORGANISM: Artificial sequence
<220> FEATURE:
<223> OTHER INFORMATION: Bacillus subtilis neutral protease gene
      signal peptide linked to the coding sequence for the
      Bifidobacterium breve mbc2g.pk018.h12gene

<400> SEQUENCE: 36
atgagtttaa ccatcagtct gccgggtgtt caggctagcg cgatgaccgc caacaacctc      60
aatgacgact ggtggaagca ggccgtcgtt taccagattt acccgcgcag cttcaaggac     120
gttaacggcg acggcatcgg cgacatcgcc ggcgttaccg agaaaatgga ctacctgaaa     180
aacctcggcg tggacgccat ctggctctcc ccgttctacc cctccgatct ggcggacggc     240
ggctacgacg tgatcgacta ccgcaacgtc gacccgcgac tgggcaccat ggacgacttc     300
gacgccatgg ccaaagccgc gcatgaggcc ggcatcaagg tgatcgtgga catcgtgccc     360
aatcacaccg ccgacaagca cgtgttcttc aaggaagccc tcgccgccga gcccggctcc     420
ccggcgcgcg accgctacat cttccgcgac ggccgcggcg agcacggcga actgccgccc     480
aacgactggc agtccttctt cggcggcccg gcctgggctc gcgtggccga cggccagtgg     540
tatctgcacc tgttcgacaa ggcgcaaccg gacgtcaact ggaagaaccc ggacatccac     600
gaggaattca gaaaacccct gcgcttctgg tccgaccacg gcaccgacgg cttccgcatc     660
gacgtggcgc acggtctggc caaagacctt gaatccaagc cgctggagga gctcggccgc     720
gaatacagcg tggtcggcgt gctgaatcac gacttcagcc atccgctgtt cgaccgccgc     780
gaagtgcacg acatctaccg gaatggcgcg aaggtgttca cgagtacgac ccgccgcgc      840 tttgccgtgg ccgaggcgtg ggtggtaccc gagcaccagc acctgtatgc ctcgatggat     900
gagctggggc agtccttcaa cttcgacttt gcgcaggcca gctggtatgc cgatgagttc     960
cgcgcagcca tcgccgcggg tctcaaggcc gctgccgaaa ccggcggttc caccaccacg    1020
tgggtgatga acaaccatga cgtgccgcgc agcccctccc gctatggtct accgcaggtc    1080
aagggcgcgc cttaccacca gctgccgcac gactggctgc tgcgcaacgg caccacgtat    1140
cccgaggatc gcgagcttgg caccgccgc gcccgcgccg ccgctttgat ggagctcggc    1200
ctgcccggcg ccgcctatat ctatcagggc gaggagctgg gcctgtttga agtggccgat    1260
attccgtggg atcgactgga agatccgacc gctttccaca ccgctcaggc cacgatggac    1320
aagggccgag acggctgccg cgtgccgatt ccgtggaccg ctgcaaacga accgaccttg    1380
gctgatttca gccgcccgat cccggccgat gacggcaccg gcgagaacca cgtgccgctg    1440
tgcgccgccg gccagttcgg cacgggcgct tccttcggct tctcgccggc tacgcgcgct    1500
gagggcgtga cgccggccgc cgacccgcac ctgccgcagc cgttgtggtt caaggattac    1560
gcggtggacg tggagcaggc cgacccggat tcaatgctcg cgctgtatca tgcggcgttg    1620
gcgattcgtc aggagtcgct gaccgccacg cgtgacacca ccgctgagca ggtggatatg    1680 gggccgacg tggtggccta caccgcgcg cggttggtg ccgcacgtt cacctcgatc        1740 accaacttcg gcaccgagcc ggtggagctg cctggaggct ccgtcgtgct gacgtccggc    1800
```
ccgctgaccc cgacggcca gctccccacc gacacttctg cgtgggttat caagtag    1857

<210> SEQ ID NO 37
<211> LENGTH: 618
<212> TYPE: PRT
<213> ORGANISM: Artificial sequence
<220> FEATURE:
<223> OTHER INFORMATION: Bacillus subtilis neutral protease gene signal
      peptide linked tothe coding sequence for the Bifidobacterium
      breve mbc2g.pk018.h12gene

<400> SEQUENCE: 37

```
Met Ser Leu Thr Ile Ser Leu Pro Gly Val Gln Ala Ser Ala Met Thr
1               5                   10                  15

Ala Asn Asn Leu Asn Asp Asp Trp Trp Lys Gln Ala Val Val Tyr Gln
            20                  25                  30

Ile Tyr Pro Arg Ser Phe Lys Asp Val Asn Gly Asp Gly Ile Gly Asp
        35                  40                  45

Ile Ala Gly Val Thr Glu Lys Met Asp Tyr Leu Lys Asn Leu Gly Val
    50                  55                  60

Asp Ala Ile Trp Leu Ser Pro Phe Tyr Pro Ser Asp Leu Ala Asp Gly
65                  70                  75                  80

Gly Tyr Asp Val Ile Asp Tyr Arg Asn Val Asp Pro Arg Leu Gly Thr
                85                  90                  95

Met Asp Asp Phe Asp Ala Met Ala Lys Ala Ala His Glu Ala Gly Ile
            100                 105                 110

Lys Val Ile Val Asp Ile Val Pro Asn His Thr Ala Asp Lys His Val
        115                 120                 125

Phe Phe Lys Glu Ala Leu Ala Ala Glu Pro Gly Ser Pro Ala Arg Asp
    130                 135                 140

Arg Tyr Ile Phe Arg Asp Gly Arg Gly Glu His Gly Glu Leu Pro Pro
145                 150                 155                 160

Asn Asp Trp Gln Ser Phe Phe Gly Gly Pro Ala Trp Ala Arg Val Ala
                165                 170                 175

Asp Gly Gln Trp Tyr Leu His Leu Phe Asp Lys Ala Gln Pro Asp Val
            180                 185                 190

Asn Trp Lys Asn Pro Asp Ile His Glu Glu Phe Lys Lys Thr Leu Arg
        195                 200                 205

Phe Trp Ser Asp His Gly Thr Asp Gly Phe Arg Ile Asp Val Ala His
    210                 215                 220

Gly Leu Ala Lys Asp Leu Glu Ser Lys Pro Leu Glu Glu Leu Gly Arg
225                 230                 235                 240

Glu Tyr Ser Val Val Gly Val Leu Asn His Asp Phe Ser His Pro Leu
                245                 250                 255

Phe Asp Arg Arg Glu Val His Asp Ile Tyr Arg Glu Trp Arg Lys Val
            260                 265                 270

Phe Asn Glu Tyr Asp Pro Pro Arg Phe Ala Val Ala Glu Ala Trp Val
        275                 280                 285

Val Pro Glu His Gln His Leu Tyr Ala Ser Met Asp Glu Leu Gly Gln
    290                 295                 300

Ser Phe Asn Phe Asp Phe Ala Gln Ala Ser Trp Tyr Ala Asp Glu Phe
305                 310                 315                 320

Arg Ala Ala Ile Ala Ala Gly Leu Lys Ala Ala Glu Thr Gly Gly
                325                 330                 335

Ser Thr Thr Thr Trp Val Met Asn Asn His Asp Val Pro Arg Ser Pro
            340                 345                 350
```

```
Ser Arg Tyr Gly Leu Pro Gln Val Lys Gly Ala Pro Tyr His Gln Leu
355                 360                 365

Pro His Asp Trp Leu Leu Arg Asn Gly Thr Thr Tyr Pro Glu Asp Arg
370                 375                 380

Glu Leu Gly Thr Arg Arg Ala Arg Ala Ala Ala Leu Met Glu Leu Gly
385                 390                 395                 400

Leu Pro Gly Ala Ala Tyr Ile Tyr Gln Gly Glu Glu Leu Gly Leu Phe
405                 410                 415

Glu Val Ala Asp Ile Pro Trp Asp Arg Leu Glu Asp Pro Thr Ala Phe
420                 425                 430

His Thr Ala Gln Ala Thr Met Asp Lys Gly Arg Asp Gly Cys Arg Val
435                 440                 445

Pro Ile Pro Trp Thr Ala Ala Asn Glu Pro Thr Leu Ala Asp Phe Ser
450                 455                 460

Arg Pro Ile Pro Ala Asp Asp Gly Thr Gly Glu Asn His Val Pro Leu
465                 470                 475                 480

Cys Ala Ala Gly Gln Phe Gly Thr Gly Ala Ser Phe Gly Phe Ser Pro
485                 490                 495

Ala Thr Arg Ala Glu Gly Val Thr Pro Ala Ala Asp Pro His Leu Pro
500                 505                 510

Gln Pro Leu Trp Phe Lys Asp Tyr Ala Val Asp Val Glu Gln Ala Asp
515                 520                 525

Pro Asp Ser Met Leu Ala Leu Tyr His Ala Ala Leu Ala Ile Arg Gln
530                 535                 540

Glu Ser Leu Thr Ala Thr Arg Asp Thr Thr Ala Glu Gln Val Asp Met
545                 550                 555                 560

Gly Pro Asp Val Val Ala Tyr Thr Arg Ala Ala Val Gly Gly Arg Thr
565                 570                 575

Phe Thr Ser Ile Thr Asn Phe Gly Thr Glu Pro Val Glu Leu Pro Gly
580                 585                 590

Gly Ser Val Val Leu Thr Ser Gly Pro Leu Thr Pro Asp Gly Gln Leu
595                 600                 605

Pro Thr Asp Thr Ser Ala Trp Val Ile Lys
610                 615

<210> SEQ ID NO 38
<211> LENGTH: 1653
<212> TYPE: DNA
<213> ORGANISM: Artificial sequence
<220> FEATURE:
<223> OTHER INFORMATION: Bacillus subtilis neutral protease gene
      signal peptide linked to the coding sequence for the
      Bifidobacterium breve mbc2g.pk018.j20gene

<400> SEQUENCE: 38
atgagtttaa ccatcagtct gccgggtgtt caggctagcg cgatgcaaaa acattggtgg      60
cacaaggcaa ctgtttatca aatttatcca aatctttta tggatacaaa tggtgatgga     120
attggtgatc tcaaaggtat tacgagtaaa ttggattatt tgcaaaagtt aggggttatg     180
gctatttggc tatctccagt ttatgatagc cccatggatg acaatggcta tgacattgcg     240
aactatgaag caattgcgga tattttggc aatatggctg atatggataa tttgctgacg     300
caggcaaaaa tgcgcgacat aaaaatcatt atggatctag tggttaatca tacctcagat     360
gaacatactt ggtttattga agcacgtgag catccagaca gttctgaacg cgattattat     420
atttggtgtg accagccaaa tgatttggaa tctatttcg gtggttctgc ttggcagtat     480
```

```
gatgataagt ccgatcaata ttatttgcat tttttagta agaagcagcc agatctaaac    540
tgggaaaacg caaacttacg tcagaagatt tatgatatga tgaatttctg gattgataaa    600
ggtattggcg gctttcggat ggacgtcatt gatatgattg ggaaaattcc tgctcagcat    660
attgtcagta acggaccaaa attgcatgct tatcttaagg agatgaatgc cgctagtttt    720
ggtcaacatg atctgctgac tgtgggggaa acttggggag caacgcctga gattgcgaag    780
caatattcaa atccagtcaa tcacgaactc tctatgattt ttcaatttga acatattggt    840
cttcagcata aaccagaagc tcctaaatgg gattatgtga aggaacttaa tgttcctgct    900
ttaaaaacaa tctttaataa atggcagact gagttggaat taggacaggg gtggaattcg    960
ttattctgga taaccatga cctgcctcgt gttttatcaa tctggggaaa tacgggcaaa   1020
tatcgtgaga agtctgctaa agcactggct attcttcttc accttatgcg tgggacacct   1080
tatatttatc aaggtgaaga gattgggatg accaattatc ctttaaaga tttaaatgaa   1140 cttgatgata ttgaatcact taattatgct aaggaagctt ttacaaatgg taagtctatg   1200
gaaactatca tggacagtat tcgtatgatt ggccgtgata atgccagaac acctatgcaa   1260
tgggatgctt ctcaaaatgc cggatttca acagcggata aaacatggct gccagttaat   1320
ccaaactata aagacatcaa tgttcaagca gctctgaaaa attccaattc tatcttttac   1380
acctatcaac aactcattca gcttcgaaaa gaaaatgatt ggctagtaga tgccgatttt   1440
gaattgctcc ctacagcgga caaagtattt gcctatttac gaaaggtaag agaagaaagg   1500
tatcttatag tggtcaatgt ttcagatcag gaagaagttc tagagattga tgttgacaaa   1560
caagaaactc tcattagcaa tacaaatgaa agcgctgctc ttgccaatca caaactccag   1620
ccttgggatg cttttttgtat taagataaac taa                               1653
```

<210> SEQ ID NO 39
<211> LENGTH: 550
<212> TYPE: PRT
<213> ORGANISM: Artificial sequence
<220> FEATURE:
<223> OTHER INFORMATION: Bacillus subtilis neutral protease gene
      signal peptide linked to the coding sequence for the
      Bifidobacterium breve mbc2g.pk018.j20gene

<400> SEQUENCE: 39

Met Ser Leu Thr Ile Ser Leu Pro Gly Val Gln Ala Ser Ala Met Gln
1               5                   10                  15

Lys His Trp Trp His Lys Ala Thr Val Tyr Gln Ile Tyr Pro Lys Ser
            20                  25                  30

Phe Met Asp Thr Asn Gly Asp Gly Ile Gly Asp Leu Lys Gly Ile Thr
        35                  40                  45

Ser Lys Leu Asp Tyr Leu Gln Lys Leu Gly Val Met Ala Ile Trp Leu
    50                  55                  60

Ser Pro Val Tyr Asp Ser Pro Met Asp Asp Asn Gly Tyr Asp Ile Ala
65                  70                  75                  80

Asn Tyr Glu Ala Ile Ala Asp Ile Phe Gly Asn Met Ala Asp Met Asp
                85                  90                  95

Asn Leu Leu Thr Gln Ala Lys Met Arg Asp Ile Lys Ile Ile Met Asp
            100                 105                 110

Leu Val Val Asn His Thr Ser Asp Glu His Thr Trp Phe Ile Glu Ala
        115                 120                 125

Arg Glu His Pro Asp Ser Ser Glu Arg Asp Tyr Tyr Ile Trp Cys Asp
    130                 135                 140

```
Gln Pro Asn Asp Leu Glu Ser Ile Phe Gly Gly Ser Ala Trp Gln Tyr
145                 150                 155                 160

Asp Asp Lys Ser Asp Gln Tyr Tyr Leu His Phe Ser Lys Lys Gln
    165                 170                 175

Pro Asp Leu Asn Trp Glu Asn Ala Asn Leu Arg Gln Lys Ile Tyr Asp
180                 185                 190

Met Met Asn Phe Trp Ile Asp Lys Gly Ile Gly Gly Phe Arg Met Asp
195                 200                 205

Val Ile Asp Met Ile Gly Lys Ile Pro Ala Gln His Ile Val Ser Asn
210                 215                 220

Gly Pro Lys Leu His Ala Tyr Leu Lys Glu Met Asn Ala Ala Ser Phe
225                 230                 235                 240

Gly Gln His Asp Leu Leu Thr Val Gly Glu Thr Trp Gly Ala Thr Pro
245                 250                 255

Glu Ile Ala Lys Gln Tyr Ser Asn Pro Val Asn His Glu Leu Ser Met
260                 265                 270

Ile Phe Gln Phe Glu His Ile Gly Leu Gln His Lys Pro Glu Ala Pro
275                 280                 285

Lys Trp Asp Tyr Val Lys Glu Leu Asn Val Pro Ala Leu Lys Thr Ile
290                 295                 300

Phe Asn Lys Trp Gln Thr Glu Leu Glu Leu Gly Gln Gly Trp Asn Ser
305                 310                 315                 320

Leu Phe Trp Asn Asn His Asp Leu Pro Arg Val Leu Ser Ile Trp Gly
325                 330                 335

Asn Thr Gly Lys Tyr Arg Glu Lys Ser Ala Lys Ala Leu Ala Ile Leu
340                 345                 350

Leu His Leu Met Arg Gly Thr Pro Tyr Ile Tyr Gln Gly Glu Glu Ile
355                 360                 365

Gly Met Thr Asn Tyr Pro Phe Lys Asp Leu Asn Glu Leu Asp Asp Ile
370                 375                 380

Glu Ser Leu Asn Tyr Ala Lys Glu Ala Phe Thr Asn Gly Lys Ser Met
385                 390                 395                 400

Glu Thr Ile Met Asp Ser Ile Arg Met Ile Gly Arg Asp Asn Ala Arg
405                 410                 415

Thr Pro Met Gln Trp Asp Ala Ser Gln Asn Ala Gly Phe Ser Thr Ala
420                 425                 430

Asp Lys Thr Trp Leu Pro Val Asn Pro Asn Tyr Lys Asp Ile Asn Val
435                 440                 445

Gln Ala Ala Leu Lys Asn Ser Asn Ser Ile Phe Tyr Thr Tyr Gln Gln
450                 455                 460

Leu Ile Gln Leu Arg Lys Glu Asn Asp Trp Leu Val Asp Ala Asp Phe
465                 470                 475                 480

Glu Leu Leu Pro Thr Ala Asp Lys Val Phe Ala Tyr Leu Arg Lys Val
485                 490                 495

Arg Glu Glu Arg Tyr Leu Ile Val Val Asn Val Ser Asp Gln Glu Glu
500                 505                 510

Val Leu Glu Ile Asp Val Asp Lys Gln Glu Thr Leu Ile Ser Asn Thr
515                 520                 525

Asn Glu Ser Ala Ala Leu Ala Asn His Lys Leu Gln Pro Trp Asp Ala
530                 535                 540

Phe Cys Ile Lys Ile Asn
545                 550
```

<210> SEQ ID NO 40
<211> LENGTH: 1860
<212> TYPE: DNA
<213> ORGANISM: Artificial sequence
<220> FEATURE:
<223> OTHER INFORMATION: Bacillus subtilis neutral protease gene
      signal peptide linked to the coding sequence for the
      Bifidobacterium breve mbc2g.pk018.k1 gene

<400> SEQUENCE: 40

```
atgagtttaa ccatcagtct gccgggtgtt caggctagcg cgatgatgac ctctttcaac      60
cgtgaacccc tgcccgacgc cgtccgcacg aatggcgcct ccccgaaccc gtggtggtcg     120
aacgccgtcg tctaccagat ttacccacgt tccttccagg acacgaacgg cgatggtttc     180
ggagatctta agggcattac ttcccgcctc gactatcttg ccgacctcgg cgtggatgtg     240
ctgtggctct ccccggtcta caggtccccg caagacgaca acggctacga catctccgac     300
taccgggaca cgacccgct gttcggcacg ctcgacgaca tggacgagct gctcgccgaa     360
gcgcacaagc gcggcctcaa gatcgtgatg gacctggtcg tcaaccacac ctccgacgag     420
cacgcgtggt tcgaggcgtc gaaggacaag gacgacccgc acgccgactg gtactggtgg     480
cgtcccgccc gccccggcca cgagcccggc acgcccggcg ccgagccgaa ccagtgggc     540
tcctacttcg gcggctccgc atgggaatat tgccccgagc gtggtgagta ctatctccac     600
cagttctcga agaagcagcc ggacctcaac tgggagaacc cggccgtacg ccgagccgtg     660
tacgacatga tgaactggtg gctcgatcgc ggcatcgacg gcttccgcat ggacgtcatc     720
accctgatct ccaagcgcac ggatgcaaac ggcaggctgc ccggcgagac cggttccgag     780
ctgcaggacc tgccggtggg ggaggagggc tactccaacc cgaacccgtt ctgcgccgac     840
ggtccgcgtc aggacgagtt cctcgccgag atgcgccgcg aggtgttcga cgggcgtgac     900
ggcttcctca ccgtcggcga ggcccccggc atcaccgccg aacgcaacga gcacatcacc     960
gaccccgcca acggcgagct ggatatgctc ttcctgttcg aacacatggg cgtcgaccaa    1020
accccgaat cgaaatggga cgacaaacca tggacgccgg ccgacctcga accaagctc    1080
gccgaacaac aggacgccat cgcccgacac ggctgggcca gcctgttcct cgacaaccac    1140
gaccagccgc gtgtcgtctc ccgttggggc gacgacacca gcaagaccgg ccgcatccgc    1200
tccgccaagg cgctcgcgct gctgctgcac atgcaccgcg gcactccgta tgtctaccag    1260
ggcgaggagc tcggcatgac caatgcgcac ttcacctcgc tcgaccagta ccgcgacctc    1320
gaatccatca cgcctacca tcaacgcgtc gaggaaaccg ggatacggac atcggagacc    1380
atgatgcgat ccctcgcccg ataccggcagg acaacgcgc gcaccccgat gcaatgggac    1440
gactccacct acgccggctt caccatgccc gacgccccgg tcgaaccctg gatcgccgtc    1500
aacccgaacc acacggagat caacgccgcc gacgagatcg acgacccga ctccgtgtac    1560
tcgttccaca acggctcat cgccctgcgt cacaccgacc ccgtggtcgc cgccggcgac    1620
taccgacgcg tggaaaccgg aaacgaccgg atcatcgcct tcaccagaac cctcgacgag    1680
cgaaccatcc tcaccgtcat caacctctcg cccacacagg ccgcaccggc cggagaactg    1740
gaaacgatgc ccgacggcac gatcctcatc gccaacacgg acgatcccgt aggaaaacctg    1800
aaaaccacgg gaacactcgg accatgggag gcgttcgcca tggaaaaccga tccggaataa    1860
```

<210> SEQ ID NO 41
<211> LENGTH: 619
<212> TYPE: PRT
<213> ORGANISM: Artificial sequence
<220> FEATURE:
<223> OTHER INFORMATION: Bacillus subtilis neutral protease gene
      signal peptide linked to the coding sequence for the
      Bifidobacterium breve mbc2g.pk018.k1 gene

<400> SEQUENCE: 41

```
Met Ser Leu Thr Ile Ser Leu Pro Gly Val Gln Ala Ser Ala Met Met
1               5                   10                  15

Thr Ser Phe Asn Arg Glu Pro Leu Pro Asp Ala Val Arg Thr Asn Gly
            20                  25                  30

Ala Ser Pro Asn Pro Trp Trp Ser Asn Ala Val Val Tyr Gln Ile Tyr
        35                  40                  45

Pro Arg Ser Phe Gln Asp Thr Asn Gly Asp Gly Phe Gly Asp Leu Lys
    50                  55                  60

Gly Ile Thr Ser Arg Leu Asp Tyr Leu Ala Asp Leu Gly Val Asp Val
65                  70                  75                  80

Leu Trp Leu Ser Pro Val Tyr Arg Ser Pro Gln Asp Asp Asn Gly Tyr
                85                  90                  95

Asp Ile Ser Asp Tyr Arg Asp Ile Asp Pro Leu Phe Gly Thr Leu Asp
            100                 105                 110

Asp Met Asp Glu Leu Leu Ala Glu Ala His Lys Arg Gly Leu Lys Ile
        115                 120                 125

Val Met Asp Leu Val Val Asn His Thr Ser Asp Glu His Ala Trp Phe
130                 135                 140

Glu Ala Ser Lys Asp Lys Asp Pro His Ala Asp Trp Tyr Trp Trp
                145                 150                 155                 160

Arg Pro Ala Arg Pro Gly His Glu Pro Gly Thr Pro Gly Ala Glu Pro
            165                 170                 175

Asn Gln Trp Gly Ser Tyr Phe Gly Gly Ser Ala Trp Glu Tyr Cys Pro
        180                 185                 190

Glu Arg Gly Glu Tyr Tyr Leu His Gln Phe Ser Lys Lys Gln Pro Asp
    195                 200                 205

Leu Asn Trp Glu Asn Pro Ala Val Arg Arg Ala Val Tyr Asp Met Met
210                 215                 220

Asn Trp Trp Leu Asp Arg Gly Ile Asp Gly Phe Arg Met Asp Val Ile
225                 230                 235                 240

Thr Leu Ile Ser Lys Arg Thr Asp Ala Asn Gly Arg Leu Pro Gly Glu
                245                 250                 255

Thr Gly Ser Glu Leu Gln Asp Leu Pro Val Gly Glu Glu Gly Tyr Ser
            260                 265                 270

Asn Pro Asn Pro Phe Cys Ala Asp Gly Pro Arg Gln Asp Glu Phe Leu
        275                 280                 285

Ala Glu Met Arg Arg Glu Val Phe Asp Gly Arg Asp Gly Phe Leu Thr
    290                 295                 300

Val Gly Glu Ala Pro Gly Ile Thr Ala Glu Arg Asn Glu His Ile Thr
305                 310                 315                 320

Asp Pro Ala Asn Gly Glu Leu Asp Met Leu Phe Leu Phe Glu His Met
                325                 330                 335

Gly Val Asp Gln Thr Pro Glu Ser Lys Trp Asp Asp Lys Pro Trp Thr
            340                 345                 350

Pro Ala Asp Leu Glu Thr Lys Leu Ala Glu Gln Gln Asp Ala Ile Ala
        355                 360                 365

Arg His Gly Trp Ala Ser Leu Phe Leu Asp Asn His Asp Gln Pro Arg
    370                 375                 380
```

```
Val Val Ser Arg Trp Gly Asp Asp Thr Ser Lys Thr Gly Arg Ile Arg
385                 390                 395                 400

Ser Ala Lys Ala Leu Ala Leu Leu Leu His Met His Arg Gly Thr Pro
405                 410                 415

Tyr Val Tyr Gln Gly Glu Leu Gly Met Thr Asn Ala His Phe Thr
420                 425                 430

Ser Leu Asp Gln Tyr Arg Asp Leu Glu Ser Ile Asn Ala Tyr His Gln
435                 440                 445

Arg Val Glu Glu Thr Gly Ile Arg Thr Ser Glu Thr Met Met Arg Ser
450                 455                 460

Leu Ala Arg Tyr Gly Arg Asp Asn Ala Arg Thr Pro Met Gln Trp Asp
465                 470                 475                 480

Asp Ser Thr Tyr Ala Gly Phe Thr Met Pro Asp Ala Pro Val Glu Pro
485                 490                 495

Trp Ile Ala Val Asn Pro Asn His Thr Glu Ile Asn Ala Ala Asp Glu
500                 505                 510

Ile Asp Asp Pro Asp Ser Val Tyr Ser Phe His Lys Arg Leu Ile Ala
515                 520                 525

Leu Arg His Thr Asp Pro Val Val Ala Ala Gly Asp Tyr Arg Arg Val
530                 535                 540

Glu Thr Gly Asn Asp Arg Ile Ile Ala Phe Thr Arg Thr Leu Asp Glu
545                 550                 555                 560

Arg Thr Ile Leu Thr Val Ile Asn Leu Ser Pro Thr Gln Ala Ala Pro
565                 570                 575

Ala Gly Glu Leu Glu Thr Met Pro Asp Gly Thr Ile Leu Ile Ala Asn
580                 585                 590

Thr Asp Asp Pro Val Gly Asn Leu Lys Thr Thr Gly Thr Leu Gly Pro
595                 600                 605

Trp Glu Ala Phe Ala Met Glu Thr Asp Pro Glu
610                 615

<210> SEQ ID NO 42
<211> LENGTH: 1653
<212> TYPE: DNA
<213> ORGANISM: Artificial sequence
<220> FEATURE:
<223> OTHER INFORMATION: Bacillus subtilis neutral protease gene
      signal peptide linked to the coding sequence for the
      Streptococcus mutans dexB gene

<400> SEQUENCE: 42
atgagtttaa ccatcagtct gccgggtgtt caggctagcg cgatgcaaaa acattggtgg      60
cacaaggcaa ctgtttatca aatttatcca aaatctttta tggatacaaa tggtgatgga     120
attggtgatc tcaaaggtat tacgagtaaa ttggattatt tgcaaaagtt agggggttatg    180 gctatttggc tatctccagt ttatgatagc cccatggatg acaatggcta tgacattgcg    240
aactatgaag caattgcgga tattttggc aatatggctg atatggataa tttgctgacg      300
caggcaaaaa tgcgcgacat aaaaatcatt atggatctag tggttaatca tacctcagat    360
gaacatactt ggtttattga agcacgtgag catccagaca gttctgaacg cgattattat    420
atttggtgtg accagccaaa tgatttggaa tctattttcg gtggttctgc ttggcagtat    480
gatgataagt ccgatcaata ttatttgcat ttttttagta agaagcagcc agatctaaac    540
tgggaaaacg caaacttacg tcagaagatt tatgatatga tgaatttctg gattgataaa    600
ggtattggcg gctttcggat ggacgtcatt gatatgattg ggaaaattcc tgctcagcat    660
```

```
attgtcagta acggaccaaa attgcatgct tatcttaagg agatgaatgc cgctagtttt    720
ggtcaacatg atctgctgac tgtgggggaa acttggggag caacgcctga gattgcgaag    780
caatattcaa atccagtcaa tcacgaactc tctatgattt ttcaatttga acatattggt    840
cttcagcata aaccagaagc tcctaaatgg gattatgtga aggaacttaa tgttcctgct    900
ttaaaaacaa tctttaataa atggcagact gagttggaat taggacaggg gtggaattcg    960
ttattctgga ataaccatga cctgcctcgt gttttatcaa tctggggaaa tacgggcaaa   1020
tatcgtgaga agtctgctaa agcactggct attcttcttc accttatgcg tgggacacct   1080
tatatttatc aaggtgaaga gattgggatg accaattatc cttttaaaga tttaaatgaa   1140
cttgatgata ttgaatcact taattatgct aaggaagctt ttacaaatgg taagtctatg   1200
gaaactatca tggacagtat tcgtatgatt ggccgtgata atgccagaac acctatgcaa   1260
tgggatgctt ctcaaaatgc cggattttca acagcggata aaacatggct gccagttaat   1320
ccaaactata aagacatcaa tgttcaagca gctctgaaaa attccaattc tatcttttac   1380
acctatcaac aactcattca gcttcgaaaa gaaaatgatt ggctagtaga tgccgatttt   1440
gaattgctcc ctacagcgga caaagtattt gcctatttac gaaaggtaag agaagaaagg   1500
tatcttatag tggtcaatgt ttcagatcag gaagaagttc tagagattga tgttgacaaa   1560
caagaaactc tcattagcaa tacaaatgaa agcgctgctc ttgccaatca caaactccag   1620
ccttgggatg cttttttgtat taagataaac taa                                1653
```

<210> SEQ ID NO 43
<211> LENGTH: 550
<212> TYPE: PRT
<213> ORGANISM: Artificial sequence
<220> FEATURE:
<223> OTHER INFORMATION: Bacillus subtilis neutral protease gene
    signal peptide linked to the coding sequence for the
    Streptococcus mutans dexB gene

<400> SEQUENCE: 43

```
Met Ser Leu Thr Ile Ser Leu Pro Gly Val Gln Ala Ser Ala Met Gln
1               5                   10                  15

Lys His Trp Trp His Lys Ala Thr Val Tyr Gln Ile Tyr Pro Lys Ser
20                  25                  30

Phe Met Asp Thr Asn Gly Asp Gly Ile Gly Asp Leu Lys Gly Ile Thr
35                  40                  45

Ser Lys Leu Asp Tyr Leu Gln Lys Leu Gly Val Met Ala Ile Trp Leu
50                  55                  60

Ser Pro Val Tyr Asp Ser Pro Met Asp Asp Asn Gly Tyr Asp Ile Ala
65                  70                  75                  80

Asn Tyr Glu Ala Ile Ala Asp Ile Phe Gly Asn Met Ala Asp Met Asp
85                  90                  95

Asn Leu Leu Thr Gln Ala Lys Met Arg Asp Ile Lys Ile Ile Met Asp
100                 105                 110

Leu Val Val Asn His Thr Ser Asp Glu His Thr Trp Phe Ile Glu Ala
115                 120                 125

Arg Glu His Pro Asp Ser Ser Glu Arg Asp Tyr Tyr Ile Trp Cys Asp
130                 135                 140

Gln Pro Asn Asp Leu Glu Ser Ile Phe Gly Gly Ser Ala Trp Gln Tyr
145                 150                 155                 160

Asp Asp Lys Ser Asp Gln Tyr Tyr Leu His Phe Phe Ser Lys Lys Gln
165                 170                 175
```

```
Pro Asp Leu Asn Trp Glu Asn Ala Asn Leu Arg Gln Lys Ile Tyr Asp
180                 185                 190

Met Met Asn Phe Trp Ile Asp Lys Gly Ile Gly Gly Phe Arg Met Asp
195                 200                 205

Val Ile Asp Met Ile Gly Lys Ile Pro Ala Gln His Ile Val Ser Asn
210                 215                 220

Gly Pro Lys Leu His Ala Tyr Leu Lys Glu Met Asn Ala Ala Ser Phe
225                 230                 235                 240

Gly Gln His Asp Leu Leu Thr Val Gly Glu Thr Trp Gly Ala Thr Pro
245                 250                 255

Glu Ile Ala Lys Gln Tyr Ser Asn Pro Val Asn His Glu Leu Ser Met
260                 265                 270

Ile Phe Gln Phe Glu His Ile Gly Leu Gln His Lys Pro Glu Ala Pro
275                 280                 285

Lys Trp Asp Tyr Val Lys Glu Leu Asn Val Pro Ala Leu Lys Thr Ile
290                 295                 300

Phe Asn Lys Trp Gln Thr Glu Leu Glu Leu Gly Gln Gly Trp Asn Ser
305                 310                 315                 320

Leu Phe Trp Asn Asn His Asp Leu Pro Arg Val Leu Ser Ile Trp Gly
325                 330                 335

Asn Thr Gly Lys Tyr Arg Glu Lys Ser Ala Lys Ala Leu Ala Ile Leu
340                 345                 350

Leu His Leu Met Arg Gly Thr Pro Tyr Ile Tyr Gln Gly Glu Glu Ile
355                 360                 365

Gly Met Thr Asn Tyr Pro Phe Lys Asp Leu Asn Glu Leu Asp Asp Ile
370                 375                 380

Glu Ser Leu Asn Tyr Ala Lys Glu Ala Phe Thr Asn Gly Lys Ser Met
385                 390                 395                 400

Glu Thr Ile Met Asp Ser Ile Arg Met Ile Gly Arg Asp Asn Ala Arg
405                 410                 415

Thr Pro Met Gln Trp Asp Ala Ser Gln Asn Ala Gly Phe Ser Thr Ala
420                 425                 430

Asp Lys Thr Trp Leu Pro Val Asn Pro Asn Tyr Lys Asp Ile Asn Val
435                 440                 445

Gln Ala Ala Leu Lys Asn Ser Asn Ser Ile Phe Tyr Thr Tyr Gln Gln
450                 455                 460

Leu Ile Gln Leu Arg Lys Glu Asn Asp Trp Leu Val Asp Ala Asp Phe
465                 470                 475                 480

Glu Leu Leu Pro Thr Ala Asp Lys Val Phe Ala Tyr Leu Arg Lys Val
485                 490                 495

Arg Glu Glu Arg Tyr Leu Ile Val Val Asn Val Ser Asp Gln Glu Glu
500                 505                 510

Val Leu Glu Ile Asp Val Asp Lys Gln Glu Thr Leu Ile Ser Asn Thr
515                 520                 525

Asn Glu Ser Ala Ala Leu Ala Asn His Lys Leu Gln Pro Trp Asp Ala
530                 535                 540

Phe Cys Ile Lys Ile Asn
545                 550
```